United States Patent
Bravi et al.

(10) Patent No.: US 7,259,163 B2
(45) Date of Patent: Aug. 21, 2007

(54) 4-(6-MEMBERED)-HETEROARYL ACYL PYRROLIDINE DERIVATIVES AS HCV INHIBITORS

(75) Inventors: Gianpaolo Bravi, Stevenage (GB); Rossella Guidetti, Stevenage (GB); David Haigh, Stevenage (GB); Charles David Hartley, Stevenage (GB); Peter David Howes, Stevenage (GB); Deborah Lynette Jackson, Stevenage (GB); Victoria Lucy Helen Lovegrove, Stevenage (GB); Pritom Shah, Stevenage (GB); Martin John Slater, Stevenage (GB); Katrina Jane Wareing, Stevenage (GB)

(73) Assignee: Glaxo Group Limited, Greenford (GB)

( * ) Notice: Subject to any disclaimer, the term of this patent is extended or adjusted under 35 U.S.C. 154(b) by 502 days.

(21) Appl. No.: 10/494,127

(22) PCT Filed: Oct. 30, 2002

(86) PCT No.: PCT/EP02/12176

§ 371 (c)(1), (2), (4) Date: Oct. 11, 2004

(87) PCT Pub. No.: WO03/037895

PCT Pub. Date: May 8, 2003

(65) Prior Publication Data
US 2005/0043390 A1   Feb. 24, 2005

(30) Foreign Application Priority Data

| Nov. 2, 2001 | (GB) | ................. 0126440.7 |
| Feb. 19, 2002 | (GB) | ................. 0203900.6 |
| Aug. 19, 2002 | (GB) | ................. 0219321.7 |

(51) Int. Cl.
*A61K 31/4965* (2006.01)
*A01N 43/54* (2006.01)
*C07D 239/42* (2006.01)
*C07D 241/00* (2006.01)
*C07D 241/02* (2006.01)

(52) U.S. Cl. ................. 514/249; 514/255.05; 514/256; 514/343; 544/8; 544/53; 544/56; 544/60; 544/63; 544/67; 544/96; 544/141; 544/180; 544/182; 544/212; 544/238; 544/335; 544/336; 544/353; 546/279.1

(58) Field of Classification Search ............. None
See application file for complete search history.

(56) References Cited

FOREIGN PATENT DOCUMENTS

| AT | 395007 | * 8/1992 |
| WO | WO93 18765 | 9/1993 |
| WO | WO99 54299 | 10/1999 |
| WO | WO 01 28996 | 4/2001 |

* cited by examiner

*Primary Examiner*—Zachary C Tucker
(74) *Attorney, Agent, or Firm*—Karen L. Prus

(57) ABSTRACT

Novel anti-viral agents of Formula

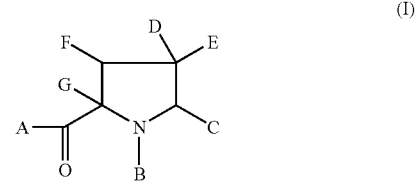

(I)

wherein:
A represents $OR^1$, $NR^1R^2$, or $R^1$ wherein $R^1$ and $R^2$ are hydrogen, $C_{1-6}$alkyl, aryl, heteroaryl, arylalkyl, or heteroarylalkyl; or $R^1$ and $R^2$ together with the nitrogen atom to which they are attached form a 5 or 6 membered saturated cyclic group;
B represents $C(O)R^3$ wherein $R^3$ is $C_{1-6}$alkyl, aryl, heteroaryl, arylalkyl, or heteroarylalkyl;
C represents $C_{1-6}$alkyl, aryl, heteroaryl or heterocyclyl;
D represents a saturated or unsaturated optionally substituted 6-membered heterocyclic ring;
E represents hydrogen or $C_{1-6}$alkyl;
F represents hydrogen, $C_{1-6}$alkyl, aryl or heteroaryl; and
G represents hydrogen, $C_{1-6}$alkyl, heterocyclylalkyl, arylalkyl or heteroarylalkyl; and salts, solvates and esters thereof, processes for their preparation and methods of using them in HCV treatment are provided.

12 Claims, No Drawings

4-(6-MEMBERED)-HETEROARYL ACYL PYRROLIDINE DERIVATIVES AS HCV INHIBITORS

This application is filed pursuant to 35 U.S.C. §371 as a United State National Phase Application of International Application No. PCT/EP02/12176 filed Oct. 30, 2002 which claims priority from GB 0126440.7 filed Nov. 2, 2001, GB 0203900.6 filed Feb. 19, 2002 and GB 0219321.7 filed Aug. 19, 2002 in Great Britain

FIELD OF THE INVENTION

The present invention relates to novel acyl pyrrolidine derivatives useful as anti-viral agents. Specifically, the present invention involves novel HCV inhibitors.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide, over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of those treated, 50-70% relapse within 6 months of cessation of treatment. Recently, with the introduction of pegylated interferon, both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), hepatitis C virus (HCV) is now widely accepted as the most common causative agent of post-transfusion non A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-3; Miller, R. H. and R. H. Purcell (1990) Proc. Natl. Acad. Sci. U.S.A. 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' [Article] RNA- A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p931-960; Raven Press, N.Y.). Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215:744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

The NS5B protein (591 amino acids, 65 kDa) of HCV (Behrens, S. E. et al (1996) EMBO J. 15:12-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) Journal of Virology, 74(4), p.2046-2051). Thus, inhibition of NS5B RdRp activity (inhibition of RNA replication) is predicted to cure HCV infection.

Based on the foregoing, there exists a significant need to identify synthetic or biological compounds for their ability to inhibit HCV.

SUMMARY OF THE INVENTION

The present invention involves compounds represented hereinbelow, pharmaceutical compositions comprising such compounds and use of the present compounds in treating viral infection, especially HCV infection.

DETAILED DESCRIPTION OF THE INVENTION

The present invention provides compounds of Formula (I):

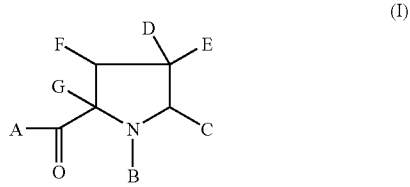

wherein:

A represents $OR^1$, $NR^1R^2$, or $R^1$ wherein $R^1$ and $R^2$ are independently selected from the group consisting of hydrogen, $C_{1-6}$alkyl, aryl, heteroaryl, arylalkyl, and heteroarylalkyl; or $R^1$ and $R^2$ together with the nitrogen atom to which they are attached form a 5 or 6 membered saturated cyclic group;

B represents $C(O)R^3$ wherein $R^3$ is selected from the group consisting of $C_{1-6}$alkyl, aryl, heteroaryl, arylalkyl, and heteroarylalkyl;

C represents $C_{1-6}$alkyl, aryl, heteroaryl or heterocyclyl;

D represents a saturated or unsaturated 6-membered heterocyclic ring comprising three or more carbon atoms, each of which may independently be optionally substituted by $R^4$ and $R^5$, and one to three heteroatoms independently selected from N, optionally substituted by hydrogen, $C_{1-6}$alkyl, $C(O)R^3$, $SO_2R^3$, aryl, heteroaryl, arylalkyl, or heteroarylalkyl; O; and S, optionally substituted by one or two oxygen atoms; wherein the 6 membered ring may be attached at any endocyclic carbon atom, and may be optionally fused to a saturated or unsaturated 5 or 6 membered carbocyclic or heterocyclic ring which may itself be optionally substituted on a non-fused carbon atom by $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, cyano, oxo, aryl, heteroaryl and heterocyclyl;

$R^4$ and $R^5$ are independently selected from hydrogen, $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, aryl, heteroaryl and heterocyclyl;

$R^6$ and $R^7$ are independently selected from hydrogen, $C_{1-6}$alkyl, aryl and heteroaryl; and $R^8$ represents hydrogen, $C_{1-6}$alkyl, arylalkyl, or heteroarylalkyl;

E represents hydrogen or $C_{1-6}$alkyl;

F represents hydrogen, $C_{1-6}$alkyl, aryl or heteroaryl; and

G represents hydrogen, $C_{1-6}$alkyl, heterocyclylalkyl, arylalkyl or heteroarylalkyl; and salts, solvates and esters thereof, provided that when A is $OR^1$ then $R^1$ is other than tert-butyl.

As used herein, "alkyl" refers to an optionally substituted hydrocarbon group. The alkyl hydrocarbon group may be linear, branched or cyclic, saturated or unsaturated. Where the alkyl hydrocarbon group is cyclic, it will be understood that there will be a minimum of 3 carbon atoms in the group. Preferably, the group is saturated. Preferred alkyl moieties are $C_{1-4}$alkyl. Optional substituents include $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SR^3$, $SO_2R^3$, nitro, oxo, cyano and heterocyclyl.

As used herein, "aryl" refers to an optionally substituted aromatic group with at least one ring having a conjugated pi-electron system, containing up to two conjugated or fused ring systems. "Aryl" includes carbocyclic aryl and biaryl groups, all of which may be optionally substituted. Preferred "aryl" moieties are unsubstituted, monosubstituted, disubstituted or trisubstituted phenyl. Preferred "aryl" substituents are selected from the group consisting of $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, heterocyclyl, $CF_3$, pyridine, phenyl, cyano, and $NO_2$.

As used herein, "heteroaryl" refers to an optionally substituted, 5 or 6 membered, aromatic group comprising one to four heteroatoms selected from N, O and S, with at least one ring having a conjugated pi-electron system, containing up to two conjugated or fused ring systems. Preferred "heteroaryl" moieties are unsubstituted, monosubstituted, disubstituted or trisubstituted thienyl and thiazolyl. Preferred "heteroaryl" substituents are selected from the group consisting of $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, heterocyclyl, $CF_3$, pyridine, phenyl, cyano, and $NO_2$.

As used herein, "heterocyclic" and "heterocyclyl" refer to an optionally substituted, 5 or 6 membered, saturated cyclic hydrocarbon group containing 1 to 4, preferably 1 or 2, heteroatoms, selected from N, optionally substituted by hydrogen, $C_{1-6}$alkyl, $C(O)R^3$, $SO_2R^3$, aryl or heteroaryl; O; and S, optionally substituted by one or two oxygen atoms.

It will be appreciated that the compounds of the present invention may contain one or more asymmetric carbon atoms and may exist in racemic, diastereoisomeric, and optically active forms. All of these racemic compounds, enantiomers and diastereoisomers are contemplated to be within the scope of the present invention.

Preferably, A is $OR^1$ where $R^1$ is hydrogen, or A is $NR^1R^2$ where $R^1$ and $R^2$ are both H. More preferably, A is $OR^1$ where $R^1$ is hydrogen.

Preferably, when B represents $C(O)R^3$, $R^3$ is aryl or heteroaryl; more preferably, $R^3$ is phenyl; especially preferred is $R^3$ represents phenyl substituted in the para-position by tert-butyl; most preferred is $R^3$ represents phenyl substituted in the para-position by tert-butyl and optionally further substituted, preferably meta-substituted, by methyl, ethyl, methoxy, ethoxy, or halo; more preferably methoxy.

Preferably, C is selected from the group consisting of $C_{1-6}$alkyl, aryl and heteroaryl; more preferably C is methyl; isopropyl; phenyl optionally substituted by phenyl or $NMe_2$; pyridinyl; 1,3-thiazinyl optionally substituted by halo, phenyl or $NMe_2$; thienyl; or benzthiazolyl.

Preferably, D is selected from the group (i) consisting of pyridyl, pyranyl, pyrimidinyl, pyridazinyl, pyrazinyl, 2H-1, 2-oxazinyl, 2H-1,3-oxazinyl, 2H-1,4-oxazinyl, 2H-1,2-thiazinyl, 2H-1,3-thiazinyl, 2H-1,4-thiazinyl, 1,2,3-triazinyl, 1,2,4triazinyl, 1,3,5-triazinyl, 2H-1,2,4-oxadiazinyl, 2H-1,2, 5-oxadiazinyl, 2H-1,3,4-oxadiazinyl, 2H-1,3,4-oxadiazinyl, 2H-1,3,5-oxadiazinyl, 2H-1,2,4thiadiazinyl, 2H-1,2,6-thiadiazinyl, 2H-1,3,4-thiadiazinyl, 2H-1,3,5-thiadiazinyl, 1,4, 2-dioxazinyl, 4H-1,3,5-dithiazinyl, 1,4,2-dithiazinyl, and partially or fully saturated derivatives thereof; each of which, where applicable, may be optionally substituted on a carbon atom by $R^4$ and $R^5$, on a nitrogen atom by hydrogen, $C_{1-6}$alkyl, $C(O)R^3$, $SO_2R^3$, aryl, heteroaryl, arylalkyl, or heteroarylalkyl, and on a sulphur atom by one or two oxygen atoms; and each of which may be optionally fused via two adjacent ring carbon atoms to a saturated or unsaturated 5 or 6 membered carbocyclic or heterocyclic ring which may itself be optionally substituted on a non-fused carbon atom by $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, cyano, oxo, aryl, heteroaryl and heterocyclyl; more preferably by $C_{1-6}$alkyl, halo, $OR^8$, $C(O)NR^6R^7$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, aryl, heteroaryl and heterocyclyl;

Preferably, when D is selected from group (i) and has a fused ring, the fused ring is selected from benzene, pyridine, pyrimidine, pyridazine and pyrazine. More preferably, when D is selected from group (i) and has a fused ring, D is quinoxalinyl;

More preferably, D is selected from optionally substituted pyridyl, pyrimidinyl, pyrazinyl, pyridazinyl or quinoxalinyl; most preferably, D is selected from pyridyl optionally substituted by trifluoromethyl or cyano; pyrimidinyl; pyrazinyl optionally substituted by methyl; pyridazinyl optionally substituted by methyl; or quinoxalinyl.

Preferably, E is hydrogen.

Preferably, F is hydrogen.

Preferably, G is selected from the group consisting of $C_{1-6}$alkyl, arylalkyl and heteroarylalkyl; more preferably, G is $C_{1-6}$alkyl, benzyl, pyridinylmethyl, N-methylamninocarbonylmethyl or aminocarbonylmethyl; most preferably, G is isobutyl, pyridin-2-ylmethyl or benzyl.

It is to be understood that the present invention covers all combinations of suitable, convenient and preferred groups described herein.

The present invention also provides compounds of Formula (Ia):

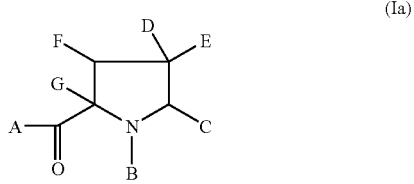

(Ia)

wherein:

A represents $OR^1$, $NR^1R^2$, or $R^1$ wherein $R^1$ and $R^2$ are independently selected from the group consisting of hydrogen, $C_{1-6}$alkyl, aryl, heteroaryl, arylalkyl, and heteroarylalkyl; or $R^1$ and $R^2$ together with the nitrogen atom to which they are attached form a 5 or 6 membered saturated cyclic group;

B represents $C(O)R^3$ wherein $R^3$ is selected from the group consisting of $C_{1-6}$alkyl, aryl, heteroaryl, arylalkyl, and heteroarylalkyl;

C represents $C_{1-6}$alkyl, aryl, heteroaryl or heterocyclyl;

D represents a saturated or unsaturated 6-membered heterocyclic ring comprising three or more carbon atoms, each of which may independently be optionally substituted by $R^4$ and $R^5$, and one to three heteroatoms independently selected from N, optionally substituted by hydrogen, $C_{1-6}$alkyl, $C(O)R^3$, $SO_2R^3$, aryl, heteroaryl, arylalklyl, or heteroarylalkyl; O; and S, optionally substituted by one or two oxygen atoms; wherein the 6 membered ring may be attached at any endocyclic carbon atom, and may be optionally fused to a saturated or unsaturated 5 or 6 membered carbocyclic or heterocyclic ring which may itself be optionally substituted on a non-fused carbon atom by $C_{1-6}$alkyl, halo, $OR^8$, $C(O)NR^6R^7$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, aryl, heteroaryl and heterocyclyl;

$R^4$ and $R^5$ are independently selected from hydrogen, $C_{1-6}$alkyl, halo, $OR^8$, $C(O)NR^6R^7$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, aryl, heteroaryl and heterocyclyl;

$R^6$ and $R^7$ are independently selected from hydrogen, $C_{1-6}$alkyl, aryl and heteroaryl; and $R^8$ represents hydrogen, $C_{1-6}$alkyl, arylalkyl, or heteroarylalkyl;

E represents hydrogen or $C_{1-6}$alkyl;

F represents hydrogen, $C_{1-6}$alkyl, aryl or heteroaryl; and

G represents hydrogen, $C_{1-6}$alkyl, heterocyclylalkyl, arylalkyl or heteroarylalkyl; and salts and solvates thereof, provided that when A is $OR^1$ then $R^1$ is other than tert-butyl.

Preferred compounds useful in the present invention are selected from the group consisting of:

rel-(2S,4S,5R)-1-(4-tert-butylbenzoyl)-2-isobutyl-4-(pyrazin-2-yl)-5-1,3-thiazol-2-yl)pyrrolidine-2-carboxylic acid;

rel-(2S,4S,5R)-1-(4-tert-butylbenzoyl)-2-isobutyl-4-(5-methyl-pyrazin-2-yl)-5-(1,3-thiazol-2-yl)pyrrolidine-2-carboxylic acid;

rel-(2S,4S,5R)-1-(4-tert-butylbenzoyl)-2-isobutyl-4-(pyridin-2-yl)-5-(1,3-thiazol-2yl)pyrrolidine-2-carboxylic acid;

rel-(2S,4R,5R)-1-(4-tert-butylbenzoyl)-2-isobutyl-4-(pyridin-4-yl)-5-(1,3-thiazol-2-yl)pyrrolidine-2-carboxylic acid;

rel-(2S,4S,5R)-1-(4-tert-butylbenzoyl)-2-isobutyl-4-(pyrimidin-5-yl)-5-(1,3-thiazol-2-yl)pyrrolidine-2-carboxylic acid;

rel-(2S,4S,5R)-1-(4-tert-butylbenzoyl)-2-isobutyl-4-(6-methyl-pyridazin-2-yl)-5-(1,3-thiazol-2-yl)pyrrolidine-2-carboxylic acid;

rel-(2S,4S,5R)-1-(4-tert-butylbenzoyl)-2-isobutyl-4-(pyrazin-2-yl)-5-(pyridin-2-yl)pyrrolidine-2-carboxylic acid;

rel-(2S,4S,5R)-1-(3-bromo-4-tert-butylbenzoyl)-2-isobutyl-4-(pyrazin-2-yl)-5-(pyridin-2-yl)pyrrolidine-2-carboxylic acid;

rel-(2S,4S,5R)-1-(3-bromo-4-tert-butylbenzoyl)-2-isobutyl-4-(pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(5-methyl-pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(pyridazin-3-yl)-5-(1,3-thiazol-2-yl)pyrrolidine-2-carboxylic acid;

rel-(2S,4S,5R)-1-(4-tert-butylbenzoyl)-2-isobutyl-4-(pyrazin-2-yl)-5-(1,3-benzothiazol-2-yl)pyrrolidine-2-carboxylic acid;

rel-(2S,4S,5R)-1-(3-bromo-4-tert-butylbenzoyl)-2-isobutyl-4-(pyrazin-2-yl)-5-(1,3-benzothiazol-2-yl)pyrrolidine-2-carboxylic acid;

rel-(2S,4S,5R)-1-(4-tert-butyl-3-chlorobenzoyl)-2-isobutyl-4-(pyrazin-2-yl)-5-(1,3-thiazol-2-yl)pyrrolidine-2-carboxylic acid;

rel-(2S,4S,5R)-1-(4-tert-butyl-3-methoxybenzoyl)-2-isobutyl-4-(pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(pyrazin-2-yl)-5-(pyridin-2-yl)pyrrolidine-2-carboxamide;

rel-(2S,4S,5R)-1-(4-tert-butylbenzoyl)-2-isobutyl-4-(quinoxalin-2-yl)-5-(1,3-thiazol-2-yl)pyrrolidine-2-carboxylic acid;

rel-(2S,4S,5R)-1-(4-tert-butylbenzoyl)-2-isobutyl-4-(trifluoromethyl-pyridin-2-yl)-5-1,3-thiazol-2-yl)pyrrolidine-2-carboxylic acid;

rel-(2S,4S,5R)-1-(4-tert-butyl-3-methylbenzoyl)-2-isobutyl-4-(pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(pyrazin-2-yl)-5-(1,3-thiazol-2-yl)pyrrolidine-2-carboxamide;

rel-(2S,4S,5R)-1-(4-tert-butyl-3-methoxybenzoyl)-2-isobutyl-4-(pyrazin-2-yl)-5-(pyridin-2-yl)pyrrolidine-2-carboxylic acid;

rel-(2S,4S,5R)-1-(4-tert-butylbenzoyl)-2-isobutyl-4-(pyrazin-2-yl)-5-(2-chloro-1,3-thiazol-5-yl)pyrrolidine-2-carboxylic acid;

rel-(2S,4S,5R)-1-(4-tert-butyl-3-chlorobenzoyl)-2-isobutyl-4-(pyrazin-2-yl)-5-(pyridin-2-yl)pyrrolidine-2-carboxylic acid;

rel-(2S,4S,5R)-1-(4-tert-butyl-3-methoxybenzoyl)-2-isobutyl-4-(pyrazin-2-yl)-5-(2-chloro-1,3-thiazol-5-yl)pyrrolidine-2-carboxylic acid;

rel-(2S,4S,5R)-1-(4tert-butylbenzoyl)-2-isobutyl-4-(6-methyl-pyrazin-2-yl)-5-1,3-thiazol-2-yl)pyrrolidine-2-carboxylic acid;

rel-(2S,4S,5R)-1-(4-tert-butyl-3-metoxybenzoyl)-2-isobutyl-4-pyrazin-2-yl)-5-phenyl-pyrrolidine-2-carboxylic acid;

rel-(2S,4S,5R)-1-(4-tert-butylbenzoyl)-2-isobutyl-4-(pyrazin-2-yl)-5-phenyl -pyrrolidine-2-carboxylic acid, rel-(2S,4S,5S)-1-(4-tert-butyl-3-methoxybenzoyl)-2-isobutyl-4-(pyrazin-2-yl)-5-methyl-pyrrolidine-2-carboxylic acid;

rel-(2S,4S,5R)-1-(4-tert-butyl-3-methoxybenzoyl)-2-isobutyl 4-(pyrazin-2-yl)-5-(pyridin-3-yl)-pyrrolidine-2-carboxylic acid;

rel-(2S,4S,5R)-1-(4-tert-butyl-3-methoxybenzoyl)-2-isobutyl-4-(pyrazin-2-yl)-5-(thien-2-yl)pyrrolidine-2-carboxylic acid;

rel-(2S,4S,5R)-1-(4-tert-butylbenzoyl)-2-isobutyl-4-(pyrazin-2-yl)-5-(1,3-thiazol-4-yl)pyrrolidine-2-carboxylic acid;

rel-(2S,4S,5R)-1-(4-tert-butyl-3-methoxybenzoyl)-2-isobutyl-4-(pyrazin-2-yl)-5-(2-dimethylamino-1,3-thiazol-4-yl)pyrrolidine-2-carboxylic acid;

rel-(2S,4S,5R)-1-(4-tert-butyl-3-methoxybenzoyl)-2-isobutyl-4-(pyrazin-2-yl)-5-thiazol-4-yl)pyrrolidine-2-carboxylic acid;

rel-(2S,4S,5R)-1-(4-tert-butylbenzoyl)-2-isobutyl-4-(pyrazin-2-yl)-5-(pyridin-3-yl)-pyrrolidine-2-carboxylic acid, rel-(2S,4S,5R)-1-(4-tert-butyl-3-methoxybenzoyl)-2-(pyridin-2-ylmethyl)-4-(pyrazin-2-yl)-5-(1,3-thiazol-2-yl)pyrrolidine-2-carboxylic acid;

rel-(2S,4S,5R)-1-(4-tert-butyl-3-methoxybenzoyl)-2-(N-methylaminocarbonylmethyl)4-(pyrazin-2-yl)-5-(1,3-thiazol-2-yl)pyrrolidine-2-carboxylic acid;

rel-(2S,4S,5R)-1-(4-tert-butyl-3-methoxybenzoyl)-2-(aminocarbonylmethyl)4-(pyrazin-2-yl)-5-(1,3-thiazol-2-yl)pyrrolidine-2-carboxylic acid;

rel-(2S,4S,5R)-1-(4-tert-butylbenzoyl)-2-isobutyl-4-(pyrazin-2-yl)-5-(3-phenyl phenyl)-pyrrolidine-2-carboxylic acid;

(2S,4S,5R)-1-(4-tert-butyl-3-methoxybenzoyl)-2-isobutyl-4-(pyrazin-2-yl)-5-(1,3-thiazol-2-yl)pyrrolidine-2-carboxamide;

(2S,4R,5R)-1-(4-tert-butylbenzoyl)-2-isobutyl-4-(5-trifluoromethylpyridin-2-yl)-5-(1,3-thiazol-2-yl)pyrrolidine-2-carboxamide;

rel-(2S,4S,5R)-1-(4-tert-butylbenzoyl)-2-isobutyl-4 (pyrazin-2-yl)-5-(1,3-thiazol-5-yl)pyrrolidine-2-carboxylic acid;

rel-(2S,4S,5R)-1-(4-tert-butyl-3-methoxybenzoyl)-2-isobutyl-4-(pyrazin-2-yl)-5-4-dimethylaminophenyl)-pyrrolidine-2-carboxylic acid;

rel-(2S,4S,5R)-1-(4-tert-butylbenzoyl)-2-isobutyl-4-(pyrazin-2-yl)-5-4-dimethylaminophenyl)-pyrrolidine-2-carboxylic acid, rel-(2S,4S,5R)-1-(4-tert-butyl-3-methoxybenzoyl)-2-(1H-imidazol-4yl-methyl)-4-(pyrazin-2-yl)-5-(1,3-thiazol-2-yl)-pyrrolidine-2-carboxylic acid;

rel-(2S,4S,5S)-1-(4-tert-butyl-3-methoxybenzoyl)-2-isobutyl-4-(pyrazin-2-yl)-5-isopropyl-pyrrolidine-2-carboxylic acid;

rel-(2S,4S,5R)-1-(4-tert-butyl-3-methoxybenzoyl)-2-(2-(methylthio)ethyl)-4-(pyrazin-2-yl)-5-(1,3-thiazol-5-yl)-pyrrolidine-2-carboxylic acid;

rel-(2S,4R,5R)-1-(4-tert-butylbenzoyl)-2-isobutyl-4-(pyrazin-2-yl)-5-(1,3-thiazol-2-yl)pyrrolidine-2-carboxylic acid;

rel-(2S,4S,5R)-1-(4-tert-butyl-3-methoxybenzoyl)-2-isobutyl-4-(pyrazin-2-yl)-5-(1,3-thiazol-5-yl)pyrrolidine-2-carboxylic acid;

rel-(2S,4S,5R)-1-(4-tert-butylbenzoyl)-2-isobutyl-4-(4-cyanopyridin-2-yl)-5-(1,3-thiazol-5-yl)pyrrolidine-2-carboxylic acid;

rel-(2S,4R,5R)-1-(4-tert-butylbenzoyl)-2-isobutyl-4-(pyrimidin-4-yl)-5-(1,3-thiazol-5-yl)pyrrolidine-2-carboxylic acid;

rel-(2S,4S,5R)-1-(4-tert-butylbenzoyl)-2-isobutyl-4-(pyrimidin-4-yl)-5-(1,3-thiazol-5-yl)pyrrolidine-2-carboxylic acid;

rel-(2S,4S,5R)-1-(4-tert-butyl-3-methoxybenzoyl)-2-(2-(methylsulphonyl)ethyl)-4-(pyrazin-2-yl)-5-(1,3-thiazol-2-yl)pyrrolidine-2-carboxylic acid;

rel-(2S,4R,5R)-1-(4-tert-butyl-3-methoxybenzoyl)-2-isobutyl-4-(pyrazin-2-yl)-5-1,3-thiazol-2-yl)pyrrolidine-2-carboxylic acid;

rel-(2S,4S,5R)-1-(4-tert-butyl-3-methylbenzoyl)-2-isobutyl-4-(pyrazin-2-yl)-5-(1,3-thiazol-2-yl)pyrrolidine-2-carboxylic acid;

rel-(2S,4S,5R)-1-(4-tert-butyl-3-methoxybenzoyl)-2-methyl-4(pyrazin-2-yl)-5-(1,3-thiazol-5-yl)pyrrolidine-2-carboxylic acid;

rel-(2S,4S,5R)-1-(4-tert-butyl-3-chlorobenzoyl)-2-methyl-4(pyrazin-4-yl)-5-(1,3-thiazol-5-yl)pyrrolidine-2-carboxylic acid;

(2S,4R,5R)-1-(4-tert-butyl-3-methoxybenzoyl)-2-isobutyl-4 (pyrazin-2-yl)-5(pyridin-2-yl)pyrrolidine-2-carboxylic acid;

rel-(2S,4S,5R)-1-(4-tert-butyl-3-methylbenzoyl)-2-isobutyl-4-(pyrazin-2-yl)-5-(1,3-thiazol-4-yl)pyrrolidine-2-carboxylic acid;

rel-(2S,4S,5R)-1-(4-tert-butylbenzoyl)-2-isobutyl-4-(pyrazin-2-yl)-5-(2-phenyl-1,3-thiazol-4-yl)pyrrolidine-2-carboxylic acid;

rel-(2S,4S,5R)-1-(4-tert-butyl-3-ethylbenlzoyl)-2-isobutyl-4-(pyrazin-2-yl)-5-(1,3-thiazol-2-yl)pyrrolidine-2-carboxylic acid;

rel-(2S,4S,5R)-1-(4-text-butyl-3-ethoxybenzoyl)-2-isobutyl-4-(pyrazin-2-yl)-5-1,3-thiazol-2-yl)pyrrolidine-2-caboxylic acid; and rel-(2S,4S,5R)-1-(4-tert-butyl-3-methoxybenzoyl)-2-(phenylmethyl)-4-(pyrazin-2-yl)-5-1,3-thiazol-2-yl)pyrrolidine-2-carboxylic acid;

and salts, solvates and esters, and individual enantiomers thereof.

In a preferred aspect, the present invention provides compounds of Formula (I) selected from the group consisting of Examples 1 to 25 hereinafter defined, and salts, solvates and esters, and where appropriate, individual enantiomers thereof. In a further preferred aspect, the present invention provides compounds of Formula (I) selected from the group consisting of Examples 1 to 2 hereinafter defined, and salts, solvates and esters, and where appropriate, individual enantiomers thereof.

Also included in the present invention are pharmaceutically acceptable salt complexes. The present invention also covers the physiologically acceptable salts of the compounds of formula (I). Suitable physiologically acceptable salts of the compounds of formula (I) include acid salts, for example sodium, potassium calcium, magnesium and tetraalkylammonium and the like, or mono- or di-basic salts with the appropriate acid for example organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids and the like.

The present invention also relates to solvates of the compounds of Formula (I), for example hydrates.

The present invention also relates to pharmaceutically acceptable esters of the compounds of Formula (I) and (Ia), for example carboxylic acid esters —COOR, in which R is selected from straight or branched chain alkyl, for example n-propyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$alkyl or $C_{1-4}$alkoxy or amino). Unless otherwise specified, any alkyl moiety present in such esters preferably contains 1 to 18 carbon atoms, particularly 1 to 4 carbon atoms. Any aryl moiety present in such esters preferably comprises a phenyl group.

It will further be appreciated that certain compounds of the present invention may exist in different tautomeric forms. All tautomers are contemplated to be within the scope of the present invention.

Compounds of Formula (I) may be prepared from a compound of Formula (II)

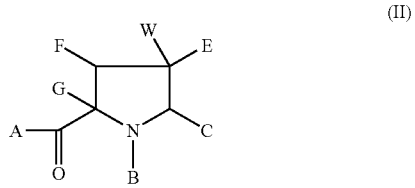

(II)

in which A, B, C, E, F and G are as defined above for Formula (I); W represents —CHO, —C(O)Me, —CO$_2$H, —CO$_2$R$^9$, —C(O)NR$^6$R$^7$, —CN or —C(O)Hal; and R$^9$ represents $C_{1-6}$alkyl, or arylalkyl; by any suitable method for the conversion of the moiety W into the moiety D of formula (I). Suitable methods for the conversion of W into D may be found in the chemical literature, for example those described in Comprehensive Heterocyclic Chemistry, Edited by A. R. Katritzky and C. W. Rees, Pergamon 1984; WO 2001/28996 and WO 99/54299.

Compounds of Formula (II) may be prepared by reaction of a compound of Formula (III)

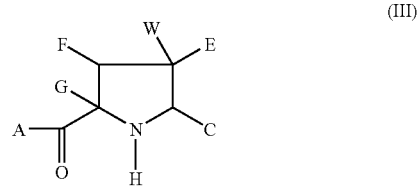

(III)

in which A, C, E, F and G are as defined above for Formula (I); and W is as defined above for Formula (II); with a suitable acylating agent, for example R$^3$C(O)-hal, wherein hal is a halo atom, preferably chloro or bromo. Preferably the reaction is carried out in a suitable solvent, for example dichloromethane, in the presence of a suitable base, for example triethylamine.

Compounds of Formula (III) may be prepared by reaction of a compound of Formula (IV)

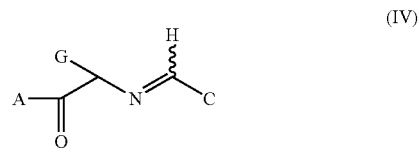

(IV)

wherein A, C and G are as defined for Formula (I) above; with a compound of Formula (V)

(V)

wherein E and F are as defined for Formula (I) and W is as defined for Formula (II) above. Preferably, the reaction is carried out in a suitable solvent, for example THF or acetonitrile, optionally in the presence of a Lewis acid catalyst, such as lithium bromide or silver acetate, and a base, such as triethylamine, 1,8-diazabicyclo[5,4,0]undec-7-ene (DBU) or tetramethyl guanidine. Alternatively, the reaction is carried out in a suitable solvent, for example THF or acetonitrile, in the presence of an acid, such as acetic acid, or the reaction may be carried out by heating compounds of Formula (IV) and Formula (V) in a suitable solvent, for example toluene, xylene or acetonitrile in the absence of a catalyst Compounds of Formula (IV) and (V) are known in the art or may be prepared by standard literature procedures.

Compounds of Formula (I) may also be prepared by reaction of a compound of Formula (VI)

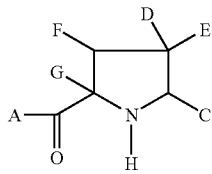
(VI)

in which A, C, D, E, F and G are as defined above for Formula (I); with a suitable acylating agent, for example R³C(O)-hal, wherein hal is a halo atom, preferably chloro or bromo. Preferably the reaction is carried out in a suitable solvent, for example dichloromethane, in the presence of a suitable base, for example triethylamine.

Compounds of Formula (VI) may be prepared by reaction of a compound of Formula (VII)

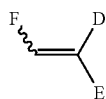
(VII)

wherein E, D and F are as described for Formula (I) above; with a compound of Formula (IV). Preferably, the reaction is carried out in a suitable solvent, for example THF or acetonitrile, optionally in the presence of a Lewis acid catalyst, such as lithium bromide or silver acetate, and a base, such as triethylamine, DBU or tetramethyl guanidine. Alternatively, the reaction is carried out in a suitable solvent, for example THF or acetonitrile, in the presence of an acid, such as acetic acid, or the reaction may be carried out by heating compounds of Formula (VII) and Formula (IV) in a suitable solvent, for example toluene, xylene or acetonitrile in the absence of a catalyst.

Compounds of Formula (VII) may be prepared from compounds of Formula (VIII) or (IX)

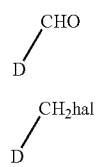
(VIII)
(IX)

in which D is as defined for Formula (I) above and hal is a halogen, by methods known in the art, for example a Wittig reaction, a Peterson olefination or a Julia reaction.

Compounds of Formula (VII) may be also prepared from compounds of Formula (X)

(X)

in which Z is a halogen or a triflate by methods known in the art, for example treatment with vinyl magnesium bromide, zinc bromide and a palladium catalyst such as tetrakis(triphenylphosphine)palladium(0), or by a Heck procedure with an acetylene followed by Lindlar reduction to the olefin.

It will be appreciated that compounds of Formula (I), (II), (III) and/or (VI) which exist as diastereoisomers may optionally be separated by techniques well known in the art, for example by column chromatography.

It will also be appreciated that the present invention provides a method for the interconversion of the rel-(2S, 4S, 5R)-diastereoisomer of a compound of formula (I) or (II) wherein A is other than hydroxy and E represents hydrogen, into the rel-(2S, 4R, 5R)-diastereoisomer. For example base-catalysed epimerisation by treatment of the rel-(2S, 4S, 5R)-diastereoisomer with a suitable base, such as aqueous sodium hydroxide, in the presence of a suitable solvent, such as methanol It will be appreciated that racemic compounds of Formula (I), (II), (III) and/or (VI) may be optionally resolved into their individual enantiomers. Such resolutions may conveniently be accomplished by standard methods known in the art. For example, a racemic compound of Formula (I), (II), (III) and/or (VI) may be resolved by chiral preparative HPLC. Alternatively, racemic compounds of Formula (I), (II), (III) and/or (VI) may be resolved by standard diastereoisomeric salt formation with a chiral acid or base reagent as appropriate. Such techniques are well established in the art. For example, a racemic compound of Formula (III) where W is C(O)NR⁶R⁷ and R⁶ and R⁷ are both hydrogen may be resolved by treatment with a chiral acid such as (−)di-O,O'-p-tolyl-L-tartaric acid. For example, a racemic compound of Formula (VI) where D is pyrazin-2-yl may be resolved by treatment with a chiral acid such as (R)-(−)-1,1'-binaphthyl-2,2'-diylhydrogen phosphate.

With appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts 'Protective Groups in Organic Synthesis', 3$^{rd}$ Ed (1999), J Wiley and Sons.

EXAMPLES

Intermediate 1

2-[N-(1,3-Thiazol-2-ylmethylene)amino]-4-methyl-pentanoic acid, tert-butyl ester

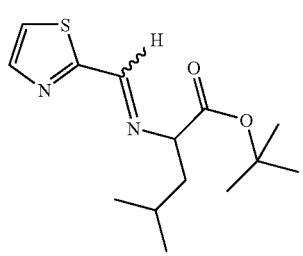

A stirred mixture of 2-amino-4-methyl-pentanoic acid tert-butyl ester, hydrochloride (5.00 g, 22.34 mmol), 1,3-thiazole-2-carboxaldehyde (2.53 g, 22.34 mmol) and triethylamine (3.1 mL, 22.3 mmol) in dichloromethane (60 mL) was heated under reflux under nitrogen for 19 hours. The reaction mixture was allowed to cool to room temperature, washed twice with water, dried over Na₂SO₄ and evaporated to give the title compound as an oil.

¹H NMR (CDCl₃): δ 8.46 (s, 1H), 7.94 (d, 1H), 7.44 (dd, 1H), 4.07 (dd, 1H), 1.89-1.74 (m, 2H), 1.64-1.52 (m, 1H), 1.48 (s, 9H), 0.96 (d, 3H) and 0.90 (d, 3H).

Intermediate 2 rel-(2S,4S,5R)-2-Isobutyl-4-pyrazin-2yl-5-(1,3-thiazol-2-yl)pyrrolidine-2-carboxylic acid, tert-butyl ester

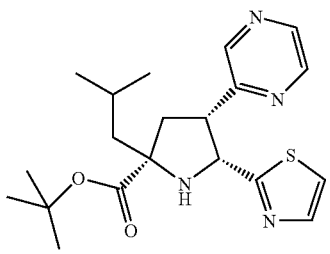

Racemic;
Relative stereochemistry shown

To a cooled (0° C.) stirred solution of Intermediate 1 (0.202 g, 0.72 mmol) in anhydrous THF (3 mL) under nitrogen, was added 2-vinylpyrazine (104 μL, 1.1 mmol) followed by lithium bromide (0.131 g, 1.51 mmol) and triethylamine (153 μL, 1.1 mmol). The reaction was stirred in a cooling bath for 5 min. and then at ambient temperature overnight. Aqueous ammonium chloride (20 mL) was added and the resulting mixture was extracted with ethyl acetate (20 mL). The extracts were combined and washed with water and brine then dried (MgSO₄). The solvent was evaporated in vacuo to give the crude product. This was purified by chromatography on silica gel using cyclohexane-ethyl acetate (1:1 v/v) as eluent to provide the title compound as a gum.

MS calcd for $(C_{20}H_{28}N_4O_2S+H)^+$: 389.
MS found (electrospray): $(M+H)^+=389$.

Intermediate 3 rel-(2S,4S,5R)-1-(4tert-Butylbenzoyl)-2-isobutyl-4-pyrazin-2-yl-5-(1,3-thiazol-2-yl)pyrrolidine-2-carboxylic acid, tert-butyl ester

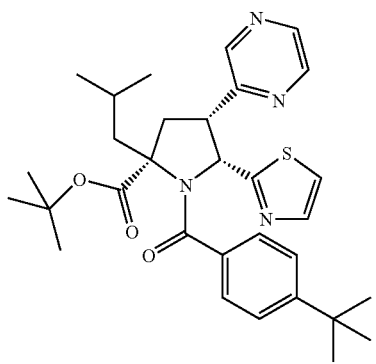

Racemic;
Relative stereochemistry shown

To a stirred solution of Intermediate 2 (86 mg, 0.22 mmol) in anhydrous dichloromethane (3 mL) was added triethylamine (38 μL, 0.28 mmol) and 4-tert-butylbenzoyl chloride (47 μL, 0.24 mmol). This mixture was stirred for 16 hours and was then diluted with dichloromethane and washed with water. The organic phase was dried (MgSO₄) and evaporated in vacuo. The residue was purified by chromatography on silica gel using ethyl acetate-cyclohexane (2:3 v/v) as eluent to provide the title compound as an oil.

MS calcd for $(C_{31}H_{40}N_4O_3S+H)^+$: 549.
MS found (electrospray): $(M+H)^+=549$.

Intermediate 4 rel-(2S,4S,5R)-2-Isobutyl-4-(5-methyl-pyrazin-2-yl)-5-(1,3-thiazol-2-yl)pyrrolidine-2-carboxylic acid, tert-butyl ester

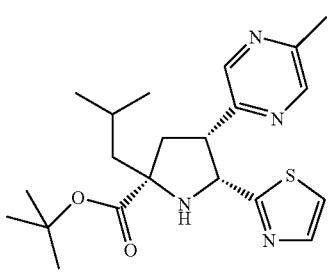

Racemic;
Relative stereochemistry shown

The title compound was prepared in a similar manner to that described for Intermediate 2, substituting 2-methyl-5-vinylpyrazine for 2-vinylpyrazine.

MS calcd for $(C_{21}H_{42}N_4O_3S+H)^+$: 403.
MS found (electrospray): $(M+H)^+=403$.

Intermediate 5 rel-(2S,4S,5R)-1-(4-tert-Butylbenzoyl)-2-isobutyl-4-(5-methyl-pyrazin-2-yl)-5-(1,3-thiazol-2-yl)pyrrolidine-2-carboxylic acid, tert-butyl ester

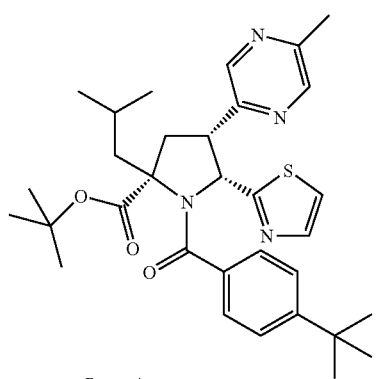

Racemic;
Relative stereochemistry shown

The title compound was prepared from Intermediate 4 in a similar manner to that described for Intermediate 3.

MS calcd for $(C_{32}H_{42}N_4O_3S+H)^+$: 563.
MS found (electrospray): $(M+H)^+=563$.

Intermediate 6 rel-(2S,4S,5R)-2-Isobutyl-4-(pyridin-2-yl)-5-(1,3-thiazol-2-yl)pyrrolidine-2-carboxylic acid, tert-butyl ester

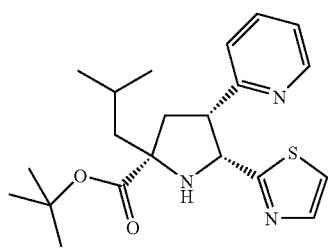

Racemic;
Relative stereochemistry shown

Prepared in a similar manner to that described for Intermediate 2, replacing 2-vinylpyrazine with 2-vinylpyridine. After stirring overnight at room temperature, the reaction was heated at reflux for 9 hours. The product was purified by chromatography on silica gel using cyclohexane-ethyl acetate (3:2 v/v) as eluent to provide the title compound as a liquid.

MS calcd for $(C_{21}H_{29}N_3O_2S+H)^+$: 388.
MS found (electrospray): $(M+H)^+=388$.

Intermediate 7 rel-(2S,4S,5R)-1-(4-tert-Butylbenzoyl)-2-isobutyl-4-pyridin-2-yl-5-(1,3thiazol-2-yl)pyrrolidine-2-carboxylic acid, tert-butyl ester

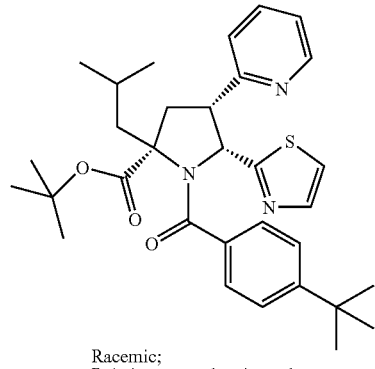

Racemic;
Relative stereochemistry shown

The title compound was prepared from Intermediate 6 in a similar manner to that described for Intermediate 3. The product was purified by chromatography on silica gel using cyclohexane-ethyl acetate (7:3 v/v) as eluent to provide the title compound as a foam.

MS calcd for $(C_{32}H_{41}N_3O_3S+H)^+$: 548.
MS found (electrospray): $(M+H)^+=548$.

Intermediate 8 rel-(2S,4R,5R)-2-Isobutyl-4-(pyridin-4-yl)-5-(1,3-thiazol-2-yl)pyrrolidine-2-carboxylic acid, tert-butyl ester

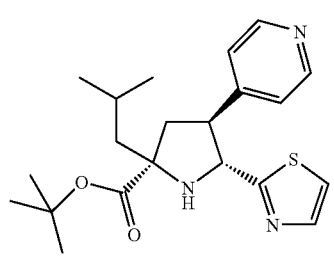

Racemic;
Relative stereochemistry shown

Prepared as previously described for Intermediate 2, substituting 4-vinylpyridine for 2-vinylpyrazine. The product was purified by chromatography on silica gel using ethyl acetate as eluent to provide the title compound as a liquid.

MS calcd for $(C_{21}H_{29}N_3O_2S+H)^+$: 388.
MS found (electrospray): $(M+H)^+=388$.

Intermediate 9 rel-(2S,4R,5R)-1-(-4-tert-Butylbenzoyl)-2-isobutyl-4-pyridin-2-yl-5-(1,3-thiazol-2-yl)pyrrolidine-2-carboxylic acid, tert-butyl ester

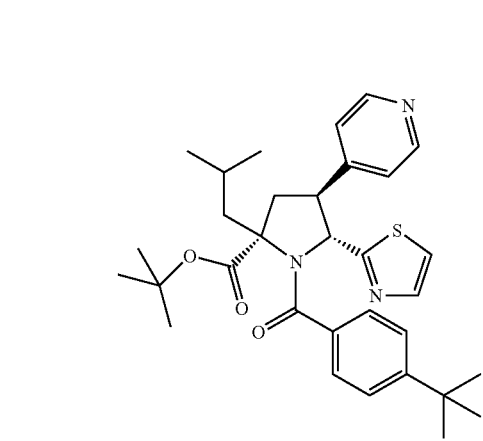

Racemic;
Relative stereochemistry shown

The title compound was prepared from Intermediate 8 in a similar manner to that described for Intermediate 3. The product was purified by chromatography on silica gel using cyclohexane-ethyl acetate (3:2 v/v) as eluent to provide the title compound as a gum. The stereochemistry was confirmed by nOe studies.

MS calcd for $(C_{32}H_{41}N_3O_3S+H)^+$: 548.
MS found (electrospray): $(M+H)^+=548$.

Intermediate 10 rel-(2S,4S,5R)-2-Isobutyl-4-(pyrimidin-5-yl)-5-(1,3-thiazol-2-yl)pyrrolidine-2-carboxylic acid, tert-butyl ester

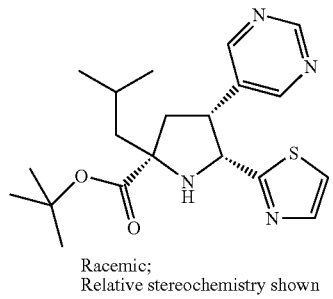

Racemic;
Relative stereochemistry shown

Prepared in a similar manner to that described for Intermediate 2, replacing 2-vinylpyrazine with 5-vinylpyrimidine.* The product was purified by chromatography on silica gel using cyclohexane-ethyl acetate (7:3 v/v) as eluent to provide the title compound as a gum.

* {5-Vinylpyrimidine was synthesized from pyrimidine 5-carboxaldehyde (Peakdale Fine Chemicals) via a Wittig reaction. To the aldehyde (2.72 g, 25.2 mmol) in dioxan (25 mL) and water (0.378 mL) was added (methyl) triphenylphosphonium bromide (9 g, 25.2 mmol) and potassium carbonate (4.35 g, 31.5 mmol). The mixture was heated at reflux for 6 hours. The product can be purified by vacuum distillation or by column chromatography over silica gel after work up.}

MS calcd for $(C_{20}H_{28}N_4O_2S+H)^+$: 389.
MS found (electrospray): $(M+H)^+=389$.

Intermediate 11 rel-(2S,4S,5R)1-(4tert-Butylbenzoyl)-2-isobutyl-4-(pyrimidin-5-yl)-5-(1,3thiazol-2-yl)pyrrolidine-2-carboxylic acid, tert-butyl ester

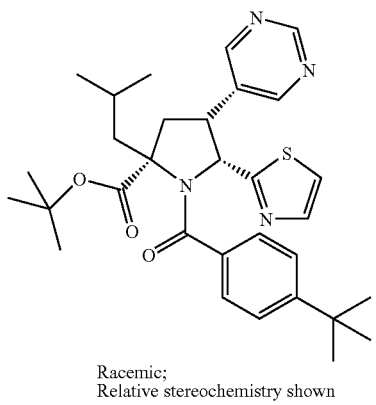

Racemic;
Relative stereochemistry shown

The title compound was prepared from Intermediate 10 in a similar manner to that described for Intermediate 3. The product was purified by chromatography on silica gel using cyclohexane-ethyl acetate (1:1 v/v) as eluent to provide the title compound as a gum.

MS calcd for $(C_{31}H_{40}N_4O_3S+H)^+$: 549.
MS found (electrospray): $(M+H)^+=549$.

Intermediate 12 rel-(2S,4S,5R)-2-Isobutyl-4-(6-methyl-pyridazin-3-yl)-5-(1,3-thiazol-2-yl)pyrrolidine-2-carboxylic acid, tert-butyl ester

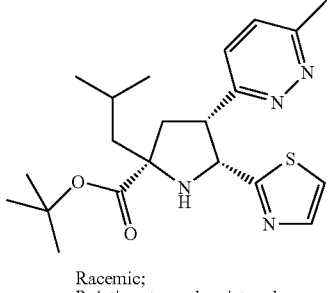

Racemic;
Relative stereochemistry shown

Prepared in a similar manner to that described for Intermediate 2 replacing 2-vinylpyrazine with 3-methyl-6-vinylpyridazine*. The title compound was used without further purification after work up and was isolated as an oil.

*{3-Methyl-6-vinylpyradizine was synthesised in two steps from 6-methyl-3-(2H)-pyridazinone according to the procedures described in Heterocycles, (1994) 38(6), 1273-1286,.}

MS calcd for $(C_{21}H_{30}N_4O_2S+H)^+$: 403.
MS found (electrospray): $(M+H)^+=403$.

Intermediate 13 rel-(2S,4S,5R)-1-(4-tert-Butylbenzoyl)-2-isobutyl-4-(6methyl-pyridazin-2-yl)-5-(1,3-thiazol-2-yl)pyrrolidine-2carboxylic acid, tert-butyl ester

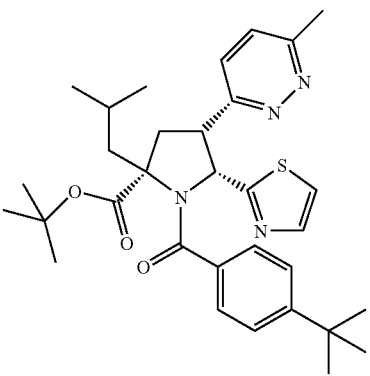

Racemic;
Relative stereochemistry shown

The title compound was prepared from Intermediate 12 in a similar manner to that described for Intermediate 3. The product was purified by chromatography on silica gel using cyclohexane-ethyl acetate (3:1 v/v) as eluent. Further purification by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the eluted fractions by electrospray mass spectroscopy, provided the title compound as a solid.

MS calcd for $(C_{32}H_{42}N_4O_3S+H)^+$: 563.
MS found (electrospray): $(M+H)^+=563$.

Intermediate 14

2-[N-(Pyridin-2-ylmethylene)amino]-4-methylpentanoic acid, tert-butyl ester

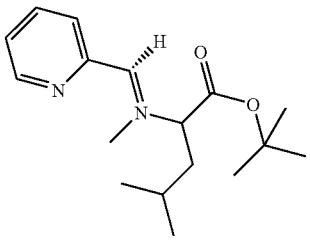

A stirred mixture of 2-amino-4-methylpentanoic acid tert-butyl ester hydrochloride (5.00 g, 22.35 mmol), pyridine-2-carboxaldehyde (2.12 mL, 22.35 mmol) and triethylamine (3.11 mL, 22.35 mmol) in dichloromethane (75 mL) was heated under reflux under nitrogen for 2 hours. The reaction mixture was allowed to cool to room temperature, washed with water and brine, dried over MgSO$_4$ and evaporated to give the title compound as an oil.

$^1$H NMR (CDCl$_3$): δ 8.65 (ddd, 1H), 8.37 (s, 1H), 8.12 (dt, 1H), 7.75 (ddt, 1H), 7.34 (ddd, 1H), 4.05 (dd, 1H), 1.79-1.85 (m, 2H), 1.58 (m, 1H), 1.47 (s, 9H) 0.95 (d, 3H) and 0.91 (d, 3H).

Intermediate 15 rel-(2S,4S,5R)-2-Isobutyl-4-pyrazin-2-yl-5-(pyridin-2-yl)pyrrolidine-2-carboxylic acid, tert-butyl ester

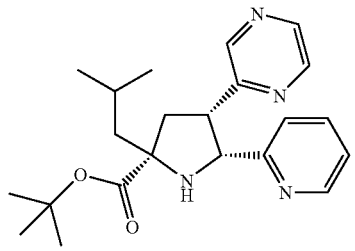

Racemic;
Relative stereochemistry shown

Prepared from Intermediate 14 in a similar manner to that described for Intermediate 2. The product was purified by chromatography on silica gel using 5% methanol in chloroform as eluent to provide the title compound as a solid.

MS calcd for (C$_{22}$H$_{30}$N$_4$O$_2$S+H)$^+$: 383.
MS found (electrospray): (M+H)$^+$=383.

Intermediate 16 rel-(2S,4S,5R)-1-(4-tert-Butylbenzoyl)-2-isobutyl-4-pyrazin-2-yl-5-(pyridin-2-yl)pyrrolidine-2carboxylic acid, tert-butyl ester

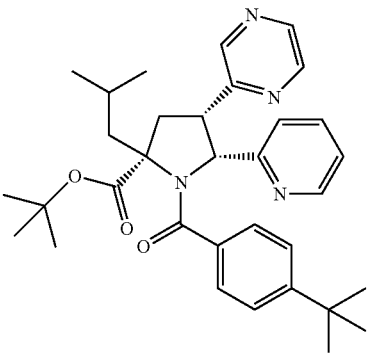

Racemic;
Relative stereochemistry shown

The title compound was prepared from Intermediate 15 in a similar manner to that described for Intermediate 3. The product was purified by SPE (solid phase extraction on silica) using cyclohexane-ethyl acetate (1:1 v/v) as eluent to provide the title compound as an amorphous solid.

$^1$H NMR (CDCl$_3$): δ 8.20 (1H, s), 8.14 (1H, d), 8.12 (1H, d), 8.08 (1H, d), 7.71 (1H, d), 7.44 (1H, dt), 7.04 (2H, d), 6.92 (2H, d), 6.75 (1H, dd),5.54 (1H, d), 4.38 (1H, m), 3.17 (1H, t), 2.46 (1H, dd), 2.38 (1H, dd), 2.17 (1H, dd), 2.10 (1H, m), 1.64 (9H, s), 1.14 (9H, s), 1.14(3H, d), 1.13 (3H, d).

Intermediate 17 rel-(2S,4S,5R)-1-(3-Bromo-4-tert-butylbenzoyl)-2-isobutyl-4-pyrazin-2-yl-5-(pyridin-2-yl)pyrrolidine-2-carboxylic acid, tert-butyl ester

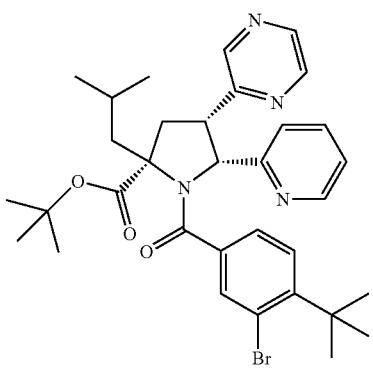

Racemic;
Relative stereochemistry shown

The title compound was prepared from Intermediate 15 in a similar manner to that described for Intermediate 3 replacing 4-tert-butylbenzoyl chloride with 3-bromo-4tert-butylbenzoyl chloride {synthesised from 3-bromo4-tert-butylbenzoic acid (Aust. J. Chem. (1990), 43(5), 807-14)}. The product was purified by SPE (silica, eluting with cyclohexane/EtOAc, as a gradient from 80% to 30% cyclohexane) to provide the title compound as a gum.

$^1$H NMR (CDCl$_3$): δ 8.23 (1H, d), 8.17 (1H, d), 8.14 (1H, m), 8.10 (1H, d), 7.81 (1H, d), 7.53 (1H, dt), 7.18 (1H, d), 6.96 (2H, m), 6.85 (1H, dd), 5.42 (1H, d), 4.37 (1H, m), 3.2 (1H. t), 2.50 (1H, dd), 2.42 (1H, dd), 2.17-2.06 (2H, m), 1.65 (9H, s), 1.35 (9H, s), 1.14 (3H,), 1.13 (3H, d).

Intermediate 18 rel-(2S,4S,5R)-1-(3-Bromo-4-tert-butylbenzoyl)-2-isobutyl-4-pyrazin-2-yl-5-(1,3-thiazol-2-yl)pyrrolidine-2-carboxylic acid, tert-butyl ester

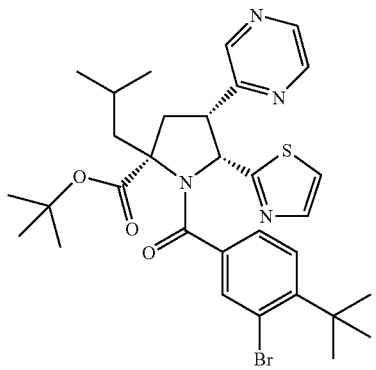

Racemic;
Relative stereochemistry shown

The title compound was prepared from Intermediate 2 in a similar manner to that described for Intermediate 3 replacing 4-tert-butylbenzoyl chloride with 3-bromo-4-tert-butylbenzoyl chloride. The product was purified by SPE using cyclohexane:ethyl acetate (1:1 v/v) as eluent and isolated as a foam.

MS calcd for (C$_{31}$H$_{39}$BrN$_4$O$_3$S+H)$^+$: 627/629.
MS found (electrospray): (M+H)$^+$=627/629.

Intermediate 19 rel-(2S,4S,5R)-1-(3-Bromo-4-tert-butylbenzoyl)-2-isobutyl-4-(methyl-pyrazin-2-yl)-5-(1,3-thiazol-2-yl)pyrrolidine-2-carboxylic acid, tert-butyl ester

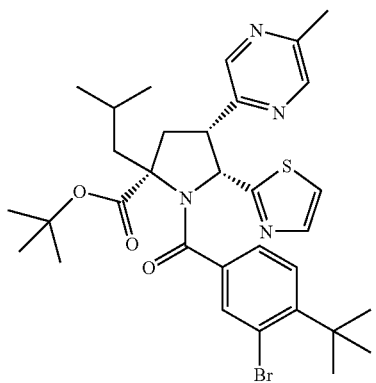

Racemic;
Relative stereochemistry shown

The title compound was prepared from Intermediate 4 in a similar manner to that described for Intermediate 3 replacing 4-tert-butylbenzoyl chloride with 3-bromo-4-tert-butylbenzoyl chloride. The product was purified by chromatography on silica gel using cyclohexane-ethyl acetate (7:3 v/v) as eluent and isolated as a foam.

MS calcd for (C$_{32}$H$_{41}$BrN$_4$O$_3$S+H)$^+$: 641/643.
MS found (electrospray): (M+H)$^+$=641/643.

Intermediate 20

Enantiomer A derived from rel-(2S,4S,5R)-1-(3-Bromo-4-tert-butylbenzoyl)-2-isobutyl-4-(5-methyl-pyrazin-2-yl)-5-(1,3-thiazol-2-yl)pyrrolidine-2-carboxylic acid, tert-butyl ester

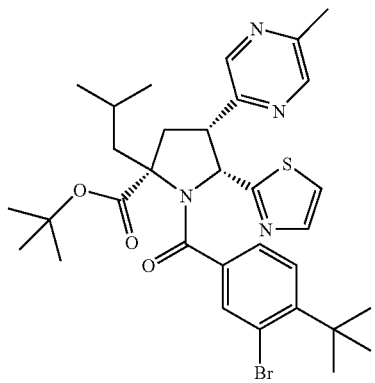

Chiral;
Relative stereochemistry shown

Intermediate 19 was resolved by preparative HPLC on a Chiralpak AD chromatography column using heptane-isopropanol (70:30 v/v) as eluent to afford the individual enantiomers with retention times of 4.0 minutes (Enantiomer A: the title compound) and 6.9 minutes (Enantiomer B) respectively. Enantiomer A was identical by LCMS to the racemic compound described for Intermediate 19.

MS calcd for (C$_{32}$H$_{41}$BrN$_4$O$_3$S+H)$^+$: 641/643.
MS found (electrospray): (M+H)$^+$=641/643.

Intermediate 21

Enantiomer A derived from rel-(2S,4S,5R)-1-(3-Bromo-4-tert-butylbenzoyl)-2-isobutyl-4-(pyrazin-2-yl)-5-(1,3-thiazol-2-yl)pyrrolidine-2-carboxylic acid, tert-butyl ester

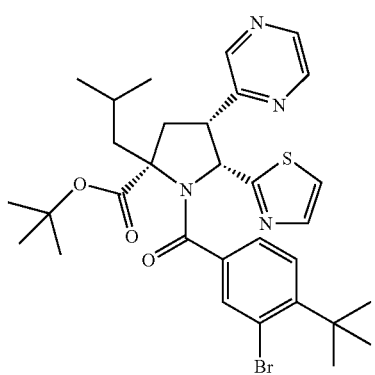

Chiral;
Relative stereochemistry shown

Intermediate 18 was resolved by preparative HPLC on a Chiralpak AD chromatography column using heptane-isopropanol (85:15 v/v) as eluent to afford the individual enantiomers with retention times of 5.9 minutes (Enantiomer A; the title compound) and 10.7 minutes (Enantiomer B) respectively. Enantiomer A was identical by LCMS to the racemic compound described for Intermediate 18.

¹H NMR (CDCl₃): δ 8.26 (3H, m), 7.26 (1H, m), 7.18 (1H, d), 7.13 (1H, d), 7.06 (1H, d), 6.99 (1H, dd), 5.75 (1H, d), 4.33 (1H, m), 3.28 (1H, t), 2.53 (1H, dd), 2.45 (1H, 2.17 (1H, dd), 2.05 (1H, m), 1.61 (9H, s), 1.41 (9H, s), 1.12 (6H, d).

Intermediate 22

Enantiomer A derived from rel-(2S,4S,5R)-1-(4-tert-Butylbenzoyl)-2-isobutyl-4-pyrazin-2-yl-5-(pyridin-2-yl)pyrrolidine-2-carboxylic acid, tert-butyl ester

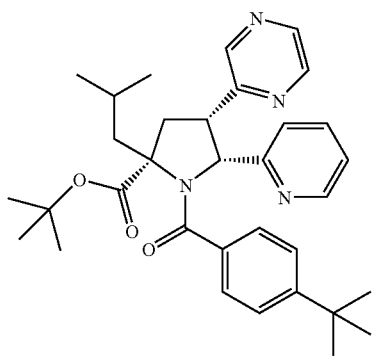

Chiral;
Relative stereochemistry shown

Intermediate 16 was resolved by preparative HPLC on a Chiralpak AD chromatography column using heptane-isopropanol (90:10 v/v) as eluent to afford the individual enantiomers with retention times of 7.5 minutes (Enantiomer A; the title compound) and 10.1 minutes (Enantiomer B) respectively. Enantiomer A was identical by ¹H NMR to the racemic compound described for Intermediate 16.

Intermediate 23

Enantiomer A derived from rel-(2S,4S,5R)-1-(3-Bromo-4-tert-butylbenzoyl)-2-isobutyl-4-pyrazin-2-yl-5-(pyridin-2yl)pyrrolidine2-carboxylic acid, tert-butyl ester

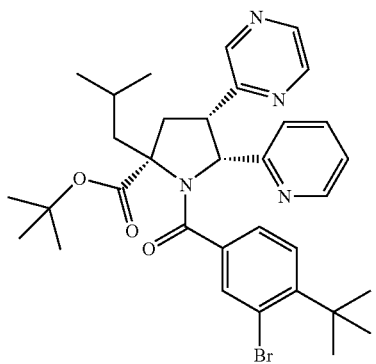

Chiral;
Relative stereochemistry shown

Intermediate 17 was resolved by preparative HPLC on a Chiralpak AD chromatography column using heptane-isopropanol (90:10 v/v) as eluent to afford the individual enantiomers with retention times of 6.5 minutes (Enantiomer A; the title compound) and 10.7 minutes (Enantiomer B) respectively. Enantiomer A was identical by ¹H NMR to the racemic compound described for Intermediate 17.

Intermediate 24 rel-(2S,4S,5R)-1-(4-tert-Butyl-3-chlorobenzoyl)-2-isobutyl-4-(pyrazin-2-yl)-5-1,3-thiazol-2-yl)pyrrolidine-2-carboxylic acid, tert-butyl ester

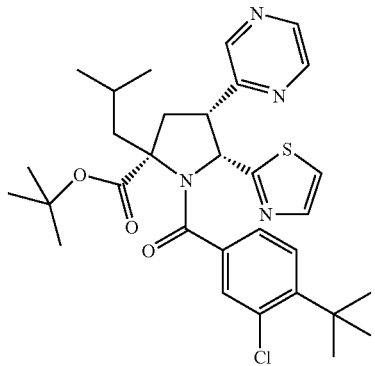

Racemic;
Relative stereochemistry shown

The title compound was prepared from Intermediate 2 in a similar manner to that described for Intermediate 3 replacing 4-tert-butyl-benzoyl chloride with 4-tert-butyl-3-chlorobenzoyl chloride.* The product was purified by SPE using cyclohexane-ethyl acetate (1:1 v/v) as eluent to provide the title compound as a foam.

*{4-tert-Butyl-3chloro-benzoyl chloride was synthesized from 4-tert-butyl-3-chlorobenzoic acid (J. Org. Chem. 30, 1965, 1581-1588)}.

MS calcd for $(C_{31}H_{39}ClN_4O_3S+H)^+$: 583/585.
MS found (electrospray): $(M+H)^+$=583/585.

Intermediate 25

Enantiomer A derived from rel-(2S,4S,5R)-1-(4-tert-Butyl-3-chloro benzoyl)-2-isobutyl-4-(pyrazin-2-yl)-5-(1,3-thiazol-2-yl)pyrrolidine-2-carboxylic acid, tert-butyl ester

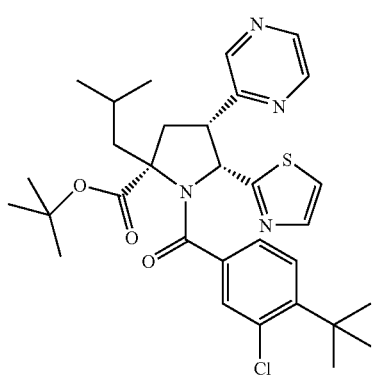

Chiral;
Relative stereochemistry shown

Intermediate 24 was resolved by preparative HPLC on a Chiralpak AD chromatography column using heptane-ethanol (95:5 v/v) as eluent to afford the individual enantiomers with retention times of 8.9 minutes (Enantiomer A, the title compounds and 13.9 minutes (Enantiomer B) respectively.

Enantiomer A was identical by ¹H NMR to the racemic compound described for Intermediate 24.

¹H NMR (CDCl₃): δ 8.26 (3H, m), 7.25 (1H, d), 7.18 (1H, d), 7.05 (1H, d), 6.93 (2H, m). 5.77 (1H, d), 4.34 (1H, m), 3.29 (1H, t), 2.52 (1H, dd), 2.45 (1H, dd), 2.18 (1H, dd), 2.05 (1H, m), 1.60 (9H, s), 1.38 (9H, s), 1.12 (6H, d).

Intermediate 26 rel-(2S,4S,5R)-1-(4-tert-Butyl-3-methoxybenzoyl)-2-isobutyl-4-(pyrazin-2-yl)-5-(1,3-thiazol-2-yl)pyrrolidine-2-carboxylic acid, tert-butyl ester

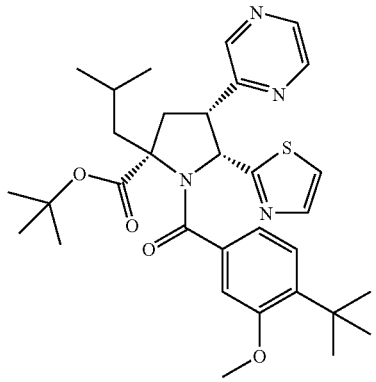

Racemic;
Relative stereochemistry shown

The title compound was prepared from Intermediate 2 in a similar manner to that described for Intermediate 3 replacing 4-tert-butyl-benzoyl chloride with 4-tert-butyl-3-methoxybenzoyl chloride.* The product was purified by SPE using cyclohexane-ethyl acetate (1:2 v/v) as eluent and isolated as a foam.

*{Synthesized from 4-tert-butyl-3-methoxybenzoic acid (J. Org. Chem, 26, 1961, 1732-1737)}¹H NMR (CDCl₃): δ 8.25 (3H, m), 7.18 (1H, d), 7.12 (1H, d), 7.02 (1H, d), 6.71 (1H, dd), 6.38 (1H, d), 5.82 (1H, d), 4.33 (1H, m), 3.54 (3H, s), 3.29 (1H, t), 2.52 (1H, dd), 2.47 (1H, dd), 2.20 (1H, dd), 2.06 (1H, m), 1.60 (9H, s), 1.26 (9H, s), 1.13 (6H, d).

Intermediate 27

Enantiomer A derived from rel-(2S,4S,5R)-1-(4-tert-Butyl-3-methoxybenzoyl)-2-isobutyl-4-(pyrazin-2-yl)-5-(1,3-thiazol-2-yl)pyrrolidine-2-carboxylic acid, tert-butyl ester

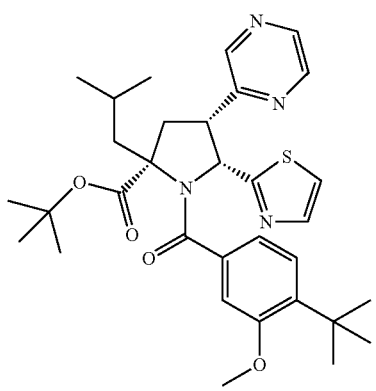

Chiral;
Relative stereochemistry shown

Intermediate 26 was resolved by preparative HPLC on a Chiralpak AD chromatography column using heptane-isopropanol (85:15 v/v) as eluent to afford the individual enantiomers with retention times of 8.5 minutes (Enantiomer A; the title compound) and 13.8 minutes (Enantiomer A) respectively. Enantiomer A was identical by ¹H NMR to the racemic compound described for Intermediate 26.

Intermediate 28

2-[N-(1,3-Benzothiazol-2-ylmethylene)amino]-4methylpentanoic acid, tert-butyl ester

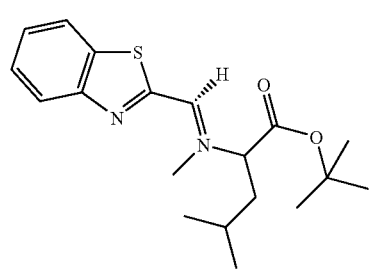

Prepared in a similar manner to that described for Intermediate 14 replacing pyridine-2-carboxaldehyde with 1,3-benzothiazole-2-carboxaldehyde. The title compound was isolated as an oil.

¹H NMR(CDCl₃): δ 8.56 (s, 1H ), 8.10 (d, 1H), 7.93 (d, 1H), 7.54-7.44 (m, 2H), 4.16 (dd, 1H), 1.93-1.78 (m, 2H), 1.66-1.53 (m, 1H), 1.48 (s, 9H), 0.97 (d, 3H) and 0.92 (d, 3H).

Intermediate 29 rel-(2S,4S,5R)-2-Isobutyl-4-pyrazin-2-yl-5-(1,3-benzothiazol2-yl)pyrrolidine-2-carboxylic acid, tert-butyl ester

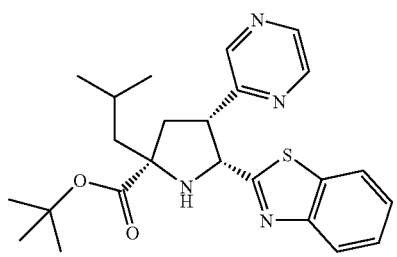

Racemic;
Relative stereochemistry shown

Prepared in a similar manner to that described for Intermediate 2, replacing Intermediate 1 with Intermediate 28. After stirring overnight at room temperature, the reaction was heated at reflux for 9 hours. The product was purified by chromatography on silica gel using cyclohexane-ethyl acetate (1:1 v/v) as eluent followed by trituration with cyclohexane to provide the title compound.

MS calcd for $(C_{24}H_{30}N_4O_2S+H)^+$: 439.

MS found (electrospray): $(M+H)^+$=439.

Intermediate 30

Enantiomer A derived from rel-(2S,4S,5R)-1-(3-bromo-4-tert-butylbenzoyl)-2-isobutyl-4-pyrazin-2-yl-5-(1,3-benzothiazol-2-yl)pyrrolidine-2-carboxylic acid, tert-butyl ester

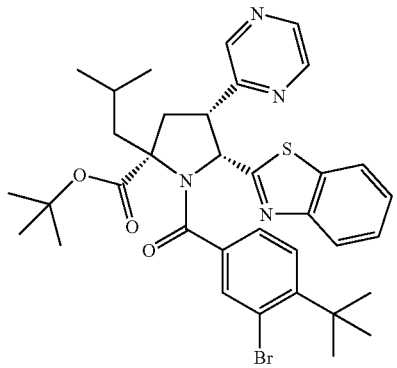

Chiral;
Relative stereochemistry shown

Stage A: The racemic compound was prepared from Intermediate 29 in a similar manner to that described for Intermediate 3 replacing 4-tert-butyl-benzoyl chloride with 3-bromo-4-tert-butylbenzoyl chloride. The reaction was heated at 40° C. for 7 hours and then stirred at room temperature overnight The product was purified by chromatography over silica gel using cyclohexane-ethyl acetate (1:1 v/v) as eluent to provide the racemic product.

MS calcd for $(C_{35}H_{41}BrN_4O_3S+H)^+$: 677/679.
MS found (electrospray): $(M+H)^+=677/679$.

Stage B: The racemic material was then resolved by preparative HPLC on a Chiralpak AD chromatography column using heptane-isopropanol (90:10 v/v) as eluent to afford the individual enantiomers with retention times of 6.6 minutes (Enantiomer A, the title compound) and 7.9 minutes (Enantiomer B) respectively. Enantiomer A was identical by LCMS to the racemic material.

MS calcd for $(C_{35}H_{41}BrN_4O_3S+H)^+$: 677/679.
MS found (electrospray): $(M+H)^+=677/679$.

Intermediate 31

Enantiomer A derived from rel-(2S,4S,5R)-1-(4-tert-butylbenzoyl)-2-isobutyl-4-pyrazin-2-yl-5-(1,3-benzothiazol-2-yl)pyrrolidine-2-carboxylic acid, tert-butyl ester

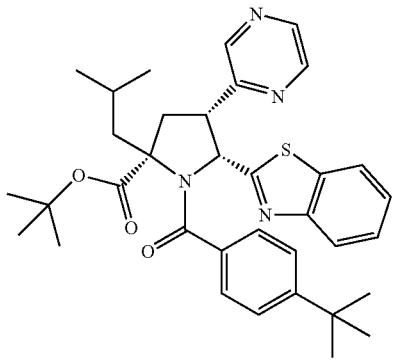

Chiral;
Relative stereochemistry shown

Stage A: The racemic compound was prepared from Intermediate 29 in a similar manner to that described for Intermediate 3. The reaction was heated at 40° C. for 7 hours. The product was purified by chromatography over silica gel using cyclohexane-ethyl acetate (1:1 v/v) as eluent to provide the racemic compound.

MS calcd for $(C_{35}H_{42}N_4O_3S+H)^+$: 599.
MS found (electrospray): $(M+H)^+=599$.

Stage B: The racemic material was then resolved by preparative HPLC on a Chiralpak AD chromatography column using heptane-isopropanol (90:10 v/v) as eluent to afford the individual enantiomers with retention times of 8 minutes (Enantiomer A; the title compound) and 10 minutes (Enantiomer B) respectively. Enantiomer A was identical by LCMS to the racemic material.

MS calcd for $(C_{35}H_{42}N_4O_3S+H)^+$: 599.
MS found (electrospray): $(M+H)^+=599$.

Intermediate 32 rel-(2S,4S,5R-2-Isobutyl-4-pyridazin-3-yl-5-(1,3-thiazol-2-yl)pyrrolidine-2-carboxylic acid, tert-butyl ester

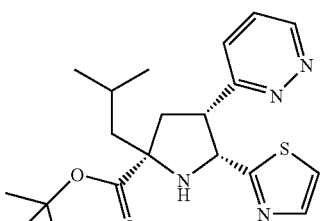

Racemic;
Relative stereochemistry shown

Prepared in a similar manner to that described for Intermediate 2, replacing 2-vinylpyrazine with 3-vinylpyridazine.* The product was purified by SPE eluting with dichloromethane, then a gradient of 1-10% methanol in dichloromethane-methanol, then methanol, to provide the title compound as an oil.

*{3-Vinylpyridazine was synthesized in two steps from 3-(2H)-pyridazinone according to the procedures in Heterocycles (1994) 38-(6), 1273-1286}.

MS calcd for $(C_{20}H_{28}N_4O_2S+H)^+$: 389.
MS found (electrospray): $(M+H)^+=389$.

Intermediate 33 rel-(2S,4S,5R)-1-(4-tert-Butylbenzoyl)-2-isobutyl-4-pyridazin-3-yl-5-(1,3-thiazol-2-yl)pyrrolidine-2-carboxylic acid, tert-butyl ester

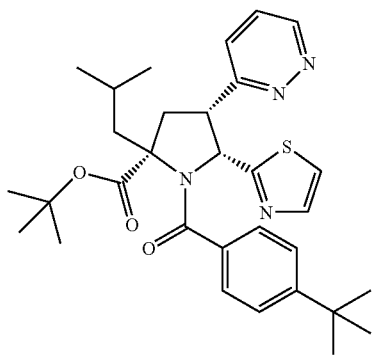

Racemic;
Relative stereochemistry shown

This was prepared from Intermediate 32 in a similar manner to that described for Intermediate 3. The product was purified by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the eluted fractions by electrospray mass spectroscopy. This provided the title compound as a solid.

MS calcd for $(C_{31}H_{40}N_4O_3S+H)^+$: 549.
MS found (electrospray): $(M+H)^+=549$.

Intermediate 34 rel-(2S,4S,5R)-2-Isobutyl-4-quinoxalin-2-yl-5-(1,3-thiazol-2-yl)pyrrolidine-2-carboxylic acid, tert-butyl ester

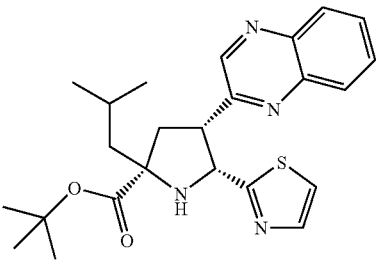

Racemic;
Relative stereochemistry shown

Prepared in a similar manner to that described for Intermediate 2, replacing 2-vinylpyrazine with 2-vinylquinoxaline.* The product was purified by SPE using cyclohexane:ethylacetate (2:1 v/v) as eluent to provide the title compound as an oil.
*{2-Vinylquinoxaline was synthesized from quinoxaline-2-carboxaldehyde using the procedure described in Intermediate 10 for 5-vinylpyrimidine}.

MS calcd for $(C_{24}H_{30}N_4O_2S+H)^+$: 439.
MS found (electrospray): $(M+H)^+=439$.

Intermediate 35 rel-(2S,4S,5R)-1-(4-tert-Butylbenzoyl)-2-isobutyl-4-quinoxalin-2-yl-5-(1,3-thiazol-2-yl)pyrrolidine-2-carboxylic acid, tert-butyl ester

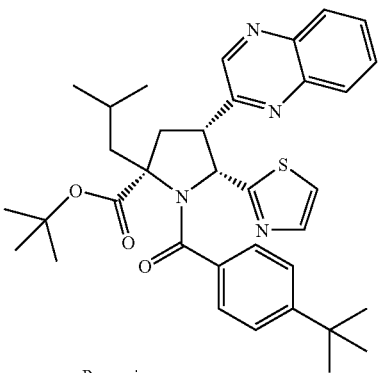

Racemic;
Relative stereochemistry shown

This was prepared from Intermediate 34, in a similar manner to that described for Intermediate 3. The product was purified by SPE using cyclohexane-ethyl acetate (9:1 v/v) as eluent to provide the title compound as a foam.

MS calcd for $(C_{35}H_{42}N_4O_3S+H)^+$: 599.
MS found (electrospray): $(M+H)^+=599$.

Intermediate 36 rel-(2S,4S,5R)-2-Isobutyl-4-(4-trifluoromethyl-pyridin-2-yl)-5-(1,3thiazol-2-yl)pyrrolidine-2-carboxylic acid, tert-butyl ester

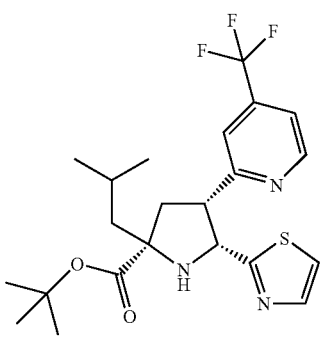

Racemic;
Relative stereochemistry shown

Prepared in a similar manner to that described for Intermediate 2, replacing 2-vinylpyrazine with 2-vinyl-4-(trifluoromethyl)pyridine.* The product was purified by SPE using diethyl ether as eluent to provide the title compound as an oil.
*{2-Vinyl-4-trifluoromethyl)pyridine was synthesized from 2-chloro-4-(trifluoromethyl)pyridine according to the procedure in Heterocycles (1994) 38(6), 1273-1286}.

MS calcd for $(C_{22}H_{28}F_3N_3O_2S+H)^+$: 456.
MS found (electrospray): $(M+H)^+=456$.

Intermediate 37 rel-(2S,4S,5R)-1-(4-tert-Butylbenzoyl)-2-isobutyl-4-(4-trifluoromethylpyridin-2-yl)-5-(1,3-thiazol-2-yl)pyrrolidine-2-carboxylic acid, tert-butyl ester

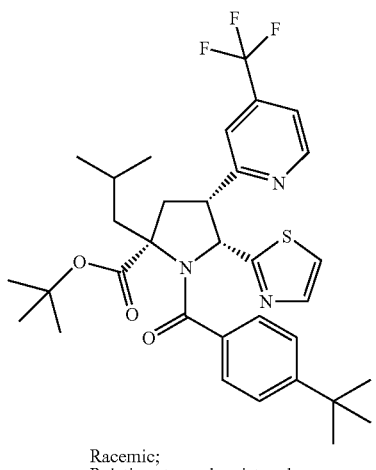

Racemic;
Relative stereochemistry shown

This was prepared from Intermediate 36, in a similar manner to that described for Intermediate 3. The product was purified by chromatography on silica gel using cyclohexane:ethyl acetate (9:1 v/v) as eluent to provide the title compound as a gum.

MS calcd for $(C_{33}H_{40}F_3N_3O_3S+H)^+$: 616.
MS found (electrospray): $(M+H)^+=616$.

Intermediate 38 rel-(2S,4S,5R)-1(4-tert-Butyl3methylbenzoyl)-2-isobutyl-4-(pyrazin-2-yl)-5-(1,3-thiazol-2-yl)pyrrolidine-2carboxylic acid, tert-butyl ester

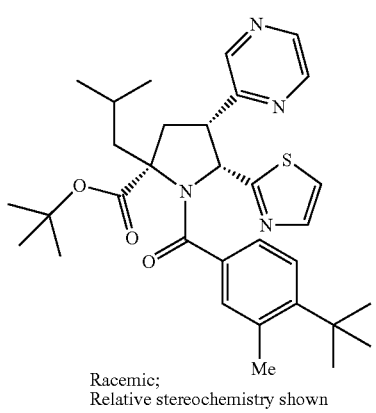

Racemic;
Relative stereochemistry shown

This was prepared from Intermediate 2, in a similar manner to that described for Intermediate 3 replacing 4-tert-butyl-benzoyl chloride with 4-tert-butyl-3-methylbenzoyl chloride (prepared from Intermediate 39). The reaction was heated at 40° C. for 6 hours. The product was purified by SPE using a gradient of cyclohexane-ethyl acetate (95:5-50:50 v/v) as eluent to provide the title compound as a gum.

MS calcd for $(C_{32}H_{42}N_4O_3S+H)^+$: 563.
MS found (electrospray): $(M+H)^+=563$.

Intermediate 39

4-tert-Butyl-3-methyl-benzoic acid

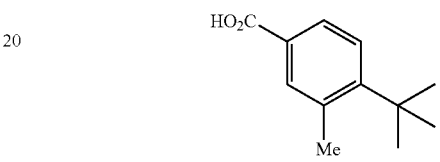

To 3-bromo-4-tert-butylbenzoic acid (500 mg, 1.94 mmol) (Aust.J.Chem. (1990), 43(5), 807-14) in toluene (10 mL) was added N,N-dimethylformamide-di-tert-butyl acetal (1.86 mL, 7.76 mmol). The mixture was heated at 110° C. for 24 hours. More N,N-dimethylformamide -di-tert-butyl acetal (2 mL, 8.38 mmol) was added and the reaction was heated at reflux for a further 24 hours. The solvent was evaporated in vacuo and the residue was purified by SPE (silica, eluting with a gradient of ether in cyclohexane, 1% to 3%) to give a colourless oil (89%). The oil was dissolved in anhydrous THF (4 mL) and cooled to −78° C. under nitrogen. tert-Butyllithium (1.7M in pentane, 0.55 mL, 0.94 mmol) was added dropwise, maintaining the temperature at −70° C. After 15 min., methyl iodide (0.53 mL, 8.45 mmol) was added dropwise, maintaining the temperature at below −70° C. The reaction mixture was allowed to attain room temperature over 3 hours. Saturated ammonium chloride solution was added and the mixture extracted with diethyl ether. The organic extract was dried (MgSO$_4$) and the solvent was evaporated in vacuo to give a brown oil. This was purified by reverse phase HPLC on a C$_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy, to give a colourless oil (38%). This oil (80 mg, 0.32 mmol) was subsequently treated with trifluoroacetic acid (5 mL) and the reaction was stirred at room temperature for 18 hours. The solvent was evaporated in vacuo and the residue was azeotroped with toluene to give the title compound as solid.

MS calcd for $(C_{12}H_{16}O_2+H)^+$: 191.
MS found (electrospray): $(M-H)^+=191$.

Intermediate 40

2-[N-(2-Chloro-1,3-thiazol-5-ylmethylene)amino]-4methylpentanoic acid, tert-butyl ester

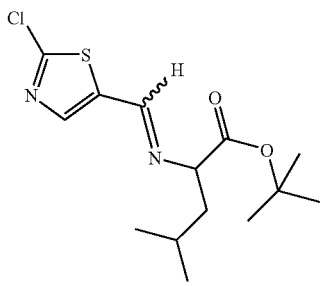

Prepared in a similar manner to that described for Intermediate 1, replacing 1,3-thiazole-2-carboxaldeyde with 2-chloro-1,3-thiazole-5-carboxaldehyde.

$^1$H NMR (CDCl$_3$): δ 8.31 (s, 1H), 7.74 (d, 1H), 3.96 (dd, 1H), 1.78-1.74 (m, 2H), 1.61-1.58 (m, 1H), 1.46 (s, 9H), 0.94 (d, 3H) and 0.89 (d, 3H).

Intermediate 41 rel-(2S,4S,5R)-2-Isobutyl-4-pyrazin-2-yl-5-(2-chloro-1,3thiazol-5-yl)pyrrolidine-2-carboxylic acid, tert-butyl ester

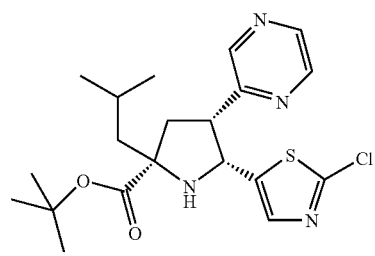

Racemic; Relative stereochemistry shown

Prepared in a similar manner to that described for Intermediate 2, replacing Intermediate 1 with Intermediate 40.
MS calcd for (C$_{20}$H$_{27}$ClN$_4$O$_2$S+H)$^+$: 423/425.
MS found (electrospray): (M+H)$^+$=423/425.

Intermediate 42

2-Vinyl-6methylpyrazine

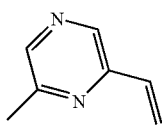

To a solution of 2,6-dimethylpyrazine (5.0 g, 46.2 mmol) in carbon tetrachloride (150 mL) was added N-chlorosuccinimide (6.17 g, 46.2 mmol) and AIBN (152 mg) and the mixture stirred at 85° C. under nitrogen for 6 hours. The mixture was coled in an ice bath, the solid filtered off and washed with cold carbon tetrachloride. The combined filtrates were evaporated in vacuo and the residue purified by silica chromatography using a Biotage cartridge, eluting with cyclohexane/ethyl acetate (1:1 v/v). Fractions containing 2-chloromethyl-6-methylpyrazine were combined and further purified by a second silica column eluting with dichloromethane/ethyl acetate (9:1 v/v). To 2-chloromethyl-6-methylpyrazine (1.81 g, 12.6 mmol) in dry DMF (100 mL) was added triphenylphosphine (3.97 g, 15.1 mmol) and the mixture heated at 70° C. for 6 hours. After standing at room temperature for 3 days, the resulting precipitate was isolated by filtration, dissolved in methanol, evaporated and triturated with ether to afford 2-triphenylphosphoniummethyl-6-methylpyrazine chloride. To 2-triphenylphosphoniummethyl-methylpyrazine chloride (2.16 g, 5.3 mmol) and paraformaldehyde (1.6 g, 53 mmol) in dry methanol (100 mL) was added triethylamine (1.85 mL, 13.3 mmol) and the mixture heated under reflux for 5.5 hours. After cooling, the solvent was removed in vacuo, the residue taken up in ethyl acetate (80 mL) and washed with water (3×80 mL). The residue was purified by silica column chromatography, eluting with cyclohexane/ethyl acetate (1:1) to give the title compound as an oil $^1$H NMR (CDCl$_3$): δ 8.40 (s, 1H), 8.31 (s, 1H), 6.80 (dd, 1H), 6.33 (d, 1H), 5.59 (d, 1H), 2.56 (s, 3H).

Intermediate 43 rel-(2S,4S,5R)-2-Isobutyl-4-(6methyl-pyrazin-2-yl)-5-(1,3thiazol-2-yl)pyrrolidine-2-carboxylic acid, tert-butyl ester

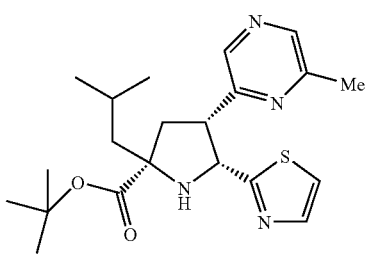

Racemic; Relative stereochemistry shown

Prepared in a similar manner to that described for Intermediate 2, replacing 2-vinylpyrazine with 2-vinyl-6-methylpyrazine.
MS calcd for (C$_{21}$H$_{30}$N$_4$O$_2$S+H)$^+$: 403.
MS found (electrospray): (M+H)$^+$=403.

Intermediate 44

2-[N-(Phenylmethylene)amino]-4-methylpentanoic acid, tert-butyl ester

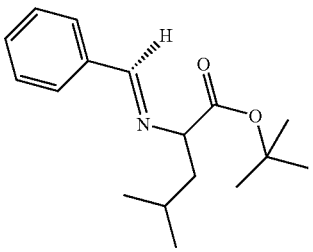

Prepared in a similar manner to that described for Intermediate 1, replacing 1,3-thiazole-2-carboxaldeyde with benzaldehyde.

$^1$H NMR (CDCl$_3$): δ 8.29 (s, 1H), 7.83-7.72 (m, 2H), 7.48-7.32 (m, 3H), 4.00-3.88 (m, 1H), 1.88-1.73 (m, 2H), 1.68-1.53 (m, 1H), 1.48 (s, 9H), 0.95 (d, 3H) and 0.90 (d, 3H).

Intermediate 45 rel-(2S,4S,5R)-2-Isobutyl-4pyrazin-2-yl-5-phenyl-pyrrolidine-2carboxylic acid, tert-butyl ester

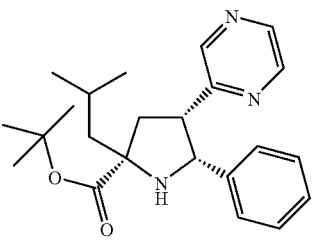

Racemic;
Relative stereochemistry shown

Prepared in a similar manner to that described for Intermediate 2, replacing Intermediate 1 with Intermediate 44.
MS calcd for (C$_{23}$H$_{31}$N$_3$O$_2$+H)$^+$: 382.
MS found (electrospray): (M+H)$^+$=382.

Intermediate 46

2-[N-(Methylmethylene)amino]-4methylpentanoic acid, tert-butyl ester

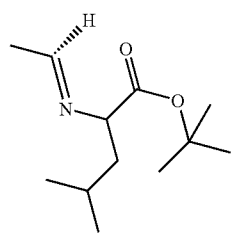

A solution of leucine tert-butyl ester (2.0 g, 8.9 mmol) and acetaldehyde (999 ul, 17.9 mmol) was stirred at room temperature for 5 minutes. Anhydrous sodium sulphate was added and the mixture stirred at room temperature for 18 hours. The solid was removed by filtration and the solvent evaporated in vacuo to afford the title compound as an oil.

$^1$H NMR (CDCl$_3$): δ 7.72 (q, 1H), 3.70 (dd, 1H), 2.02 (d, 3H), 1.71-1.64 (m, 2H), 1.46 (m, 10H), 0.93 (d, 3H) and 0.85 (d, 3H).

Intermediate 47 rel-(2S,4S,5S)-2-Isobutyl-4-pyrazin-2-yl-5-methyl-pyrrolidine-2-carboxylic acid, tert-butyl ester

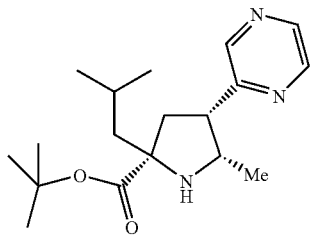

Racemic;
Relative stereochemistry shown

Prepared in a similar manner to that described for Intermediate 2, replacing triethylamine with 1,8-diazabicyclo[5,4,0]udec-7-ene (DBU) and Intermediate 1 with Intermediate 46.
MS calcd for (C$_{18}$H$_{29}$N$_3$O$_2$+H)$^+$: 320.
MS found (electrospray): (M+H)$^+$=320.

Intermediate 48

2-[N-(Pyridin-3-ylmethylene)amino]-4methylpentanoic acid, tert-butyl ester

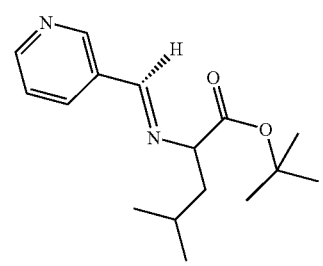

Prepared in a similar manner to that described for Intermediate 1, replacing 1,3-thiazole-2-carboxaldehyde with 3-pyridine carboxaldehyde.

$^1$H NMR (CDCl$_3$): δ 8.88 (d, 1H), 8.66 (dd, 1H), 8.33 (s, 1H), 8.19 (dt, 1H), 7.35 (dd, 1H), 4.00 (dd, 1H), 1.85-1.78 (m, 2H), 1.64-1.52 (m, 1H), 1.48 (s, 9H), 0.96 (d, 3H), and 0.91 (d, 3H).

Intermediate 49 rel-(2S,4S,5R)-2-Isobutyl-4-pyrazin-2-yl-5-(pyridin-3-yl)-pyrrolidine-2-carboxylic acid, tert-butyl ester

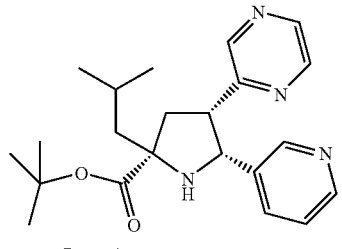

Racemic;
Relative stereochemistry shown

Prepared in a similar manner to that described for Intermediate 2, replacing Intermediate 1 with Intermediate 48.
MS calcd for $(C_{22}H_{30}N_4O_2+H)^+$: 383.
MS found (electrospray): $(M+H)^+=383$.

Intermediate 50

2-[N-(Thiophen-2-ylmethylene)amino]-4methylpentanoic acid, tert-butyl ester

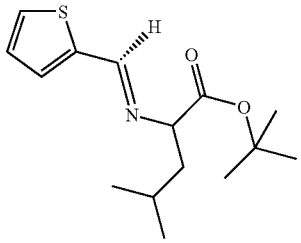

Prepared in a similar manner to that described for Intermediate 1, replacing 1,3-thiazole-2-carboxaldehyde with 2-thiophene carboxaldehyde.
$^1$H NMR (CDCl$_3$): δ 8.38 (s, 1H), 7.42 (d, 1H), 7.35 (d, 1H), 7.08 (dd, 1H), 3.94 (dd, 1H), 1.86-1.71 (m, 2H), 1.64-1.55 (m, 1H), 1.46 (s, 9H), 0.94 (d, 3H) and 0.89 (d, 3H).

Intermediate 51 rel-(2S,4S,5R)-2-Isobutyl-4-(pyrazin-2-yl)-5-(thien-2-yl)pyrrolidine-2-carboxylic acid, tert-butyl ester

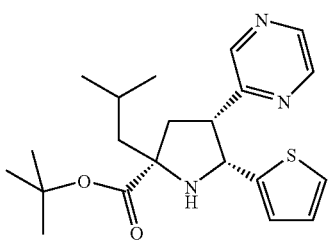

Racemic;
Relative stereochemistry shown

Prepared in a similar manner to that described for Intermediate 2, replacing Intermediate 1 with Intermediate 50.
MS calcd for $(C_{21}H_{29}N_3O_2S+H)^+$: 388.
MS found (electrospray): $(M+H)^+=388$.

Intermediate 52

2-[N-(1,3-Thiazol-4-ylmethylene)amino]-4-methylpentanoic acid, tert-butyl ester

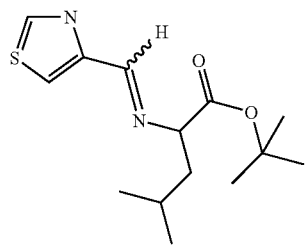

Prepared in a similar manner to that described for Intermediate 1, replacing 1,3-thiazole-2-carboxaldehyde with 1,3-thiazole 4carboxaldehyde (Intermediate 57).
$^1$H NMR (CDCl$_3$): δ 8.84 (s, 1H), 8.49 (d, 1H), 8.01 (s, 1H), 4.00 (dd, 1H), 1.90-1.70 (m, 2H), 1.64-1.56 (m, 1H), 1.47 (s, 9H), 0.96 (d, 3H) and 0.91 (d, 3H).

Intermediate 53 rel-(2S,4S,5R)-2-Isobutyl-4-(pyrazin-2-yl)-5-(1,3-thiazol-4-yl)pyrrolidine-2-carboxylic acid, tert-butyl ester

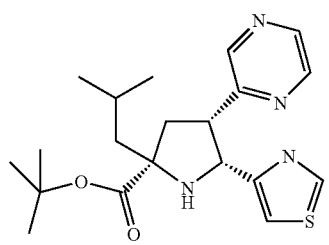

Racemic;
Relative stereochemistry shown

Prepared in a similar manner to that described for Intermediate 2, replacing Intermediate 1 with Intermediate 52.
MS calcd for $(C_{20}H_{28}N_4O_3S+H)^+$: 389.
MS found (electrospray): $(M+H)^+=389$.

Intermediate 54

2-Dimethylamino-1,3-thiazole-4-carboxaldehyde

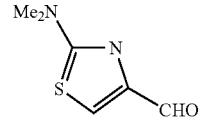

To a solution of 2-aminothiazole (30 g, 0.3 mmol) in conc. hydrochloric acid (150 mL) at 0° C. was added dropwise a saturated solution of sodium nitrite (20.7 g) in water. After 75 minutes at 0° C., cuprous chloride (29.7 g) was added portionwise and the mixture stirred at 0° C. for a further 150 minutes. The mixture was neutralised with conc. sodium hydroxide solution and partitioned between diethyl ether and water. The organic phase was washed with brine, dried over sodium sulphate and evaporated in vacuo to afford 2-chlorothiazole as an oil. To a solution of 2-chlorothiazole (15.9 g, 133 mmol) in THF (200 mL) at −74° C. was added n-BuLi (1.6M in hexane, 90 mL). After 10 minutes, a solution of DMF (14 mL) in THF (90 mL) was added and the mixture allowed to attain room temperature over 2 hours. The mixture was then poured slowly into hydrochloric acid (2M, 400 mL), basified with ammonium hydroxide and extracted with dichloromethane (2×300 mL). The combined organic fractions were dried over sodium sulphate and evaporated in vacuo to afford 2chloro-thiazol4-carboxaldehyde as a solid. A mixture of 2chloro-thiazole-4-carboxaldehyde (20 g) in 2.5% aqueous THF (400 mL) and dimethylamine (13 g, 2.5 equiv.) in THF (150 mL) were combined and stirred at room temperature for 16 hours. The solvent was evaporated in vacuo, the residue partitioned between water and dichloromethane and the organic layer dried over sodium sulphate. Evaporation of the solvent afforded the title compound as a solid $^1$H NMR (CDCl$_3$): δ 9.75 (s, 1H), 7.9 (s, 1H), 3.3 (s, 6H).

Intermediate 55

2-[N-(2-Dimethylamino)-1,3-thiazol-4-ylmethylene)amino]-4-methylpentanoic acid, tert-butyl ester

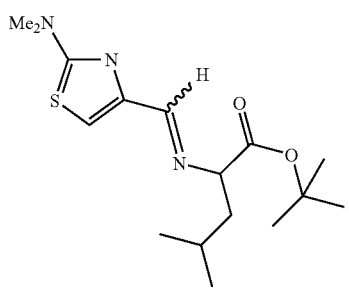

Prepared in a similar manner to that described for Intermediate 1, replacing 1,3-thiazole-2-carboxaldehyde with 2-dimethylamino-1,3-thiazole 4-carboxaldehyde (Intermediate 54).

$^1$H NMR (CDCl$_3$): δ 8.21 (s, 1H), 7.43 (s, 1H), 3.87 (t, 1H), 3.21 (s, 3H), 3.13 (s, 3H), 180-1.70 (m, 2H), 1.64-1.52 (m, 1H), 1.46 (s, 9H), 0.94 (d, 3H) and 0.88 (d, 3H).

Intermediate 56 rel-(2S,4S,5R)-2-Isobutyl-4-(pyrazin-2-yl)-5-(2-dimethylamino-1,3thiazol-4-yl)pyrrolidine-2-carboxylic acid, tert-butyl ester

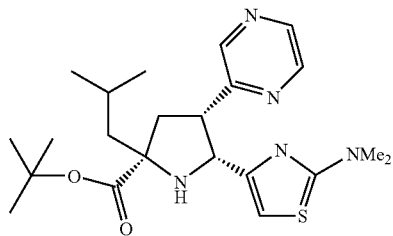

Racemic;
Relative stereochemistry shown

Prepared in a similar manner to that described for Intermediate 2, replacing Intermediate 1 with Intermediate 55.
MS calcd for (C$_{22}$H$_{33}$N$_5$O$_2$S+H)$^+$: 432.
MS found (electrospray): (M+H)$^+$=432.

Intermediate 57

1,3-Thiazole-4-carboxaldehyde

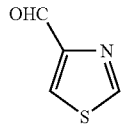

A stirred mixture of 4-chloromethylthiazole (1 g, 5.88 mmol) and hexamine (1.64 g, 11.76 mmol, 2 eq) in 50% acetic acid (10 mL) was heated at reflux for 3 hours. The reaction mixture was allowed to cool for five minutes and then concentrated hydrochloric acid (2.5 mL) was added. The resulting reaction mixture was refluxed for a further five minutes prior to dilution of the reaction mixture with water (50 mL). The resulting reaction mixture was extracted with dichloromethane (6×50 mL). The extracts were combined and washed once with sodium bicarbonate (50 mL), dried over Na$_2$SO$_4$ and evaporated to give the title compound as a gum.

$^1$H NMR (CDCl$_3$): δ 10.14 (s, 1H), 8.93 (s, 1H), 8.28 (s,1H).

Intermediate 58

2-[N-(1,3-thiazol-2-ylmethylene)amino]-succinic acid, 1-tert-butyl ester, 4-benzyl ester.

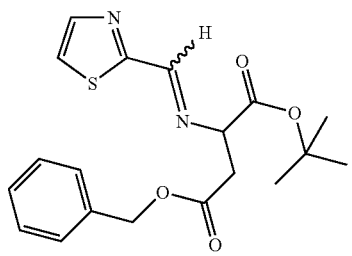

Prepared in a similar manner to that described for Intermediate 1, replacing 2-amino4-methyl-pentanoic acid, tert-butyl ester hydrochloride with 2-amino-succinic acid, 1 tert-butyl ester, 4-benzyl ester.

$^1$H NMR (CDCl$_3$): δ 8.51 (s, 1H), 7.95 (d, 1H), 7.44 (d, 1H), 7.35-7.29 (m, 5H), 5.12 (s, 2H), 4.47 (dd, 1H), 3.15 (dd, 1H), 2.92 (dd, 1H), 1.43 (s, 9H).

Intermediate 59 rel-(2S,4S,5R)-1-(4-tert-Butyl-3-methoxybenzoyl)-2-(2-benzyloxycarbonylmethyl)-4-(pyrazin-2-yl)-5-(1,3-thiazol-2-yl)pyrrolidine-2-carboxylic acid, tert-butyl ester

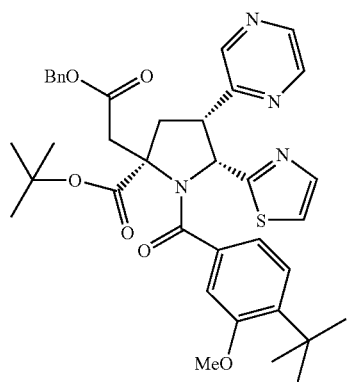

Racemic;
Relative stereochemistry shown

Prepared in a similar manner to that described for Intermediate 3, replacing Intermediate 2 with Intermediate 66 and 4-tert-butyl-benzoyl chloride with 3-tert-butyl-4-methoxybenzoyl chloride.

MS calcd for (C$_{37}$H$_{42}$N$_4$O$_6$S+H)$^+$: 671.
MS found (electrospray): (M+H)$^+$=671.

Intermediate 60 rel-(2S,4S,5R)-1-4-tert-Butyl-3-methoxybenzoyl)-2-(carboxymethyl)-4-(pyrazin-2-yl)-5-(1,3-thiazol-2-yl)pyrrolidine-2carboxylic acid, tert-butyl ester

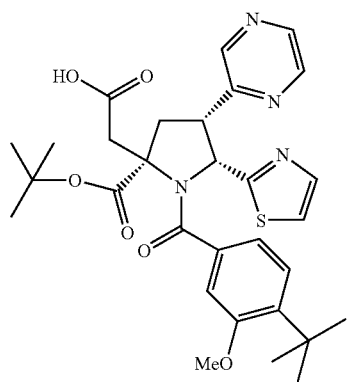

Racemic;
Relative stereochemistry shown

To a solution of Intermediate 59 (0.696 mg, 1.04 mmol) in ethanol (45 mL) was added 10% palladium on carbon catalyst (100 mg) followed by a solution of ammonium formate (2 g) in ethanol (40 mL). The mixture was heated under reflux for 2 hours. The catalyst was removed by filtration and washed with ethanol. The filtrate was evaporated to dryness, and partitioned between water and ethyl acetate. The organic phase was dried over sodium sulphate and evaporated to afford the title compound as a solid.

MS calcd for (C$_{30}$H$_{36}$N$_4$O$_6$S+H)$^+$: 581.
MS found (electrospray): (M+H)$^+$=581.

Intermediate 61 rel-(2S,4S,5R)-1-(4-tert-Butyl-3-methoxybenzoyl)-2-(aminocarbonylmethyl)-4-(pyrazin-2-yl)-5-(1,3thiazol-2-yl)pyrrolidine-2-carboxylic acid, tert-butyl ester

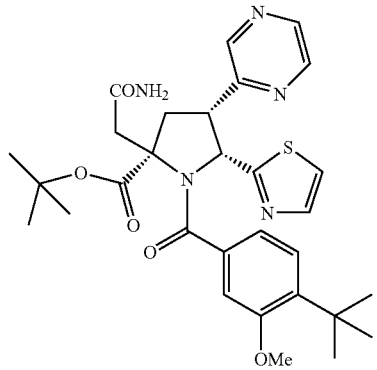

Racemic;
Relative stereochemistry shown

The tile compound was prepared as a solid from Intermediate 60, in a similar manner to that described in Example 20. The crude product was purified by partitioning between ethyl acetate and water, evaporation of the organic fraction, and then by SPE chromatography over silica with methanol/ethyl acetate (1:10) as eluent MS calcd for (C$_{30}$H$_{37}$N$_5$O$_5$S+H)$^+$: 580.
MS found (electrospray): (M+H)$^+$=580.

Intermediate 62 rel-(2S,4S,5R)-1-(4-tert-Butyl-3-methoxybenzoyl)-2-methylaminocarbonylmethyl)-4-(pyrazin-2-yl)-5-(1,3-thiazol-2-yl)pyrrolidine-2-carboxylic acid, tert-butyl ester

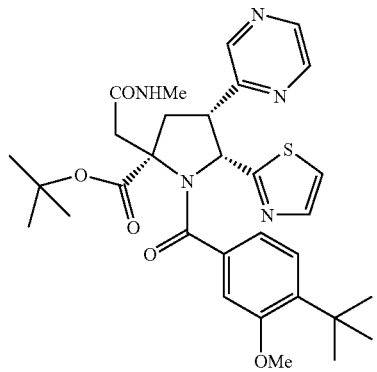

Racemic;
Relative stereochemistry shown

The title compound was prepared as a solid from Intermediate 60 and methylamine hydrochloride, in a similar manner to that described in Example 20. The crude product was purified by partitioning between ethyl acetate and water, evaporation of the organic fraction and then by SPE chromatography over silica with methanol/ethyl acetate (1:20) as eluent.

MS calcd for $(C_{31}H_{39}N_5O_5S+H)^+$: 594.
MS found (electrospray): $(M+H)^+$=594.

Intermediate 63

Enantiomer A of rel-(2S,4S,5R)-1-(4-tert-butyl-3-chlorobenzoyl)-2-isobutyl-4-pyrazin-2-yl-5-(pyridin-2yl)pyrrolidine-2-carboxylic acid, tert-butyl ester

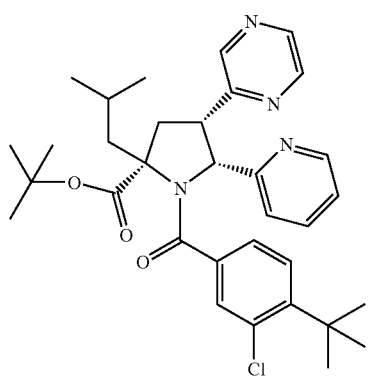

Chiral;
Relative stereochemistry shown

Stage A: Intermediate 15 was reacted with 4-tert-butyl-3-chlorobenzoyl chloride in a similar manner to that described in the preparation of Intermediate 3, to afford rel-2S,4S,5R)-1-(4-tert-butyl-3-chlorobenzoyl)-2-isobutyl-4-pyrazin-2-yl-5-(pyridin-2-yl)pyrrolidine-2-carboxylic acid, tert-butyl ester.

MS calcd for $(C_{29}H_{33}ClN_4O_3S+H)^+$: 521/523.
MS found (electrospray): $(M+H)^+$=521/523.

Stage B: The racemate from stage A was resolved using a chiralpak AD column and heptane-isopropanol (85:15 v/v) as eluent. The first eluted enantiomer (enantiomer A) was the title compound having identical LCMS to the racemate.

Intermediate 64

2-[N-(3-Phenyl-phenyl)methyleneamino]-4-methyl-pentanoic acid, tert-butyl ester

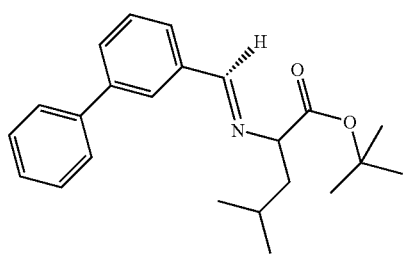

Prepared in a similar manner to that described for Intermediate 1, replacing 1,3-thiazole-2-carboxaldehyde with 3-phenyl-benzaldehyde.

$^1$H NMR (CDCl$_3$): δ 8.35 (s, 1H), 8.01 (s, 1H), 7.76 (d, 1H), 7.67-7.59 (m, 3H), 7.50-7.42 (m, 3H), 7.37-7.33 (m, 1H), 3.99 (dd, 1H), 1.90-1.76 (m, 2H), 1.66-1.56 (m, 1H), 1.47 (s, 9H), 0.96 (d, 3H) and 0.91 (d, 3H).

Intermediate 65 rel-(2S,4S,5R)-1-(4-tert-Butylbenzoyl)-2-isobutyl-4-pyrazin-2-yl-5-(3-phenyl-phenyl)-pyrrolidine-2-carboxylic acid, tert-butyl ester

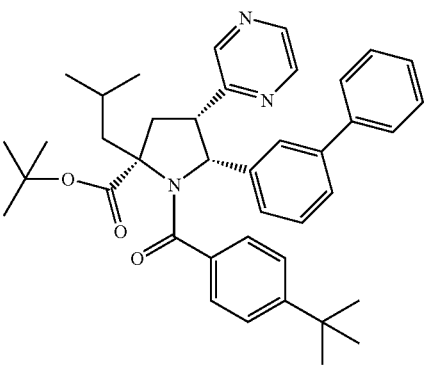

Racemic;
Relative stereochemistry shown

Stage A: rel-(2S,4S,5R)-2-isobutyl-4pyrazin-2-yl-5-(3-phenyl-phenyl)-pyrrolidine-2-carboxylic acid, tert-butyl ester was prepared in a similar manner to that described for Intermediate 2, replacing Intermediate 1 with Intermediate 64.

MS calcd for $(C_{29}H_{35}N_3O_2+H)^+$: 458.
MS found (electrospray): $(M+H)^+$=458.

Stage B: The ester from stage A was acylated with 4-tert-butylbenzoyl chloride in a similar manner to that described in Intermediate 3, to afford rel-(2S,4S,5R)-1-(4-tert-butylbenzoyl)-2-isobutyl-4-pyrazin-2-yl-5-(3-phenyl-phenyl)-pyrrolidine-2-carboxylic acid, tert-butyl ester.

MS calcd for $(C_{40}H_{47}N_3O_3+H)^+$: 618 MS found (electrospray): $(M+H)^+$=618.

Intermediate 66 rel-(2S,4S,5R)-2-(2-Benzyloxycarbonylmethyl-4-(pyrazin-2-yl)-5-(1,3-thiazol-2-yl)pyrrolidine-2-carboxylic acid, tert-butyl ester

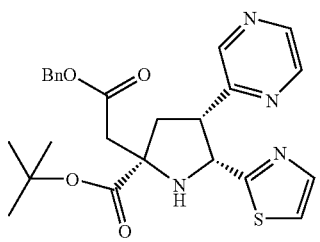

Racemic;
Relative stereochemistry shown

Prepared in a similar manner to that described for Intermediate 2, replacing Intermediate 1 with Intermediate 58.
MS calcd for $(C_{25}H_{28}N_4O_4S+H)^+$: 481.
MS found (electrospray): $(M+H)^+=481$.

Intermediate 67

2-Vinyl-5-trifluoromethylpyridine

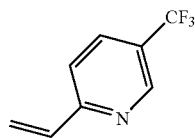

To a solution of vinylmagnesium bromide in THF (1M, 7.38 mL, 7.38 mmol) in THF (29 mL) was added anhydrous zinc bromide (1.66 g, 7.38 mmol) at −78° C. After one hour at this temperature, the mixture was warmed to room temperature. After one hour, tetrakis(triphenylphosphine)palladium(0) (147 mg) and 2-bromo-5-trifluoromethylpyridine (1 g, 4.42 mmol) were added and the mixture heated at 50° C. for 5.25 hours. The mixture was diluted with ammonium chloride solution (10%, 29 mL) and extracted with ethyl acetate (70 mL×2). The combined organic extracts were dried over magnesium sulphate, evaporated and purified by column chromatography (SPE column, silica), eluting with cyclohexane, followed by cyclohexane/ethyl acetate (95:5 v/v), then (9:1 v/v). This afforded the title compound.
$^1$H NMR (CDCl$_3$): δ 8.85 (s, 1H), 7.90 (d, 1H), 7.46 (d, 1H), 6.88 (dd, 1H), 6.36 (d, 1H), 5.65 (d, 1H).

Intermediate 68

(2S,4S,5R)-1-(4-tert-Butylbenzoyl)-2-isobutyl-4-(5-trifluoromethylpyridin-2-yl)-5-(1,3-thiazol-2-yl)pyrrolidine-2-carboxylic acid, tert-butyl ester

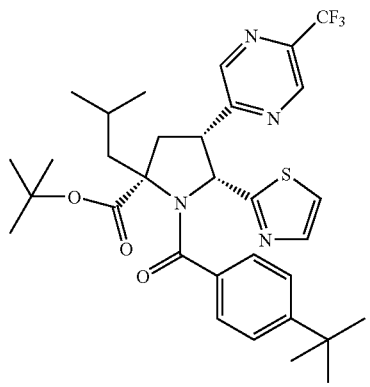

Chiral;
Relative stereochemistry shown

Stage A: (2S,4S,5R)-2-Isobutyl-4-(5-trifluoromethylpyridin-2-yl)-5-(1,3-thiazol-2-yl)pyrrolidine-2-carboxylic acid, tert-butyl ester was prepared in a similar manner to that described for Intermediate 2, replacing 2-vinylpyrazine with Intermediate 67.
MS calcd for $(C_{22}H_{28}F_3N_3O_2S+H)^+$: 456.
MS found (electrospray): $(M+H)^+=456$.
Stage B: The title compound was prepared in a similar manner to that described for Intermediate 3, replacing Intermediate 2 with the compound described in stage A.
MS calcd for $(C_{33}H_{40}F_3N_3O_3S+H)^+$: 616.
MS found (electrospray): $(M+H)^+=616$.

Intermediate 69

(2S,4S,5R)-1-(4-tert-Butylbenzoyl)-2-isobutyl-4-(5-trifluoromethylpyridin-2-yl)-5-(1,3-thiazol-2-yl)pyrrolidine-2-carboxylic acid, tert-butyl ester

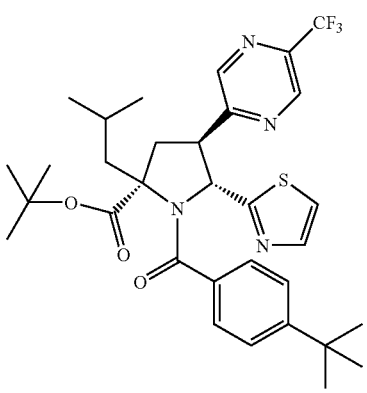

Chiral;
Relative stereochemistry shown

A solution of Intermediate 68 (111 mg, 0.18 mmol) was added to a solution of NaOH in methanol (0.1N, 1.8 mL) and the solution placed for 3 days at room temperature. The solvent was removed in vacuo and the residue neutralised by the addition of hydrochloric acid (2N, 90 ul). Water (5 mL) and dichloromethane (5 mL) were added. The aqueous phase was further extracted with dichloromethane (5 mL), the organic fractions were combined, dried over sodium sulphate, and evaporated. The product was purified by preparative TLC, eluting with cyclohexane/ethyl acetate (4:1 v/v). The faster running band was extracted with ethyl acetate to afford the title compound. The stereochemistry was confirmed by one studies.
MS calcd for $(C_{33}H_{40}F_3N_3O_3S+H)^+$: 616.
MS found (electrospray): $(M+H)^+=616$.

Intermediate 70 rel-(2S,4S,5R)-2-Isobutyl-4-pyrazin-2-yl-5-(4-dimethylaminophenyl)-pyrrolidine-2-carboxylic acid, tert-butyl ester

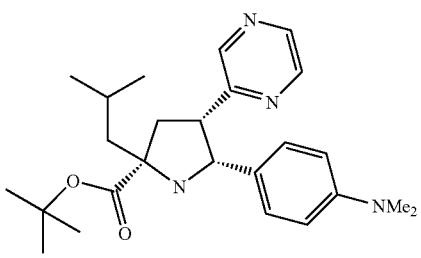

Racemic;
Relative stereochemistry shown

Prepared in a similar manner to that described for Intermediate 1, replacing 1,3-thiazole-2-carboxaldehyde with 4-dimethylaminobenzaldehyde.

MS calcd for $(C_{25}H_{36}N_4O_2+H)^+$: 425.
MS found (electrospray): $(M+H)^+=425$.

Intermediate 71

2-[N-(1,3-Thiazol-2-ylmethylene)amino]-3-(1-triphenylmethyl-1H-imidazol-4-yl)-propionic acid, tert-butyl ester

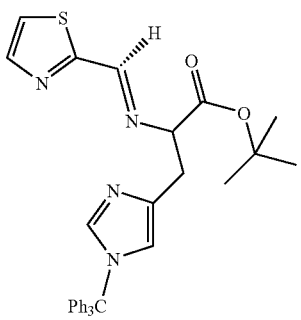

Prepared in a similar manner to that described for Intermediate 1, replacing 2-amino-4-methyl-pentanoic acid tert-butyl ester, hydrochloride with 2-amino 3-(1-triphenylmethyl-1H-imidazol-5-yl)-propionic acid, tert-butyl ester hydrochloride.

$^1$H NMR (CDCl$_3$): δ 8.20 (s, 1H), 7.95 (d, 1H), 7.42 (d, 1H), 7.33 (s, 1H), 7.28-7.18 (m,9H), 7.05-6.99 (m, 6H), 6.51 (s, 1H), 4.37 (dd, 1H), 3.30 (dd, 1H), 3.03 (dd, 1H), 1.45 (s, 9H).

Intermediate 72 rel-(2S,4S,5R)-1-(4-tert-Butyl-3-methoxybenzoyl)-2-(1-triphenylmethyl-1H-imidazol-4-yl-methyl)-4-pyrazin-2-yl-5(1,3-thiazol-2-yl)-pyrrolidine-2-carboxylic acid, tert-butyl ester

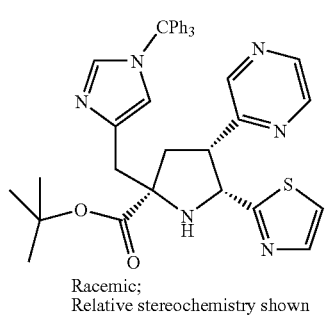

Racemic;
Relative stereochemistry shown

Prepared in a similar manner to that described for Intermediate 2, replacing Intermediate 1 with Intermediate 71.

MS calcd for $(C_{51}H_{52}N_6O_4S+H)^+$: 846.
MS found (electrospray): $(M+H)^+=846$.

Intermediate 73

2-[N-(2-Methylpropylene)amino]-4-methylpentanoic acid, tert-butyl ester

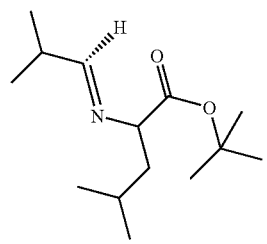

Prepared in a similar manner to that described for Intermediate 46, replacing acetaldehyde with 2-methylpropionaldehyde.

$^1$H NMR (CDCl$_3$): δ 7.50 (d, 1H), 3.66 (dd, 1H), 2.56-2.41 (m, 1H), 1.78-1.61 (m, 2H), 1.56-1.45 (s+m, 10H), 1.08 (d, 6H), 0.92 (d, 3H), 0.84 (d, 3H).

Intermediate 74 rel-(2S,4S,5S)-2-Isobutyl-4-pyrazin-2-yl-5-isopropyl-pyrrolidine-2-carboxylic acid, tert-butyl ester

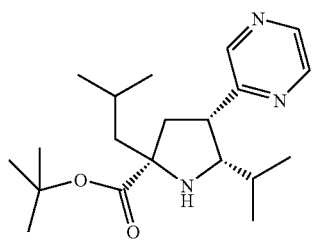

Racemic;
Relative stereochemistry shown

Prepared in a similar manner to that described for Intermediate 2, replacing triethylamine with 1,8-diazabicyclo[5,4,0]undec-7-ene (DBU) and Intermediate 1 with Intermediate 73.

MS calcd for $(C_{20}H_{33}N_3O_2+H)^+$: 348.
MS found (electrospray): $(M+H)^+=348$.

Intermediate 75

2-[N-(1,3-Thiazol-2-ylmethylene)amino]-4-(methylthio)-butanoic acid, tert-butyl ester

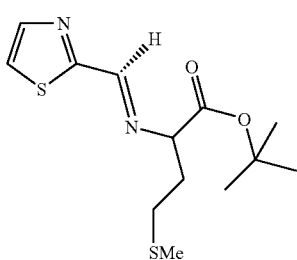

Prepared in a similar manner to that described for Intermediate 1, replacing 2-amino-4-methyl-pentanoic acid tert-butyl ester, hydrochloride with methionine tert-butyl ester hydrochloride.

$^1$H NMR (CDCl$_3$): δ 8.49 (s, 1H), 7.95 (d, 1H), 7.45 (d, 1H), 4.18 (dd, 1H), 2.63-2.55 (m, 1H), 2.51-2.42 (m, 1H), 2.29-2.19 (m, 2H), 2.09 (s, 3H), 1.47 (s, 9H).

Intermediate 76 rel-(2S,4S,5R)-2-(2-(Methylthio)ethyl)-4-pyrazin-2-yl-5-(1,3-thiazol-2-yl)-pyrrolidine-2-carboxylic acid, tert-butyl ester

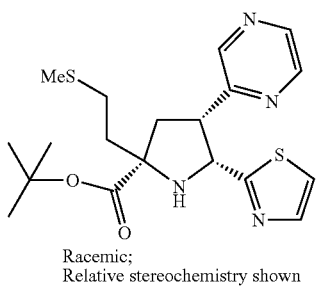

Racemic;
Relative stereochemistry shown

Prepared in a similar manner to that described for Intermediate 2, replacing Intermediate 1 with Intermediate 75.

MS calcd for (C$_{19}$H$_{26}$N$_4$O$_2$S$_2$+H)$^+$: 407.
MS found (electrospray): (M+H)$^+$=407.

Intermediate 77 rel-(2S,4R,5R)-1-(4-tert-Butylbenzoyl)-2-isobutyl-4-pyrazin-2-yl-5-(1,3-thiazol-2-yl)pyrrolidine-2-carboxylic acid, tert-butyl ester

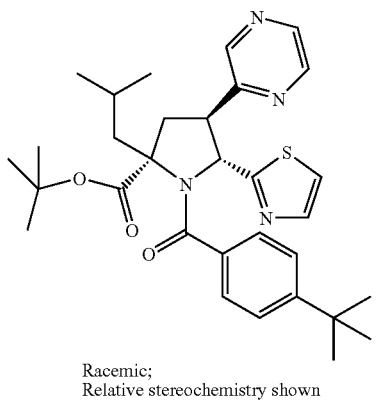

Racemic;
Relative stereochemistry shown

Prepared in a similar manner to that described for Intermediate 69, replacing Intermediate 68 with Intermediate 3. The reaction was heated at 55° C. for 5 days and purification was by preparative TLC eluting with ethyl acetate.

MS calcd for (C$_{31}$H$_{40}$N$_4$O$_3$S+H)$^+$: 549.
MS found (electrospray): (M+H)$^+$=549.

Intermediate 78

4Cyano-2-vinylpyridine

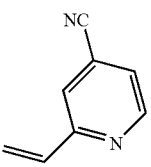

Stage A: A mixture of 4-cyanopyridine (5.08 g, 48.8 mmol), ammonium persulphate (22.9 g, 100 mmol), methanol (75 mL), water (35 mL) and conc. sulphuric acid (2.7 mL) was heated at 62° C. for 20 hours. The methanol was removed in vacuo, followed by the addition of sodium hydroxide solution (2M, 60 mL) and chloroform (70 mL). The aqueous phase was further extracted 3 times with chloroform, then with ethyl acetate. The organic fractions were combined, dried over magnesium sulphate and evaporated. The product was purified by silica column chromatography using a Biotage cartridge (90 g), eluting with cyclohexane/ethyl acetate (2:1 v/v), then (1:1 v/v). This afforded 4-cyano-2-hydroxymethylpyridine as a solid.

Stage B: To 4-cyano-2-hydroxymethylpyridine (1.1 g, 8.2 mmol) from stage A in dry DMSO (18 mL) was added N,N-dicyclohexylcarbodiimide (5.08 g, 24.6 mmol) and phosphoric acid (0.4 g, 4.1 mmol). The mixture was stirred overnight at room temperature. The solid was removed by filtration and washed with ether and water. The filtrate and washings were combined, and the organic layer separated. The aqueous layer was further extracted 4 times with ether, the organics combined, dried over magnesium sulphate and evaporated. The residue was purified by SPE silica column chromatography, eluting with dichloromethane, then chloroform, then diethyl ether. Evaporation of the appropriate fractions afforded 4-cyanopyridine-2-carboxaldehyde as a solid.

Stage C: A mixture of 4-cyanopyridine-2-carboxaldehyde (0.916 g, 6.93 mmol), methyltriphenylphosphonium bromide (2.48 g, 6.93 mmol), potassium carbonate (1.2 g, 8.66 mmol), 1,4 dioxan (9.5 mL) and water (0.13 mL) was heated under reflux for 5 hours. The mixture was diluted with water (30 mL) and ethyl acetate (70 mL) and the organic layer separated. The aqueous phase was further extracted with ethyl acetate (2×40 mL), the organic fractions combined and dried over magnesium sulphate. After removing the solvent, the residue was purified by silica column chromatography using a Biotage cartridge and eluting with cyclohexane/ethyl acetate (7:3 v/v), then (1:1 v/v). This gave the title compound as an oil.

¹H NMR (CDCl₃): δ 8.74 (d, 1H), 7.54 (s, 1H), 7.38 (d, 1H), 6.83 (dd, 1H), 6.33 (d, 1H), 5.64 (d, 1H).

Intermediate 79 rel-(2S,4S,5R)-2-Isobutyl-4-(4-cyanopyridin-2-yl)-5-(1,3-thiazol-5-yl)pyrrolidine-2-carboxylic acid, tert-butyl ester

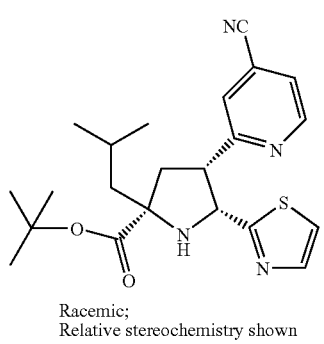

Racemic;
Relative stereochemistry shown

Prepared in a similar manner to that described for Intermediate 2 replacing 2-vinylpyrazine with 4-cyano-2-vinylpyridine.

MS calcd for $(C_{22}H_{28}N_4O_2S+H)^+$: 413.
MS found (electrospray): $(M+H)^+$=413.

Intermediate 80

4-(2-Hydroxyethyl)pyrimidine

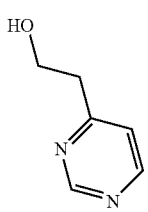

A mixture of 4-methylpyrimidine (10 g, 106 mmol) and para-formaldehyde (3 g) was stirred in a 50 mL sealed capacity pressure vessel at 165° C. for 3.5 hours. After cooling, ether was added and the solvents evaporated to afford an oil. This was purified by silica column chromatography using a Flashmaster system, eluting with dichloromethane, then chloroform, ether, and finally ethyl acetate. The ethyl acetate fractions were evaporated to afford the title compound as an oil.

¹H NMR (CDCl₃): δ 9.13 (s, 1H), 8.64 (d, 1H), 7.23 (d, 1H), 4.07-4.05 (m, 2H), 3.48 (brt, 1H), 3.04-3.01 (m, 2H).

Intermediate 81 rel-(2S,4S,5R)-2-Isobutyl-4-pyrimidin-4-yl)-5-(1,3-thiazol-2-yl)pyrrolidine-2-carboxylic acid, tert-butyl ester

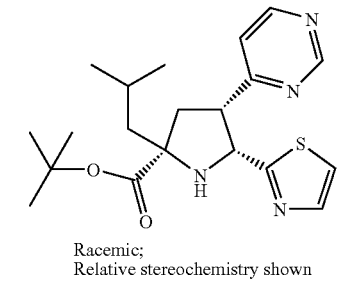

Racemic;
Relative stereochemistry shown

To 4-(2-hydroxyethyl)pyrimidine, Intermediate 80, (0.605 g, 4.87 mmol) in dry dichloromethane (12 mL) at 0° C. was added triethylamine (1.02 mL, 7.3 mmol) and methanesulphonyl chloride (0.57 mL, 7.3 mmol). After 10 minutes at this temperature the mixture was allowed to attain room temperature and stirred for 16 hours. The mixture was cooled to 0° C. Intermediate 1 (1.37 g, 4.85 mmol) in dry THF (12 mL) was added, followed by lithium bromide (0.846 g, 9.74 mmol) and triethylamine (1.02 mL, 7.3 mmol). After stirring at room temperature for 2 days, work up and purification as previously described for Intermediate 2 afforded the title compound as a gum.

MS calcd for $(C_{20}H_{28}N_4O_2S+H)^+$: 389.
MS found (electrospray): $(M+H)^+$=389.

Intermediate 82

2-[N-(1,3-Thiazol-2-ylmethylene)amino]-4-methylsulphonyl-butanoic acid, tert-butyl ester

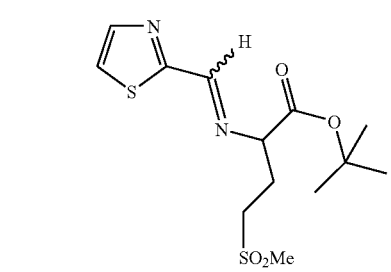

Prepared in a similar manner to that described for Intermediate 1, replacing 2-amino-4-methyl-pentanoic acid tert-butyl ester, hydrochloride with methionine sulphone tert butyl ester.

¹H NMR (CDCl₃): δ 8.52 (s, 1H), 7.97 (d, 1H), 7.48 (d, 1H), 4.20 (t, 1H), 3.17 (dd, 2H), 2.95 (s, 3H), 2.51-2.46 (m, 2H), 1.47 (s, 9H).

Intermediate 83 rel-(2S,4S,5R)-2-(2-(Methylsulphonyl)ethyl)-4-pyrazin-2-yl-5-(1,3-thiazol-2-yl)-pyrrolidine-2-carboxylic acid, tert-butyl ester

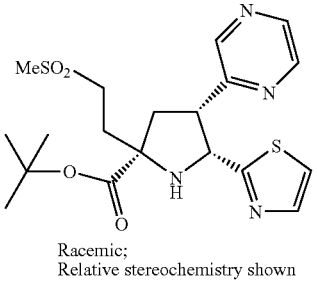

Racemic;
Relative stereochemistry shown

Prepared in a similar manner to that described for Intermediate 2, replacing Intermediate 1 with intermediate 82.
MS calcd for $(C_{30}H_{38}N_4O_5S_2+H)^+$: 599.
MS found (electrospray): $(M+H)^+=599$.

Intermediate 84

2-[N-(1,3-Thiazol-2-ylmethylene)amino]-propionic acid, tert-butyl ester

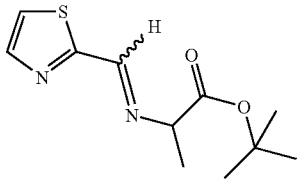

Prepared in a similar manner to that described for Intermediate 1, replacing 2-amino4-methyl-pentanoic acid tert-butyl ester, hydrochloride with alanine, tert butyl ester hydrochloride.
NMR (CDCl$_3$): δ 8.5 (d, 1H), 7.9 (d, 1H), 7.4 (d, 1), 4.15 (q, 1H), 1.6 (s, 3H), 1.45 (s, 9H).

Intermediate 85 rel-(2S,4S,5R)-2-Methyl-4-(pyrazin-2-yl)-5-(1,3-thiazol-5-yl)pyrrolidine-2-carboxylic acid, tert-butyl ester

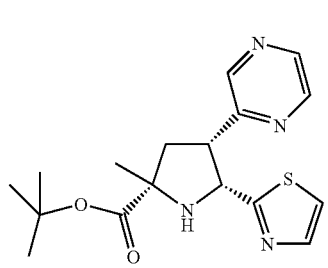

Racemic;
Relative stereochemistry shown

Prepared in a similar manner to that described for Intermediate 2, replacing Intermediate 1 with Intermediate 84.
MS calcd for $(C_{17}H_{22}N_4O_2S+H)^+$: 347.
MS found (electrospray): $(M+H)^+=347$.

Intermediate 86

2-[N-(2-Phenyl-1,3-thiazol-4-ylmethylene)amino]-propionic acid, tert-butyl ester

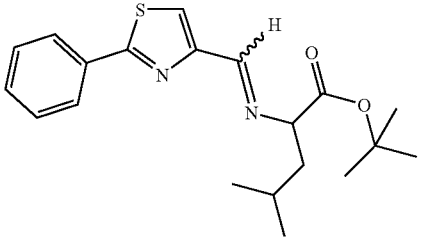

Prepared in a similar manner to that described for Intermediate 1, replacing 1,3-thiazole-2-carboxaldehyde with 2-phenyl-1,3-thiazol-4-carboxaldehyde.
NMR (CDCl$_3$); δ 8.5 (s, 1H), 8.2 (s, 1H), 8.0 (m, 3H), 7.45 (m, 3H), 4.0 (q, 1H), 1.8 (m, 2H), 1.6 (m, 1H), 1.5 (s, 9H) 0.94 (m, 6H).

Intermediate 87 rel-(2S,4S,5R)-2-Isobutyl-4-(pyrazin-2-yl)-5-(2-phenyl-1,3-thiazol-4-yl)pyrrolidine-2-carboxylic acid, tert-butyl ester

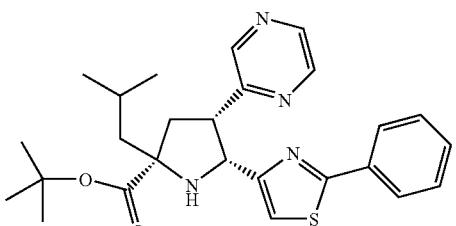

Racemic;
Relative stereochemistry shown

Prepared in a similar manner to that described for Intermediate 2, replacing Intermediate 1 with Intermediate 86.
MS calcd for $(C_{26}H_{32}N_4O_2S+H)^+$: 465.
MS found (electrospray): $(M+H)^+=465$.

Intermediate 88

2-[N-(1,3-Thiazol-4-ylmethylene)amino]-3-(pyridin-2-yl)propionic acid, tert-butyl ester

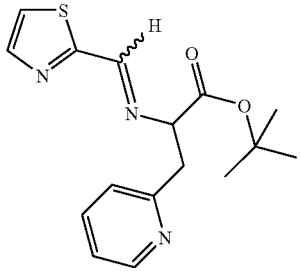

Prepared in a similar manner to that described for Intermediate 1, replacing 2-amino-4-methyl-pentanoic acid tert-butyl ester, hydrochloride with 2-amino-3-(2-pyridyl) propionic acid, tert-butyl ester.
NMR (CDCl$_3$); δ 8.5 (d, 1H), 8.2 (s, 1H), 7.9 (d, 1H), 7.5 (t, 1H), 7.4 (d, 1H), 7.15 (d, 1H), 7.10 (t, 1H), 4.6 (q, 1H), 3.5 (dd, 1H), 3.3 (dd, 1H), 1.4 (s, 9H).

Intermediate 89 rel-(2S,4S,5R)-2-(2-Pyridin-2-ylmethyl)-4-(pyrazin-2-yl)-5-(1,3-thiazol-2-yl)pyrrolidine-2-carboxylic acid, tert-butyl ester

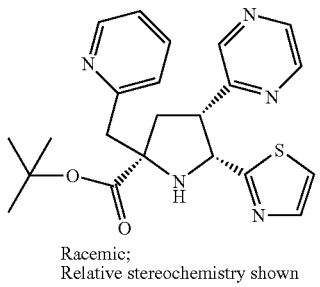

Racemic;
Relative stereochemistry shown

Prepared in a similar manner to that described for Intermediate 2, replacing Intermediate 1 with Intermediate 88, and replacing triethylamine with DBU.

MS calcd for $(C_{22}H_{35}N_5O_2S+H)^+$: 424.
MS found (electrospray): $(M+H)^+$=424.

Intermediate 90

4-tert-Butyl-3-ethylbenzoic acid

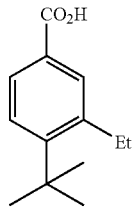

A solution of n-butyl lithium (1.6M in hexane, 2.67 mL, 4.27 mmol) was added dropwise to a solution of 4-tert-butyl-3-bromobenzoic acid (500 mg, 1.94 mmol) in THF at −78° C. whilst maintaining the temperature below −70° C. After 40 minutes, ethyl iodide (1.55 mL, 19.4 mmol) was added dropwise whilst maintaining the temperature below −65° C. After one hour at −70° C., the mixture was allowed to attain room temperature and stirred overnight The mixture was quenched by the addition of saturated ammonium chloride solution (30 mL) and extracted with ether (30 mL). The organic fraction was dried over magnesium sulphate and evaporated. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{13}H_{18}O_2-H)^-$: 205.
MS found (electrospray): $(M-H)^-$=205.

Intermediate 91

4-tert-Butyl-3-ethoxybenzoic acid

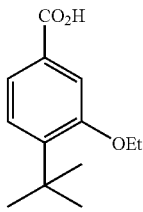

Prepared in a similar manner to that described for 4-tert-butyl-3-methoxybenzoic acid (J. Org. Chem. (1961) 26,1732), replacing methyl iodide with ethyl iodide.

MS calcd for $(C_{13}H_{18}O_3-H)^-$: 221.
MS found (electrospray): $(M-H)^-$=221.

Intermediate 92

Enantiomer A of rel-(2S,4S,5R)-2-Isobutyl-4-pyrazin-2-yl-5-(1,3-thiazol-2-yl)pyrrolidine-2-carboxylic acid, tert-butyl ester

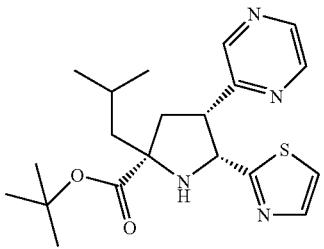

Chiral;
Relative stereochemistry shown

Intermediate 2 (7.0 g) was dissolved in heptane (700 mL) and aliquots of ca. 10 mL injected onto a preparative HPLC column (50 mm id) packed with Chiralpac AD stationary phase. Each injection was eluted with 5% v/v ethanol in heptane at a flow rate of 80 mL/min. The product from each injection was analysed in real time using UV-visible detection at a wavelength of 270 nm and fractions taken for each enantiomer. Following repeat injections all fractions containing the second eluted enantiomer were combined and evaporated in vacuo to yield the title compound as a solid. This enantiomer was identical by LC-MS to the racemic compound.

Intermediate 93

2-[N-(1,3-thiazol-4-ylmethylene)amino]-3-(phenyl)propionic acid, tert-butyl ester

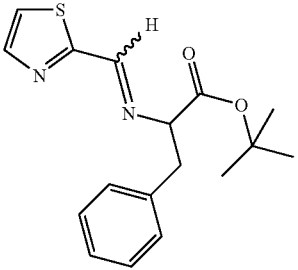

Prepared in a similar manner to that described for Intermediate 1, replacing 2-amino-4-methyl-pentanoic acid tert-butyl ester, hydrochloride with 2-amino-3-(2-phenyl)-propionic acid, tert-butyl ester hydrochloride.

NMR (CDCl$_3$); δ 8.1 (s, 1H), 8.2 (s, 1H), 7.9 (d, 1H), 7.4 (d, 1H), 7.2 (m, 5H), 7.10 (t, 1H), 4.2 (q, 1H), 3.3 (dd, 1H), 3.1 (dd, 1H), 1.4 (s, 9H).

Intermediate 94 rel-(2S,4S,5R)-2-Phenylmethyl-4-(pyrazin-2-yl)-5-(1,3thiazol-2-yl)pyrrolidine-2-carboxylic acid, tert-butyl ester

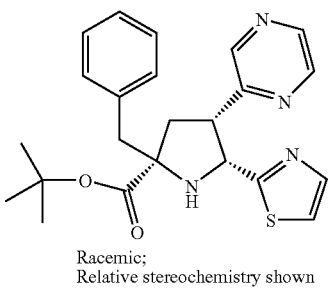

Racemic;
Relative stereochemistry shown

Prepared in a similar manner to that described for Intermediate 2, replacing Intermediate 1 with Intermediate 93.
MS calcd for (C$_{23}$H$_{26}$N$_4$O$_2$S+H)$^+$: 423.
MS found (electrospray): (M+H)$^+$=423.

Example 1 rel-(2S,4S,5R)-1-(4-tert-Butylbenzoyl)-2-isobutyl-4-(pyrazin-2-yl)-5-(1,3-thiazol-2-yl)pyrrolidine-2-carboxylic acid

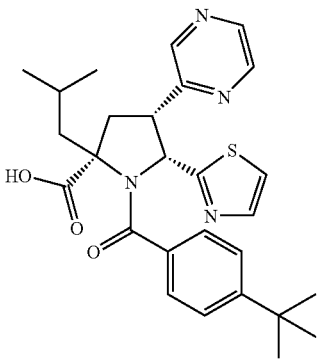

Racemic;
Relative stereochemistry shown

Intermediate 3 (88 mg, 0.16 mmol) was dissolved in trifluoroacetic acid (5 mL). The reaction was stirred at room temperature for 6 hours. The solvent was then evaporated in vacuo and the residue was triturated with diethyl ether. The resulting solid was collected by filtration and dried in vacuo to give the title compound.
MS calcd for (C$_{27}$H$_{32}$N$_4$O$_3$S+H)$^+$: 493.
MS found (electrospray): (M+H)$^+$=493.

Example 2 rel-(2S,4S,5R)-1-(4-tert-Butylbenzoyl)-2-isobutyl-4-(5-methyl-pyrazin-2-yl)-5-(1,3-thiazol-2-yl)pyrrolidine-2-carboxylic acid

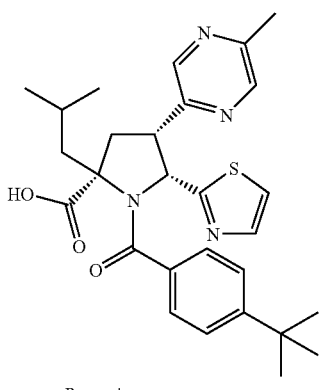

Racemic;
Relative stereochemistry shown

The title compound was prepared from Intermediate 5 in a similar manner to that described in Example 1.
MS calcd for (C$_{28}$H$_{34}$N$_4$O$_3$S+H)$^+$: 507.
MS found (electrospray): (M+H)$^+$=507.

Example 3 rel-(2S,4S,5R)-1-(4-tert-Butylbenzoyl)-2-isobutyl-4-(pyridin-2-yl)-5-(1,3-thiazol-2-yl)pyrrolidine-2-carboxylic acid

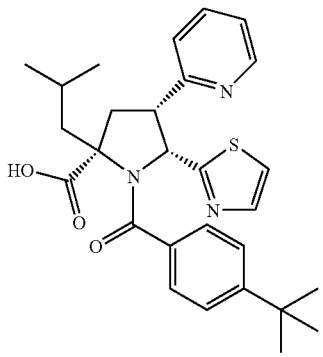

Racemic;
Relative stereochemistry shown

The title compound was prepared from Intermediate 7 in a similar manner to that described in Example 1.
MS calcd for (C$_{28}$H$_{33}$N$_3$O$_3$S+H)$^+$: 492.
MS found (electrospray): (M+H)$^+$=492.

Example 4 rel-(2S,4R,5R)-1-(4-tert-Butylbenzoyl)-2-isobutyl-4-(pyridin-4-yl)-5-(1,3-thiazol-2-yl)pyrrolidine-2-carboxylic acid

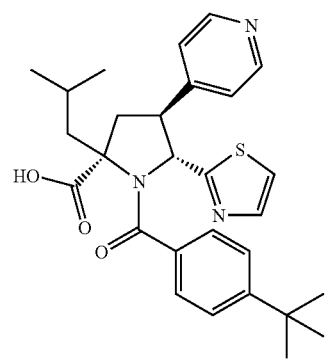

Racemic;
Relative stereochemistry shown

The title compound was prepared from Intermediate 9 in a similar manner to that described in Example 1. Proton NMR nOe studies confirmed the stereochemistry to be 2S, 4R, 5R.

MS calcd for $(C_{28}H_{33}N_3O_3S+H)^+$: 492.
MS found (electrospray): $(M+H)^+=492$.

Example 5 rel-(2S,4S,5R)-1-(4-tert-Butylbenzoyl)-2-isobutyl-4-(pyrimidin-5yl)-5-(1,3-thiazol-2-yl)pyrrolidine-2-carboxylic acid

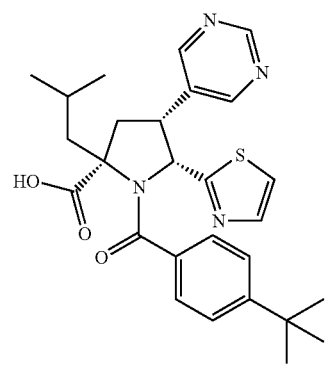

Racemic;
Relative stereochemistry shown

The title compound was prepared from Intermediate 11 in a similar manner to that described in Example 1.
MS calcd for $(C_{27}H_{32}N_4O_3S+H)^+$: 493.
MS found (electrospray): $(M+H)^+=493$.

Example 6 rel-(2S,4S,5R)-1-(4-tert-Butylbenzoyl)-2-isobutyl-4-(6-methyl-pyridazin-2-yl)-5-(1,3-thiazol-2-yl)pyrrolidine-2-carboxylic acid

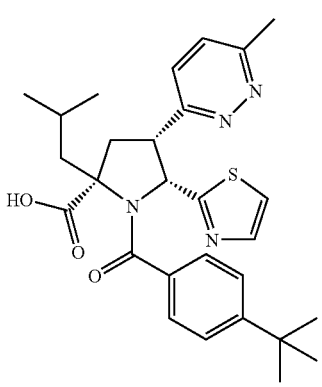

Racemic;
Relative stereochemistry shown

The title compound was prepared from Intermediate 13 in a similar manner to that described in Example 1.
MS calcd for $(C_{28}H_{34}N_4O_3S+H)^+$: 507.
MS found (electrospray): $(M+H)^+=507$.

Example 7 rel-(2S,4S,5R)-1-(4-tert-Butylbenzoyl)-2-isobutyl-4-(pyrazin-2-yl)-5-(pyridin-2-yl)pyrrolidine-2-carboxylic acid

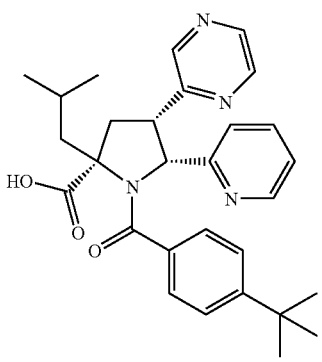

Racemic;
Relative stereochemistry shown

The title compound was prepared from Intermediate 16 in a similar manner to that described in Example 1.
MS calcd for $(C_{29}H_{34}N_4O_3+H)^+$: 487
MS found (electrospray): $(M+H)^+=487$

Example 8 rel-(2S,4S,5R)-1-(3-Bromo-4-tert-butylbenzoyl)-2-isobutyl-4-(pyrazin-2-yl)-5-(pyridin-2-yl)pyrrolidine-2-carboxylic acid

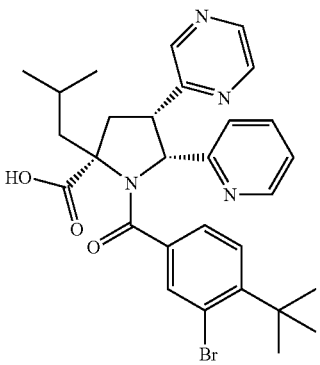

Racemic;
Relative stereochemistry shown

The title compound was prepared from Intermediate 17 in a similar manner to that described in Example 1.

MS calcd for $(C_{29}H_{33}BrN_4O_3+H)^+$: 565/567.
MS found (electrospray): $(M+H)^+=565/567$.

Example 9 rel-(2S,4S,5R)-1-(3-Bromo-4-tert-butylbenzoyl)-2-isobutyl-4-(pyrazin-2-yl)-5-(1,3-thiazol-2-yl)pyrrolidine-2-carboxylic acid

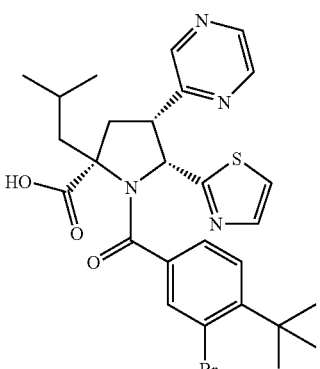

Racemic;
Relative stereochemistry shown

The title compound was prepared from Intermediate 18 in a similar manner to that described in Example 1.

MS calcd for $(C_{27}H_{31}BrN_4O_3S+H)^+$: 571/573.
MS found (electrospray): $(M+H)^+=571/573$.

Example 10 rel-(2S,4S,5R)-1-(3-Bromo-4-tert-butylbenzoyl)-2-isobutyl-4-(5-methyl-pyrazin-2-yl)-5-(1,3-thiazol-2-yl)pyrrolidine-2-carboxylic acid

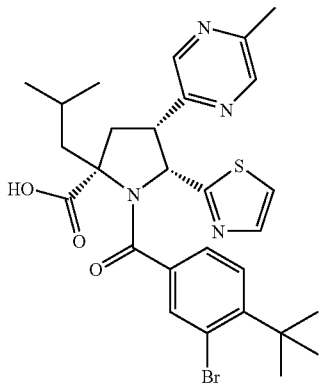

Racemic;
Relative stereochemistry shown

The title compound was prepared from Intermediate 19 in a similar manner to that described in Example 1.

MS calcd for $(C_{28}H_{33}BrN_4O_3S+H)^+$: 585/587.
MS found (electrospray): $(M+H)^+=585/587$.

Example 11 rel-(2S,4S,5R)-1-(3-Bromo-4-tert-butylbenzoyl)-2-isobutyl-4-(pyradazin-3-yl)-5-(1,3-thiazol-2-yl)pyrrolidine-2-carboxylic acid

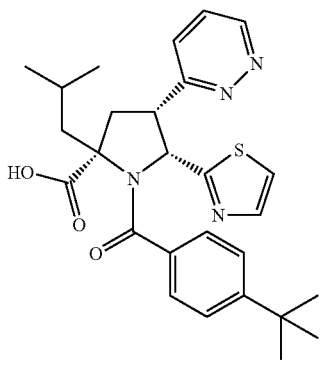

Racemic;
Relative stereochemistry shown

This was prepared from Intermediate 33 in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{27}H_{32}N_4O_3S+H)^+$: 493.
MS found (electrospray): $(M+H)^+=493$.

Example 12

2nd Eluting isomer of rel-(2S,4S,5R)-1-(4-tert-Butylbenzoyl)-2-isobutyl-4-(pyrazin-2-yl)-5-(1,3-thiazol-2-yl)pyrrolidine-2-carboxylic acid

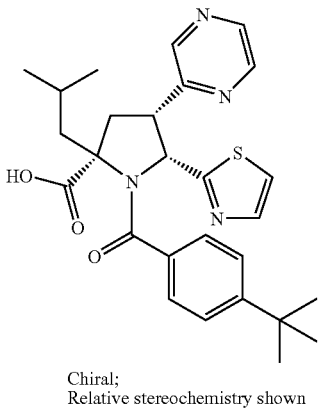

Chiral;
Relative stereochemistry shown rel-(2S,4S,5R)-1-(4-tert-Butylbenzoyl)-2-isobutyl-4-pyrazin-2-yl-5-(1,3-thiazol-2-yl)pyrrolidine-2-carboxylic acid (Example 1) was resolved by preparative HPLC on a Chiralpak AD chromatography column using heptane-ethanol (70:30 v/v) containing 0.1% trifluoroacetic acid as eluent to afford the individual enantiomers with retention times of 5 minutes ($1^{st}$ eluting Enantiomer) and 6 minutes ($2^{nd}$ eluting Enantiomer, the title compound) respectively. The $2^{nd}$ a eluting enantiomer was identical by LCMS to the racemic compound described for Example 1.

$^1$H NMR (CD$_3$OD): δ 8.44 (1H, s), 8.21 (1H, d), 8.16 (1H, d), 7.54 (1H, d), 7.18 (3H, m), 6.94 (2H, d), 5.94 (1H, d), 4.51-4.44 (1H, m), 3.17 (1H, t), 2.41 (1H, dd), 2.31-2.19 (2H, m), 2.12-2.02 (1H, m), 1.13 (9H, s), 1.10 (3H, d), 1.05 (3H, d).

Example 13

Enantiomer A of rel-(2S,4S,5R)-1-(3-Bromo-4-tert-butylbenzoyl)-2-isobutyl-4-pyrazin-2-yl-5-(1,3-thiazol-2-yl)pyrrolidine-2-carboxylic acid

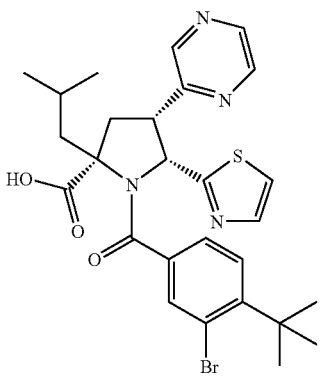

Chiral;
Relative stereochemistry shown

The title compound was prepared from Intermediate 21 (Enantiomer A) in a similar manner to that described in Example 1.

MS calcd for (C$_{27}$H$_{31}$BrN$_4$O$_3$S+H)$^+$: 571/573.
MS found (electrospray): (M+H)$^+$=571/573.

Example 14

Enantiomer A of rel-(2S,4S,5R)-1-(4-tert-Butylbenzoyl)-2-isobutyl-4-(pyrazin-2-yl)-5-(pyridin-2-yl)pyrrolidine-2-carboxylic acid

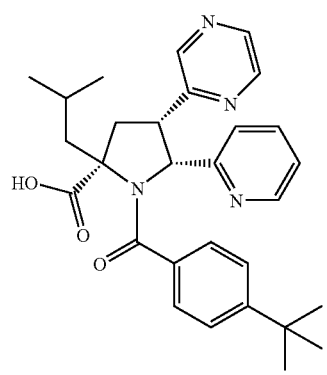

Chiral;
Relative stereochemistry shown

The title compound was prepared from Intermediate 22 (Enantiomer A) in a similar manner to that described in Example 1.

MS calcd for (C$_{29}$H$_{34}$N$_4$O$_3$+H)$^+$: 487.
MS found (electrospray): (M+H)$^+$=487.

Example 15

Enantiomer A of rel-(2S,4S,5R)-1-(3-Bromo-4-tert-butylbenzoyl)-2-isobutyl-4-pyrazin-2-yl)-5-pyridin-2-yl)pyrrolidine-2-carboxylic acid

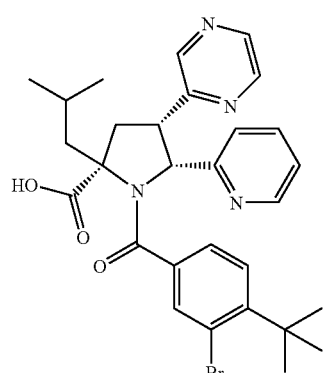

Chiral;
Relative stereochemistry shown

The title compound was prepared from Intermediate 23 (Enantiomer A) in a similar manner to that described in Example 1.
MS calcd for $(C_{29}H_{33}BrN_4O_3S+H)^+$: 565/567.
MS found (electrospray): $(M+H)^+=565/567$.

Example 16

Enantiomer A of rel-(2S,4S,5R)-1-(4-tert-Butylbenzoyl)-2-isobutyl-4-(pyrazin-2-yl)-5-(1,3-benzothiazol-2-yl)pyrrolidine-2-carboxylic acid

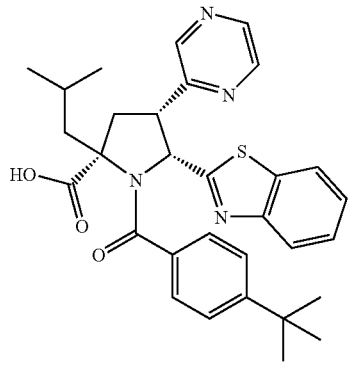

Chiral;
Relative stereochemistry shown

The title compound was prepared from intermediate 31 (Enantiomer A) in a similar manner to that described in Example 1. It was purified by SPE ($C_{18}$), loading the sample in water and eluting with water followed by methanol. Further purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy.
MS calcd for $(C_{31}H_{34}N_4O_3S+H)^+$: 543.
MS found (electrospray): $(M+H)^+=543$.

Example 17

Enantiomer A of rel-(2S,4S,5R)-1-(3-Bromo-4-tert-butylbenzoyl)-2-isobutyl-4-pyrazin-2-yl)-5-(1,3-benzothiazol-2-yl)pyrrolidine-2-carboxylic acid

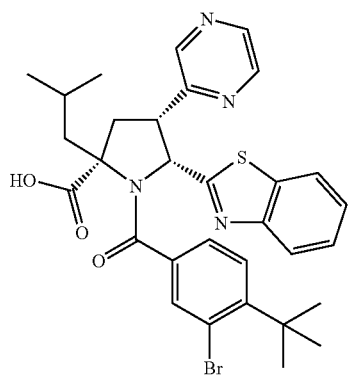

Chiral;
Relative stereochemistry shown

The title compound was prepared from Intermediate 30 (Enantiomer A) in a similar manner to that described in Example 1. The title compound was purified by SPE ($C_{18}$), loading the sample in water and eluting with water followed by methanol.
MS calcd for $(C_{31}H_{33}BrN_4O_3S+H)^+$: 621/623.
MS found (electrospray): $(M+H)^+=621/623$.

Example 18

Enantiomer A of rel-(2S,4S,5R)-1-(4-tert-Butyl-3-chlorobenzoyl)-2-isobutyl-4-(pyrazin-2-yl)-5-(1,3-thiazol-2-yl)pyrrolidine-2-carboxylic acid

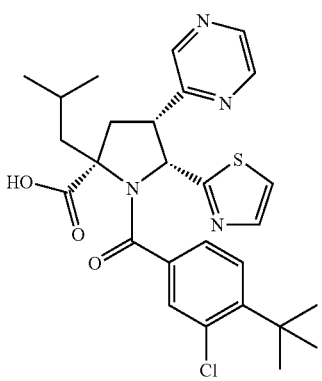

Chiral;
Relative stereochemistry shown

The title compound was prepared from Intermediate 25 (Enantiomer A), in a similar manner to that described in Example 1.
MS calcd for $(C_{27}H_{31}ClN_4O_3S+H)^+$: 527/529.
MS found (electrospray): $(M+H)^+=527/529$.

Example 19

Enantiomer A of rel-(2S,4S,5R)-1-(4-tert-butyl-3-methoxybenzoyl)-2-isobutyl-4-(pyrazin-2-yl)-5-(1,3-thiazol-2-yl)pyrrolidine-2-carboxylic acid

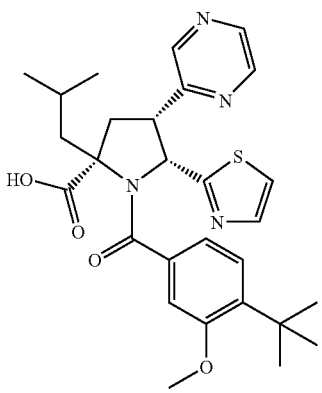

Chiral;
Relative stereochemistry shown

The title compound was prepared from Intermediate 27 (Enantiomer A), in a similar manner to that described in Example 1.
MS calcd for $(C_{28}H_{34}N_4O_4S+H)^+$: 523.
MS found (electrospray): $(M+H)^+=523$.

Example 20

Enantiomer A of rel-(2S,4S,5R)-1-(3-Bromo-4-tert-butylbenzoyl)-2-isobutyl-4-(pyrazin-2-yl)-5-(pyridin-2-yl)pyrrolidine-2-carboxamide

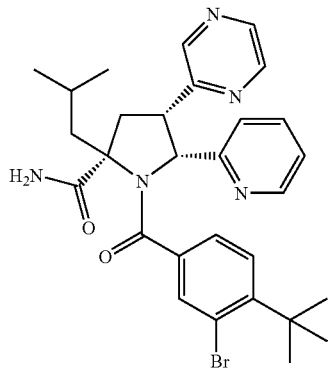

Chiral;
Relative stereochemistry shown

To a solution of Example 15 (28.2 mg, 0.05 mmol) and ammonium chloride (10 mg, 0.19 mmol) in DMF (1 mL) was added diisopropylethylamine (20 μL, 0.11 mmol) and HATU (O-(7-azabenzotriazol-1-yl)-N-,N,N',N'-tetramethyluronium hexafluorophosphate) (25 mg, 0.07 mmol). The resulting solution was stirred under nitrogen at room temperature overnight. Reaction was incomplete so more ammonium chloride (10 mg, 0.19 mmol), DIPEA (20 μL, 0.11 mmol) and HATU (25 mg, 0.07 mmol) were added and the mixture was stirred under nitrogen for a further 24 hours. The solvent was evaporated in vacuo and the product was purified by preparative TLC, eluting with ethyl acetate to give the title compound.

$^1$H NMR (CDCl$_3$): δ 10.19 (1H, brs), 8.46 (1H, d), 8.27-8.24 (2H, m), 8.10 (1H, d), 7.17 (1H, d), 7.12-7.01 (2H,m), 6.88 (1H, m), 6.80 (1H,m), 6.00 (1H, d), 5.46 (1H, brs), 5.34 (1H, d), 4.45-4.34 (1H, m), 3.31 (1H, t), 2.56-2.48 (2H, m), 2.42 (1H, dd), 2.12-1.99 (1H, m), 1.37 (9H, s), 1.19 (3H, d), 1.15 (3H, d).

Example 21

Enantiomer A of rel-(2S,4S,5R)-1-(3-Bromo-4-tert-butylbenzoyl)-2-isobutyl-4-(5-methyl-pyrazin-2-yl)-5-(1,3-thiazol-2-yl)pyrrolidine-2-carboxylic acid

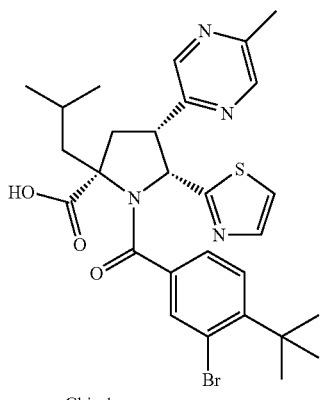

Chiral;
Relative stereochemistry shown

The title compound was prepared from Intermediate 20 (Enantiomer A) in a similar manner to that described in Example 1.
MS calcd for (C$_{28}$H$_{33}$BrN$_4$O$_3$S+H)$^+$: 585/587.
MS found (electrospray): (M+H)$^+$=585/587.

Example 22 rel-(2S,4S,5R)-1-(4-tert-Butylbenzoyl)-2-isobutyl-4-(quinoxalin-2-yl)-5-(1,3-thiazol-2-yl)pyrrolidine-2-carboxylic acid

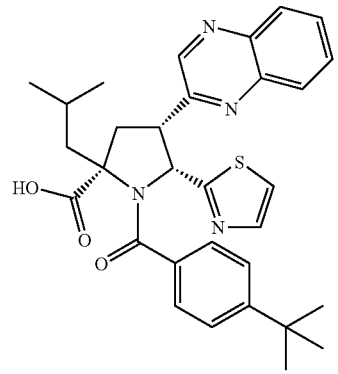

Racemic;
Relative stereochemistry shown

This was prepared from Intermediate 35 in a similar manner to that described in Example 1. Purification was achieved by reverse phase HPLC on a C$_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This provided the title compound as a solid.
MS calcd for (C$_{31}$H$_{34}$N$_4$O$_3$S+H)$^+$: 543.
MS found (electrospray): (M+H)$^+$=543.

Example 23 rel-(2S,4S,5R)-1-(4-tert-Butylbenzoyl)-2-isobutyl-4-(4-trifluoromethyl-pyridin-2-yl)-5-(1,3-thiazol-2-yl)pyrrolidine-2-carboxylic acid

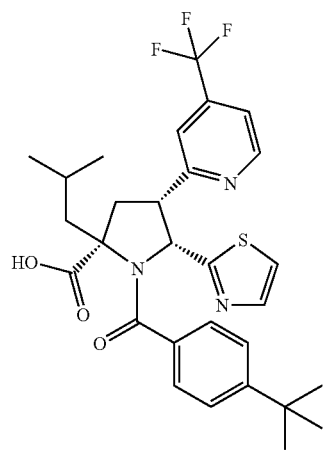

Racemic;
Relative stereochemistry shown

The title compound was prepared as a solid from Intermediate 37 in a similar manner to that described in Example 1.

MS calcd for $(C_{29}H_{32}F_3N_3O_3S+H)^+$: 560.
MS found (electrospray): $(M+H)^+=560$.

Example 24 rel-(2S,4S,5R)-1-(4-tert-Butyl-3-methylbenzoyl)-2-isobutyl-4-(pyrazin-2-yl)-5-(1,3-thiazol-2-yl)pyrrolidine-2-carboxylic acid

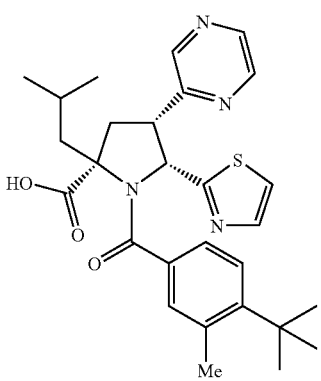

Racemic;
Relative stereochemistry shown

The title compound was prepared as a solid from Intermediate 38 in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the factions by electrospray mass spectroscopy.

MS calcd for $(C_{28}H_{34}N_4O_3S+H)^+$: 507.
MS found (electrospray): $(M+H)^+=507$.

Example 25

Enantiomer A of rel-(2S,4S,5R)-1-(3-Bromo-4-tert-butylbenzoyl)-2-isobutyl-4-(pyrazin-2-yl)-5-(1,3-thiazol-2-yl)pyrrolidine-2-carboxamide

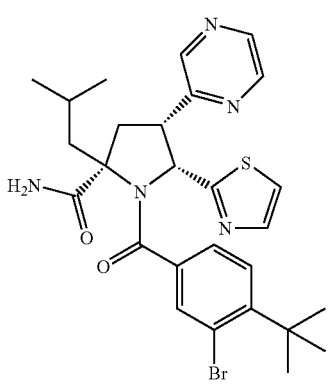

Chiral;
Relative stereochemistry shown

The title compound was prepared as a solid from Example 13, in a similar manner to that described in Example 20.

MS calcd for $(C_{27}H_{32}BrN_5O_2S+H)^+$: 570/572.
MS found (electrospray): $(M+H)^+=570/572$.

Example 26

Enantiomer A of rel-(2S,4S,5R)-1-(4-Butyl-3-methoxybenzoyl)-2-isobutyl-4-(pyrazin-2-yl)-5-pyridin-2-yl)pyrrolidine-2-carboxylic acid

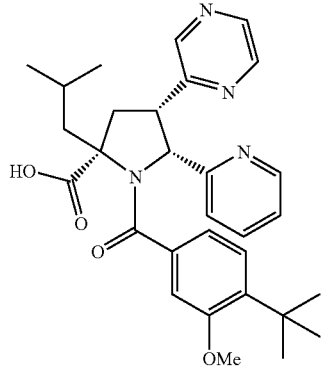

Chiral;
Relative stereochemistry shown

Stage A: Intermediate 15 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-pyrazin-2-yl-5-(pyridin-2-yl)pyrrolidine-2-carboxylic acid, tert butyl ester.

MS calcd for $(C_{34}H_{44}N_4O_4+H)^+$: 573. MS found (electrospray): $(M+H)^+=573$.

Stage B: The racemate from stage A was resolved by preparative HPLC on a Chiralpack AD choromatography column using heptane-isopropanol (90/10, v/v). Evaporation of the fractions containing the second eluted component afforded the title compound as a foam.

MS calcd for $(C_{30}H_{36}N_4O_4+H)^+$: 517.
MS found (electrospray): $(M+H)^+=517$.

Example 27 rel-(2S,4S,5R)-1-(4-tert-Butylbenzoyl)-2-isobutyl-4-(pyrazin-2-yl)-5-(2chloro-1,3-thiazol-5-yl)pyrrolidine-2-carboxylic acid

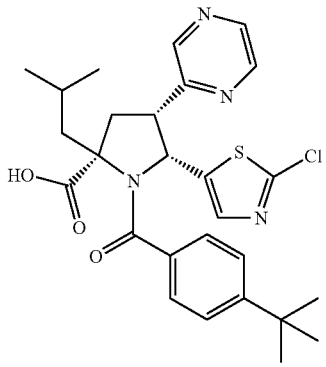

Racemic;
Relative stereochemistry shown

Stage A: Intermediate 41 was reacted with 4-tert-butylbenzoyl chloride in a similar manner to that described in Intermediate 3, to afford rel-(2S,4S,5R)-1-(4-tert-butylbenzoyl)-2-isobutyl-4-pyrazin-2-yl-5-(2-chloro-1,3-thiazol-5-yl)pyrrolidine-2-carboxylic acid, tertbutyl ester.

MS calcd for $(C_{31}H_{39}ClN_4O_3S+H)^+$: 583/585. MS found (electrospray): $(M+H)^+$=583/585.

Stage B: The tert-butyl ester from stage A was deprotected with TFA in a similar manner to that described in Example 1, to afford the title compound as a solid.

MS calcd for $(C_{27}H_{31}ClN_4O_3S+H)^+$: 527/529.
MS found (electrospray): $(M+H)^+$=527/529.

Example 28

Enantiomer A of rel-(2S,4S,5R)-1-(4-tert-Butyl-3-chlorobenzoyl)-2-isobutyl-4-(pyrazin-2-yl)-5-(pyridin-2-yl)pyrrolidine-2-carboxylic acid

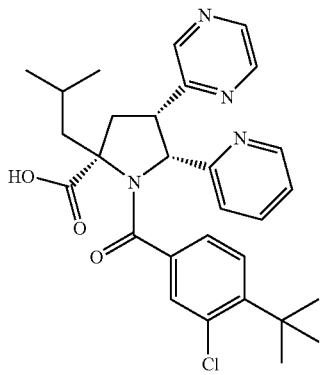

Chiral;
Relative stereochemistry shown

The title compound was prepared as a solid from Intermediate 63 in a similar manner to that described in Example 1.

MS calcd for $(C_{29}H_{33}ClN_4O_3+H)^+$: 521/523.
MS found (electrospray): $(M+H)^+$=521/523.

Example 29 rel-(2S,4S,5R)-1-(4-tert-Butyl-3-methoxybenzoyl)-2-isobutyl-4-(pyrazin-2-yl)-5-(2-chloro-1,3-thiazol-5-yl)pyrrolidine-2-carboxylic acid

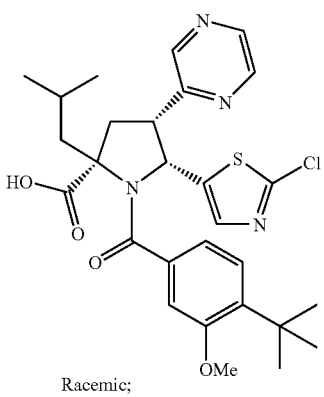

Racemic;
Relative stereochemistry shown

Stage A: Intermediate 41 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-pyrazin-2-yl-5-(2-chloro-1,3-thiazol-5-yl)pyrrolidine-2-carboxylic acid, tert butyl ester.

MS calcd for $(C_{31}H_{39}ClN_4O_3S+H)^+$: 583/585. MS found (electrospray): $(M+H)^+$=583/585.

Stage B: The tert-butyl ester from stage A was deprotected with TFA in a similar manner to that described in Example 1, to afford the title compound as a solid.

MS calcd for $(C_{28}H_{33}ClN_4O_4S+H)^+$: 557/559.
MS found (electrospray): $(M+H)^+$=557/559.

Example 30 rel-(2S,4S,5R)-1-(4-tert-Butylbenzoyl)-2-isobutyl-4-(methyl-pyrazin-2-yl)-5-(1,3-thiazol-2-yl)pyrrolidine-2-carboxylic acid

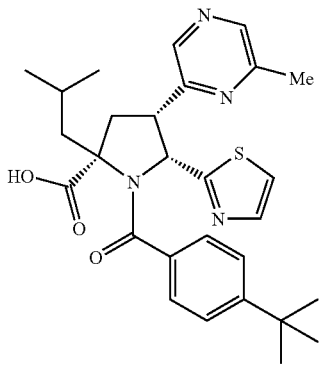

Racemic;
Relative stereochemistry shown

Stage A: Intermediate 43 was reacted with 4-tert-butylbenzoyl chloride in a similar manner to that described in Intermediate 3, to afford rel-(2S,4S,5R)-1-(4-tert-butylbenzoyl)-2-isobutyl-4-(6-methyl-pyrazin-2-yl)-5-(1,3-thiazol-2-yl)pyrrolidine-2-carboxylic acid, tert butyl ester.

MS calcd for $(C_{32}H_{42}N_4O_3S+H)^+$: 563. MS found (electrospray): $(M+H)^+$=563.

Stage B: The tert-butyl ester from stage A was deprotected with TFA in a similar manner to that described in Example 1, to afford the title compound as a solid.

MS calcd for $(C_{28}H_{34}N_4O_3S+H)^+$: 507.
MS found (electrospray): $(M+H)^+$=507.

Example 31 rel-(2S,4S,5R)-1-(4-tert-Butyl-3-methoxybenzoyl)-2-isobutyl-4-(pyrazin-2-yl)-5-phenyl-pyrrolidine-2-carboxylic acid

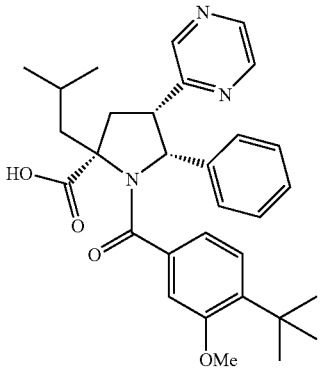

Racemic;
Relative stereochemistry shown

Stage A: Intermediate 45 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-pyrazin-2-yl-5-phenyl-pyrrolidine-2-carboxylic acid, tert-butyl ester.

MS calcd for $(C_{35}H_{45}N_3O_4+H)^+$: 572. MS found (electrospray): $(M+H)^+=572$.

Stage B: The tert-butyl ester from stage A was deprotected with TFA in a similar manner to that described in Example 1, to afford the title compound as a solid.

MS calcd for $(C_{31}H_{37}N_3O_4+H)^+$: 516.
MS found (electrospray): $(M+H)^+=516$.

Example 32 rel-(2S,4S,5R)-1-(4-tert-Butylbenzoyl)-2-isobutyl-4-(pyrazin-2-yl)-5-phenyl-pyrrolidine-2-carboxylic acid

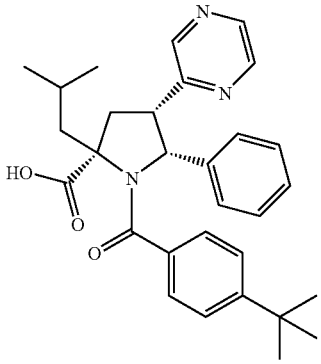

Racemic;
Relative stereochemistry shown

Stage A: Intermediate 45 was reacted with 4-tert-butyl-3-benzoyl chloride in a similar manner to that described in Intermediate 3, to afford rel-(2S,4S,5R)-1-(4-tert-butylbenzoyl)-2-isobutyl-4-pyrazin-2-yl-5-phenyl-pyrrolidine-2-carboxylic acid, tert butyl ester.

MS calcd for $(C_{34}H_{43}N_3O_3+H)^+$: 542. MS found (electrospray): $(M+H)^+=542$.

Stage B: The tert-butyl ester from stage A was deprotected with TFA in a similar manner to that described in Example 1, to afford the title compound as a solid.

MS calcd for $(C_{30}H_{35}N_3O_3+H)^+$: 486.
MS found (electrospray): $(M+H)^+=486$.

Example 33 rel-(2S,4S,5S)-1-(4-tert-Butyl-3-methoxybenzoyl)-2-isobutyl-4-(pyrazin-2-yl)-5-methyl-pyrrolidine-2-carboxylic acid

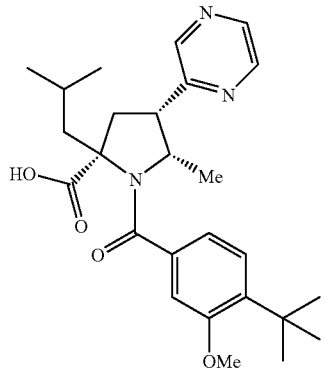

Racemic;
Relative stereochemistry shown

Stage A: Intermediate 47 was reacted with 4-tert-butyl-3-methoxybenzoyl chloride in a similar manner to that described in Intermediate 3, to afford rel-(2S,4S,5S)-1-(4-tert-butyl-3-methoxybenzoyl)-2-isobutyl-4-pyrazin-2-yl-5-methyl-pyrrolidine-2-carboxylic acid, tert butyl ester.

MS calcd for $(C_{30}H_{43}N_3O_4+H)^+$: 510. MS found (electrospray): $(M+H)^+=510$.

Stage B: The tert-butyl ester from stage A was deprotected with TFA in a similar manner to that described in Example 1, to afford the title compound as a solid.

MS calcd for $(C_{26}H_{35}N_3O_4+H)^+$: 454.
MS found (electrospray): $(M+H)^+=454$.

Example 34 rel-(2S,4S,5R)-1-(4-tert-Butyl-3-methoxybenzoyl)-2-isobutyl(pyrazin-2-yl)-5-(pyridin-3-yl)-pyrrolidine-2-carboxylic acid, trifluoroacetate

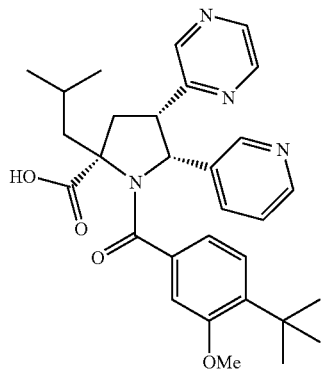

Racemic;
Relative stereochemistry shown

Stage A: Intermediate 49 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-pyrazin-2-yl-5-(pyridin-3-yl)-pyrrolidine-2-carboxylic acid, tert butyl ester.

MS calcd for $(C_{34}H_{44}N_4O_4+H)^+$: 573. MS found (electrospray): $(M+H)^+=573$.

Stage B: The tert-butyl ester from stage A was deprotected with TFA in a similar manner to that described in Example 1, to afford the title compound as a solid MS calcd for $(C_{30}H_{36}N_4O_4+H)^+$: 517.
MS found (electrospray): $(M+H)^+=517$.

Example 35 rel-(2S,4S,5R)-1-(4-tert-Butyl-3-methoxybenzoyl)-2-isobutyl-4-(pyrazin-2-yl)-5-(thien-2-yl)pyrrolidine-2-carboxylic acid

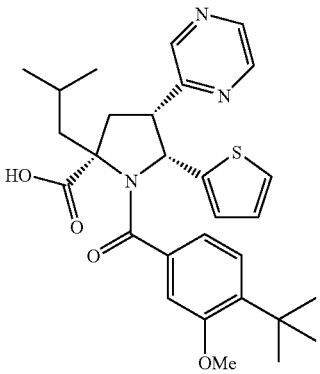

Racemic;
Relative stereochemistry shown

Stage A: Intermediate 51 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-(pyrazin-2-yl)-5-(thiophen-2-yl)pyrrolidine-2-carboxylic acid, tert butyl ester.

MS calcd for $(C_{33}H_{43}N_3O_4+H)^+$: 578. MS found (electrospray): $(M+H)^+=578$.

Stage B: The tert-butyl ester from stage A was deprotected with TFA in a similar manner to that described in Example 1, to afford the title compound as a solid.

MS calcd for $(C_{29}H_{35}N_3O_4S+H)^+$: 522.
MS found (electrospray): $(M+H)^+=522$.

Example 36 rel-(2S,4S,5R)-1-(4-tert-Butylbenzoyl)-2-isobutyl-4-(pyrazin-2-yl)-5-(1,3-thiazol-4-yl)pyrrolidine-2-carboxylic acid

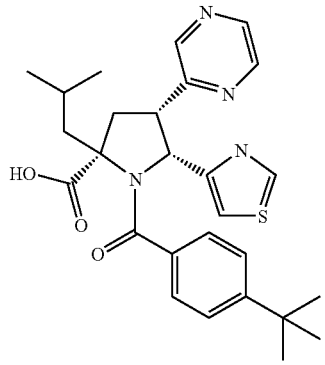

Racemic;
Relative stereochemistry shown

Stage A: Intermediate 53 was reacted with 4-tert-butylbenzoyl chloride in a similar manner to that described in Intermediate 3, to afford rel-(2S,4S,5R)-1-(4-tert-butylbenzoyl)-2-isobutyl-4-pyrazin-2-yl-5-(1,3-thiazol-4-yl)pyrrolidine-2-carboxylic acid, tert butyl ester.

MS calcd for $(C_{31}H_{40}N_4O_3+H)^+$: 549. MS found (electrospray): $(M+H)^+=549$.

Stage B: The tert-butyl ester from stage A was deprotected with TFA in a similar manner to that described in Example 1, to afford the title compound as a solid.

MS calcd for $(C_{27}H_{32}N_4O_3S+H)^+$: 493.
MS found (electrospray): $(M+H)^+=493$.

Example 37 rel-(2S,4S,5R)-1-(4-tert-Butyl-3-methoxybenzoyl)-2-isobutyl-4-(pyrazin-2-yl)-5-(2-dimethylamino-1,3-thiazol-4-yl)pyrrolidine-2-carboxylic acid

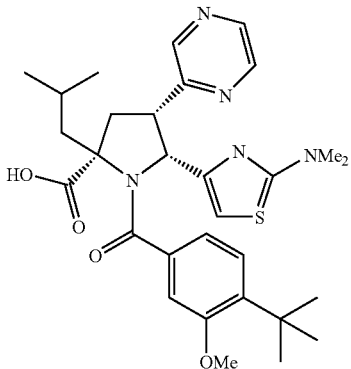

Racemic;
Relative stereochemistry shown

Stage A: Intermediate 56 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-(pyrazin-2-yl)-5-(2-dimethylamino-1,3-thiazol-4-yl)pyrrolidine-2-carboxylic acid, tert butyl ester.

MS calcd for $(C_{34}H_{47}N_5O_4S+H)^+$: 622. MS found (electrospray): $(M+H)^+=622$.

Stage B: The tert-butyl ester from stage A was deprotected with TFA in a similar manner to that described in Example 1, to afford the title compound as a solid.

MS calcd for $(C_{30}H_{39}N_5O_4S+H)^{30}$ : 566.
MS found (electrospray): $(M+H)^+=566$.

Example 38 rel-(2S,4S,5R)-1-(4-tert-Butyl-3-methoxybenzoyl)-2-isobutyl-4-(pyrazin-2-yl)-5-(thiazol-4-yl)pyrrolidine-2-carboxylic acid

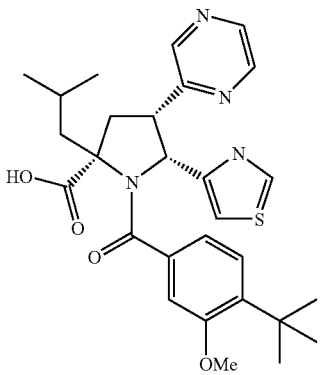

Racemic;
Relative stereochemistry shown

Stage A: Intermediate 53 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-(pyrazin-2-yl)-5-(thiazol-4-yl)pyrrolidine-2-carboxylic acid, tert butyl ester.

MS calcd for $(C_{32}H_{42}N_4O_4S+H)^+$: 579. MS found (electrospray): $(M+H)^+=579$.

Stage B: The tert-butyl ester from stage A was deprotected with TFA in a similar manner to that described in Example 1, to afford the title compound as a solid.

MS calcd for $(C_{28}H_{34}N_4O_4S+H)^+$: 523.
MS found (electrospray): $(M+H)^+=523$.

Example 39 rel-(2S,4S,5R)-1-(4-tert-Butylbenzoyl)-2-isobutyl-4-(pyrazin-2-yl)-5-(pyridin-3-yl)-pyrrolidine-2-carboxylic acid, trifluoroacetate salt

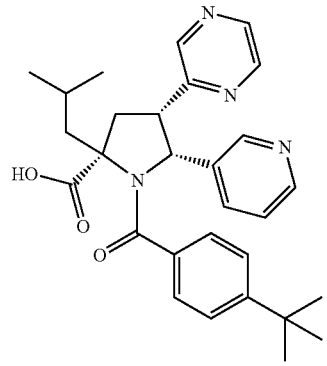

Racemic;
Relative stereochemistry shown

Stage A: Intermediate 49 was reacted with 4-tert-butylbenzoyl chloride in a similar manner to that described in Intermediate 3, to afford rel-(2S,4S,5R)-1-(4-tert-butyl-3-benzoyl)-2-isobutyl-4-(pyrazin-2-yl)-5-(thiazol-4-yl)pyrrolidine-2-carboxylic acid, tert butyl ester.

MS calcd for $(C_{33}H_{42}N_4O_3+H)^+$: 543. MS found (electrospray): $(M+H)^+=543$.

Stage B: The tert-butyl ester from stage A was deprotected with TFA in a similar manner to that described in Example 1, to afford the title compound as a solid.

MS calcd for $(C_{29}H_{34}N_4O_3+H)^+$: 487.
MS found (electrospray): $(M+H)^+=487$.

Example 40 rel-(2S,4S,5R)-1-(4-tert-Butyl-3-methoxybenzoyl)-2-(pyridin-2-ylmethyl)-4-(pyrazin-2-yl)-5-(1,3-thiazol-2-yl)pyrrolidine-2-carboxylic acid

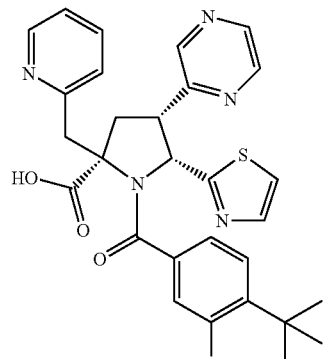

Racemic;
Relative stereochemistry shown

Stage A: Intermediate 89 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-(pyridin-2-ylmethyl)-4-(pyrazin-2-yl)-5-(1,3-thiazol-2-yl)pyrrolidine-2-carboxylic acid, tert-butyl ester.

MS calcd for $(C_{34}H_{39}N_5O_4S+H)^+$=614. MS found (electrospray): $(M+H)^+$=614.

Stage B: The tert-butyl ester from stage A was deprotected with TFA in a similar manner to that described in Example 1, to afford the title compound as a solid.

MS calcd for $(C_{30}H_{31}N_5O_4S+H)^+$: 558.
MS found (electrospray): $(M+H)^+$=558.

Example 41 rel-(2S,4S,5R)-1-(4-tert-Butyl-3-methoxybenzoyl)-2-(N-methylaminocarbonylmethyl)-4-(pyrazin-2-yl)-5-(1,3-thiazol-2-yl)pyrrolidine-2-carboxylic acid

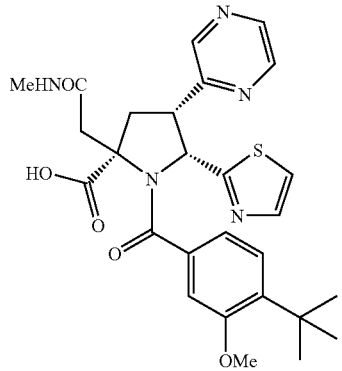

Racemic;
Relative stereochemistry shown

The title compound was prepared as a solid from Intermediate 62, in a similar manner to that described in Example 1.

MS calcd for $(C_{27}H_{31}N_5O_5S+H)^+$: 538.
MS found (electrospray): $(M+H)^+$=538.

Example 42 rel-(2S,4S,5R)-1-(4-tert-Butyl-3-methoxybenzoyl)-2-aminocarbonylmethyl-4-(pyrazin-2-yl)-5-(1,3-thiazol-2-yl)pyrrolidine-2-carboxylic acid

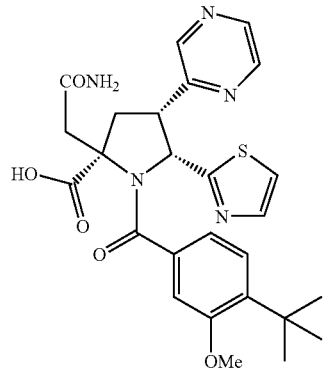

Racemic;
Relative stereochemistry shown

The title compound was prepared as a solid from Intermediate 61 in a similar manner to that described in Example 1.

MS calcd for $(C_{26}H_{29}N_5O_5S+H)^+$: 524.
MS found (electrospray): $(M+H)^+$=524.

Example 43 rel-(2S,4S,5R)-1-(4-tert-Butylbenzoyl)-2-isobutyl-4-(pyrazin-2-yl)-5-(3-phenyl phenyl)-pyrrolidine-2-carboxylic acid

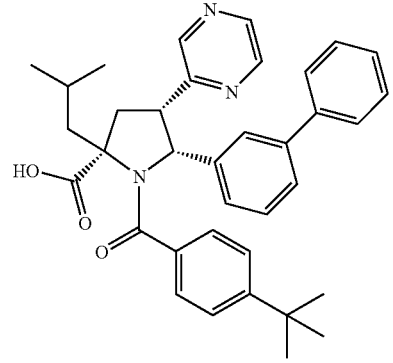

Racemic;
Relative stereochemistry shown

Stage A: Intermediate 65 was reacted with 4-tert-butyl-benzoyl chloride in a similar manner to that described in Intermediate 3, to afford rel-(2S,4S,5R)-1-(4-tert-butylbenzoyl)-2-isobutyl-4-pyrazin-2-yl-5-(3-phenyl phenyl)pyrrolidine-2-carboxylic acid, tert butyl ester.

MS calcd for $(C_{40}H_{47}N_3O_3+H)^+$: 618. MS found (electrospray): $(M+H)^+$=618.

Stage B: The tert-butyl ester from stage A was deprotected with TFA in a similar manner to that described in Example 1, to afford the title compound as a solid.

MS calcd for $(C_{36}H_{39}N_3O_3+H)^+$: 562.
MS found (electrospray): $(M+H)^+$=562.

Example 44

(2S,4S,5R)-1-(4-tert-Butyl-3-methoxybenzoyl)-2-isobutyl-4-(pyrazin-2-yl)-5-(1,3-thiazol-2-yl)pyrrolidine-2-carboxamide

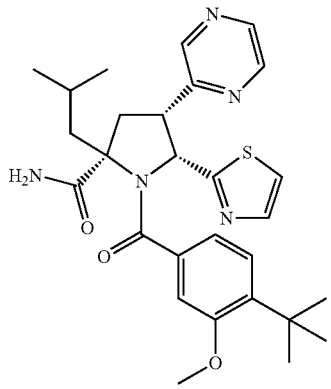

Chiral;
Relative stereochemistry shown

The title compound was prepared from Example 19, in a similar manner to that described in Example 20.

MS calcd for $(C_{28}H_{35}N_5O_3S+H)^+$: 522.
MS found (electrospray): $(M+H)^+$=522.

Example 45

(2S,4R,5R)-1-(4-tert-Butylbenzoyl)-2-isobutyl-4-(5-trifluoromethylpyridin-2-yl)-5-(1,3-thiazol-2-yl)pyrrolidine-2-carboxylic acid

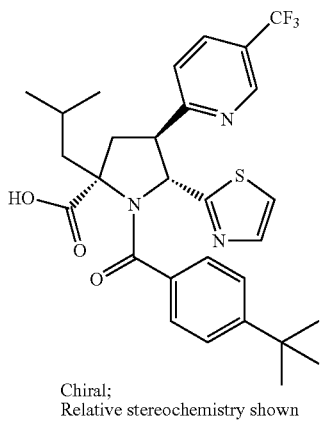

Chiral;
Relative stereochemistry shown

The title compound was prepared from Intermediate 69, in a similar manner to that described in Example 1.
MS calcd for $(C_{29}H_{32}F_3N_3O_3S+H)^+$: 560.
MS found (electrospray): $(M+H)^+$=560.

Example 46 rel-(2S,4S,5R)-1-(4-tert-butylbenzoyl)-2-isobutyl-4-(pyrazin-2-yl)-5-(1,3-thiazol-5-yl)pyrrolidine-2-carboxylic acid

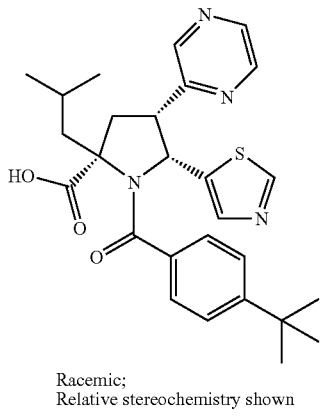

Racemic;
Relative stereochemistry shown

A mixture of Example 27 (40 mg, 0.076 mmol) and 10% palladium on carbon catalyst (40 mg) in ethanol (5 mL) was hydrogenated over 5 days. The catalyst was removed by filtration and washed with ethanol. Following evaporation of the solvent the title compound was purified by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy.
MS calcd for $(C_{27}H_{32}N_4O_3S+H)^+$: 493.
MS found (electrospray): $(M+H)^+$=493.

Example 47 rel-(2S,4S,5R)-1-(4-tert-Butyl-3-methoxybenzoyl)-2-isobutyl-4-(pyrazin-2-yl)-5-(4-dimethylaminophenyl)-pyrrolidine-2-carboxylic acid

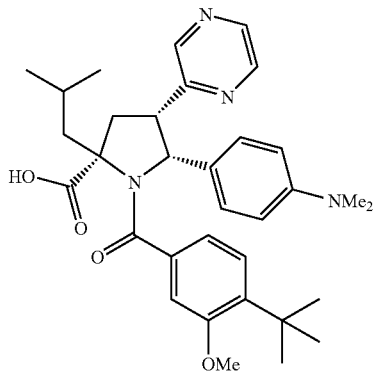

Racemic;
Relative stereochemistry shown

Stage A: Intermediate 70 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-pyrazin-2-yl-5-(4-dimethylaminophenyl)-pyrrolidine-2-carboxylic acid, tert butyl ester.
MS calcd for $(C_{37}H_{50}N_4O_4+H)^+$: 615. MS found (electrospray): $(M+H)^+$=615.

Stage B: The tert-butyl ester from stage A was deprotected with TFA in a similar manner to that described in Example 1, to afford the title compound as a solid
MS calcd for $(C_{33}H_{42}N_4O_4+H)^+$: 559.
MS found (electrospray): $(M+H)^+$=559.

Example 48 rel-(2S,4S,5R)-1-(4-tert-Butylbenzoyl)-2-isobutyl-4-(pyrazin-2-yl)-5-(4-dimethylaminophenyl)-pyrrolidine-2-carboxylic acid

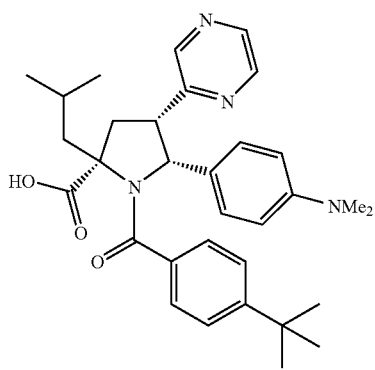

Racemic;
Relative stereochemistry shown

Stage A: Intermediate 70 was reacted with 4-tert-butyl-benzoyl chloride in a similar manner to that described inIntermediate 3, to afford rel-(2S,4S,5R)-1-(4-tert-butyl-benzoyl)-2-isobutyl-4-pyrazin-2-yl-5-(4-dimethylami-nophenyl)-pyrrolidine-2-carboxylic acid, tert butyl ester.

MS calcd for $(C_{36}H_{48}N_4O_3+H)^+$: 585. MS found (electrospray): $(M+H)^+$=585.

Stage B: The tert-butyl ester from stage A was deprotected with TFA in a similar manner to that described in Example 1, to afford the title compound as a solid.

MS calcd for $(C_{32}H_{40}N_4O_3+H)^+$: 529.

MS found (electrospray): $(M+H)^+$=529.

Example 49 rel-(2S,4S,5R)-1-(4-tert-Butyl-3-methoxybenzoyl)-2-(1H-imidazole-4-yl-methyl)-4-(pyrazin-2-yl)-5-(1,3-thiazol-2-yl)-pyrrolidine-2-carboxylic acid

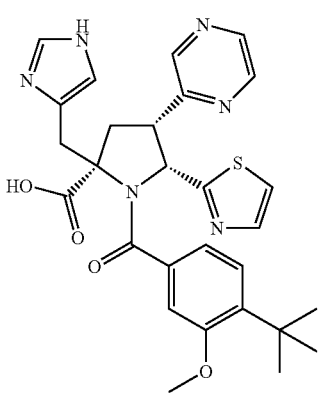

Racemic;
Relative stereochemistry shown

Stage A: Intermediate 72 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-(1H-1-triphenylmethyl-imidazole-4-yl-methyl)-4-pyrazin-2-yl-5-(1,3-thiazol-2-yl)-pyrrolidine-2-carboxylic acid tert butyl ester.

MS calcd for $(C_{51}H_{52}N_6O_4S+H)^+$: 845. MS found (electrospray): $(M+H)^+$=845.

Stage B: The tert-butyl ester from stage A was deprotected with TFA in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{28}H_{30}N_6O_4S+H)^+$: 547.

MS found (electrospray): $(M+H)^+$=547.

Example 50 rel-(2S,4S,5S)-1-(4-tert-Butyl-3-methoxybenzoyl)-2-isobutyl-4-(pyrazin-2-yl)-5-isopropyl-pyrrolidine-2-carboxylic acid

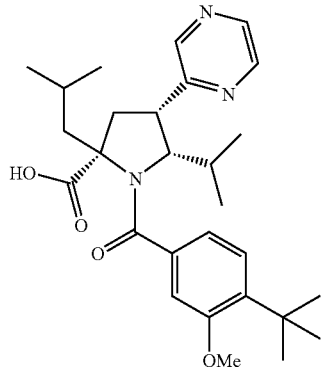

Racemic;
Relative stereochemistry shown

Stage A: Intermediate 74 was reacted with 4-tert-butyl-3-methoxybenzoyl chloride in a similar manner to that described in Intermediate 3, to afford rel-(2S,4S,5S)-1-(4-tert-butyl-3-methoxybenzoyl)-2-isobutyl-4-pyrazin-2-yl-5-isopropyl-pyrrolidine-2-carboxylic acid, tert butyl ester.

MS calcd for $(C_{32}H_{47}N_3O_4+H)^+$: 538. MS found (electrospray): $(M+H)^+$=538.

Stage B: The tert-butyl ester from stage A was deprotected with TFA in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{28}H_{39}N_3O_4+H)^+$: 482.

MS found (electrospray): $(M+H)^+$=482.

Example 51 rel-(2S,4S,5R)-1-(4-tert-Butyl-3-methoxybenzoyl)-2-(2-(methylthio)ethyl)-4-(pyrazin-2-yl)-5-(1,3-thia-zol-5-yl)-pyrrolidine-2-carboxylic acid

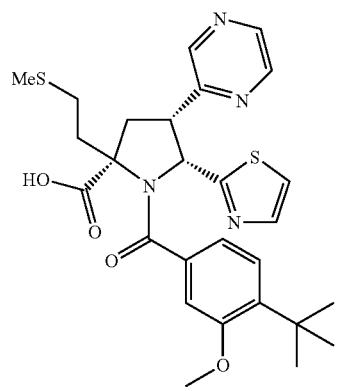

Racemic;
Relative stereochemistry shown

Stage A: Intermediate 76 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-(2-methylthio)ethyl)-4-pyrazin-2-yl-5-(1,3-thiazol-5-yl)-pyrrolidine-2-carboxylic acid, tert butyl ester.

MS calcd for $(C_{31}H_{40}N_4O_4S_2+H)^+$: 597. MS found (electrospray): $(M+H)^+=597$.

Stage B: The tert-butyl ester from stage A was deprotected with TFA in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{27}H_{32}N_4O_4S_2+H)^+$: 541.
MS found (electrospray): $(M+H)^+=541$.

Example 52 rel-(2S,4R,5R)-1-(4-tert-Butylbenzoyl)-2-isobutyl-4-(pyrazin-2-yl)-5-(1,3-thiazol-2-yl)pyrrolidine-2-carboxylic acid

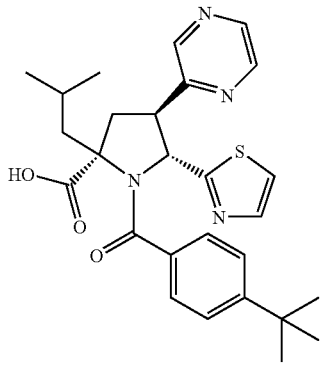

Racemic;
Relative stereochemistry shown

The title compound was prepared as a solid from Intermediate 77, in a similar manner to that described in Example 1.

MS calcd for $(C_{27}H_{32}N_4O_3S+H)^+$: 493.
MS found (electrospray): $(M+H)^+=493$.

Example 53 rel-(2S,4S,5R)-1-(4-tert-Butyl-3-methoxybenzoyl)-2-isobutyl-4-(pyrazin-2-yl)-5-(1,3-thiazol-5-yl)pyrrolidine-2-carboxylic acid

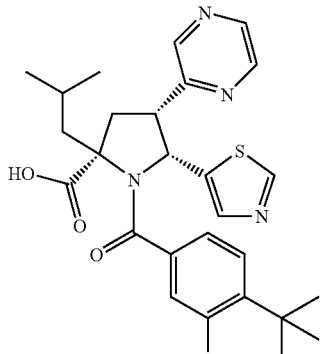

Racemic;
Relative stereochemistry shown

Stage A: Intermediate 41 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-isobutyl-4-pyrazin-2-yl-5-(2-chloro-1,3-thiazol-5-yl)pyrrolidine-2-carboxylic acid tert butyl ester.

MS calcd for $(C_{32}H_{41}ClN_4O_4S+H)^+$: 613/615. MS found (electrospray): $(M+H)^+=613/615$ Stage B: The tert-butyl ester from stage A was deprotected with TFA in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{28}H_{33}ClN_4O_4S+H)^+$: 557/559. MS found (electrospray): $(M+H)^+=557/559$.

Stage C: The acid from stage A was hydrogenated in a similar manner to that described in Example 46. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{28}H_{34}N_4O_4S+H)^+$: 523.
MS found (electrospray): $(M+H)^+=523$.

Example 54 rel-(2S,4S,5R)-1-(4-tert-Butylbenzoyl)-2-isobutyl-4-(4-cyanopyridin-2-yl)-5-(1,3-thiazol-5-yl)pyrrolidine-2-carboxylic acid

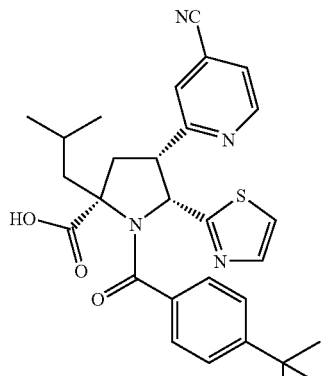

Racemic;
Relative stereochemistry shown

Stage A: Intermediate 79 was reacted with 4-tert-butylbenzoyl chloride in a similar manner to that described in Intermediate 3, to afford rel-(2S,4S,5R)-1-(4-tert-butylbenzoyl)-2-isobutyl-4-(4-cyanopyridin-2-yl)-5-(1,3-thiazol-5-yl)pyrrolidine-2-carboxylic acid tert butyl ester.

MS calcd for $(C_{33}H_{40}N_4O_3S+H)^+$: 573. MS found (electrospray): $(M+H)^+=573$.

Stage B: The tert-butyl ester from stage A was deprotected with TFA in a similar manner to that described in Example 1. Purification was achieved by reverse phase HPLC on a $C_{18}$ column using a two-solvent gradient elution with (A) water containing formic acid (0.1%) and (B) acetonitrile-water (95:5 v/v) containing formic acid (0.05%) as the eluents, and analysis of the fractions by electrospray mass spectroscopy. This afforded the title compound as a solid.

MS calcd for $(C_{29}H_{32}N_4O_3S+H)^+$: 517.
MS found (electrospray): $(M+H)^+=517$.

Example 55 rel-(2S,4R,5R)-1-(4-tert-Butylbenzoyl)-2-isobutyl-4-(pyrimidin-4-yl)-5-(1,3-thiazol-5-yl)pyrrolidine-2-carboxylic acid

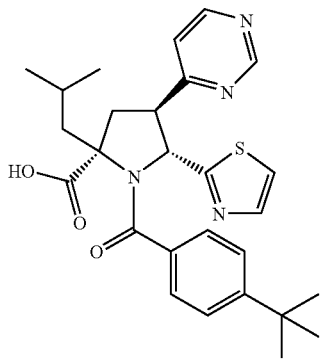

Racemic;
Relative stereochemistry shown

Stage A: Intermediate 81 was reacted with 4-tert-butylbenzoyl chloride in a similar manner to that described in Intermediate 3, to afford rel-(2S,4R,5R)-1-(4-tert-butylbenzoyl)-2-isobutyl-4-(pyrimidin-4-yl)-5-(1,3-thiazol-5-yl)pyrrolidine-2-carboxylic acid, tert butyl ester.
MS calcd for $(C_{31}H_{40}N_4O_3S+H)^+$: 549. MS found (electrospray): $(M+H)^+=549$.

Stage B: The tert-butyl ester from stage A was deprotected with TFA in a similar manner to that described in Example 1. Purification was achieved by reverse phase HPLC on a Supelco ABZ plus column using a gradient of 45-50% acetonitrile/water as the eluent and analysis of the fractions by electrospray mass spectroscopy. The second eluting component was collected and confirmed by nOe studies to be the title compound, isolated as a solid. The first eluted component was the 4-α epimer (Example 56).
MS calcd for $(C_{27}H_{32}N_4O_3S+H)^+$: 493.
MS found (electrospray): $(M+H)^+=493$.

Example 56 rel-(2S,4S,5R)-1-(4-tert-Butylbenzoyl)-2-isobutyl-4-(pyrimidin-4-yl)-5-(1,3-thiazol-5-yl)pyrrolidine-2-carboxylic acid

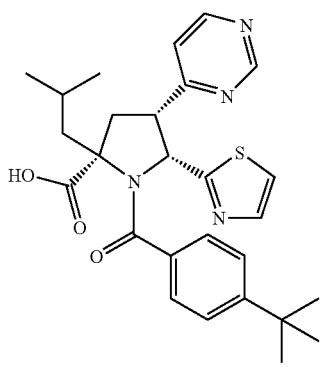

Racemic;
Relative stereochemistry shown

The first eluting component from Example 55, stage B was collected and confirmed by one studies to be the title compound, isolated as a solid.
MS calcd for $(C_{27}H_{32}N_4O_3S+H)^+$: 493.
MS found (electrospray): $(M-H)^+=493$.

Example 57 rel-(2S,4S,5R)-1-(4-tert-Butyl-3-methoxybenzoyl)-2-(2-(methylsuphonyl)ethyl-4-pyrazin-2-yl-5-(1,3-thiazol-2-yl)-pyrrolidine-2-carboxylic acid

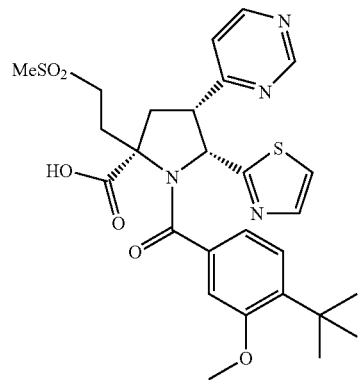

Racemic;
Relative stereochemistry shown

Stage A: Intermediate 83 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-(2-methylsulphonyl)ethyl)-4-pyrazin-2-yl-5-(4-dimethylaminophenyl)-pyrrolidine-2-carboxylic acid, tert butyl ester.
MS calcd for $(C_{31}H_{40}N_4O_6S_2+H)^+$: 629. MS found (electrospray): $(M+H)^+=629$.

Stage B: The tert-butyl ester from stage A was deprotected with TFA in a similar manner to that described in Example 1 to afford the title compound as a solid.
MS calcd for $(C_{27}H_{32}N_4O_6S_2+H)^+$: 573.
MS found (electrospray): $(M+H)^+=573$.

Example 58

Enantiomer of rel-(2S,4R,5R)-1-(4-tert-Butyl-3-methoxybenzoyl)-2-isobutyl-4-(pyrazin-2-yl)-5-(1,3-thiazol-2-yl)pyrrolidine-2-carboxylic acid

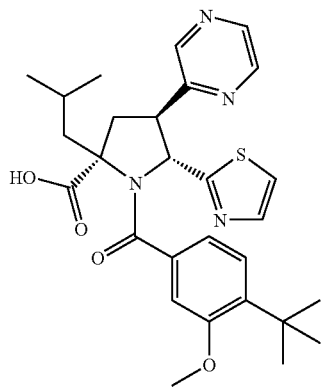

Chiral;
Relative stereochemistry shown

Stage A: Intermediate 27 was epimerised at the C4 position using methanolic sodium hydroxide in a similar manner to that described in Intermediate 77. Purification was by preparative TLC, eluting with cyclohexane/ethyl acetate (1:1, v/v), affording the enantiomer of rel-(2S,4R,5R)-1-(4-tert-butyl-3-methoxybenzoyl)-2-isobutyl-4-(pyrazin-2-yl)-5-(1,3-thiazol-2-yl)pyrrolidine-2-carboxylic acid, tert butyl ester as a solid.

MS calcd for $(C_{32}H_{42}N_4O_4S+H)^+$: 579. MS found (electrospray): $(M+H)^+=579$.

Stage B: The tert-butyl ester from stage A was deprotected with TFA in a similar manner to that described in Example 1, to afford the title compound as a solid.

MS calcd for $(C_{28}H_{34}N_4O_4S+H)^+$: 523.

MS found (electrospray): $(M+H)^+=523$.

Example 59

Enantiomer A of rel-(2S,4S,5R)-1-(4-tert-Butyl-3-methylbenzoyl)-2-isobutyl-4-(pyrazin-2-yl)-5-(1,3-thiazol-2-yl)pyrrolidine-2-carboxylic acid

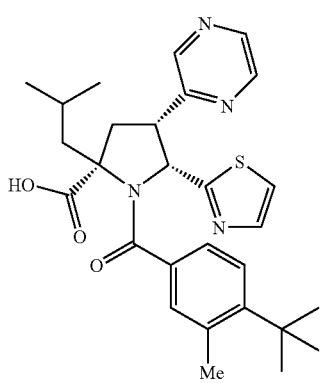

Chiral;
Relative stereochemistry shown

Stage A: Intermediate 92 was reacted with 4-tert-butyl-3-methylbenzoyl chloride in a similar manner to that described in Intermediate 3, to afford enantiomer A of rel-(2S,4S,5R)-1-(4-tert-butyl-3-methylbenzoyl)-2-isobutyl-4-(pyrazin-2-yl)-5-(1,3-thiazol-2-yl)pyrrolidine-2-carboxylic acid, tert butyl ester.

MS calcd for $(C_{32}H_{42}N_4O_3S+H)^+$: 563. MS found (electrospray): $(M+H)^+=563$.

Stage B: The tert-butyl ester from stage A was deprotected with TFA in a similar manner to that described in Example 1. The compound was purified by SPE ($C_{18}$) eluting with water followed by acetonitrile to afford the title compound as a solid.

MS calcd for $(C_{28}H_{34}N_4O_3S+H)^+$: 507.

MS found (electrospray): $(M+H)^+=507$.

Example 60 rel-(2S,4S,5R)-1-(4-tert-Butyl-3-methoxybenzoyl)-2-methyl-4-(pyrazin-2-yl)-5-(1,3-thiazol-5-yl)pyrrolidine-2-carboxylic acid

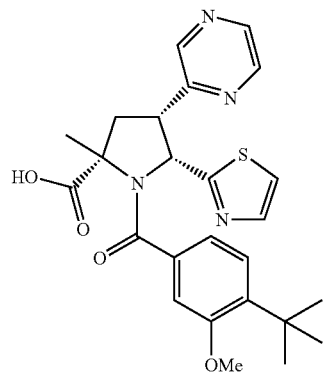

Racemic;
Relative stereochemistry shown

Stage A: Intermediate 85 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-methyl-4-(pyrazin-2-yl)-5-(1,3-thiazol-5-yl)pyrrolidine-2-carboxylic acid, tert butyl ester.

MS calcd for $(C_{29}H_{36}N_4O_4S+H)^+$: 537. MS found (electrospray): $(M+H)^+=537$.

Stage B: The tert-butyl ester from stage A was deprotected with TFA in a similar manner to that described in Example 1 to afford the title compound as a solid.

MS calcd for $(C_{25}H_{28}N_4O_4S+H)^+$: 481.

MS found (electrospray): $(M+H)^+=481$.

Example 61 rel-(2S,4S,5R)-1-(4-tert-Butyl-3-chlorobenzoyl)-2-methyl-4-(pyrazin-4-yl)-5-(1,3-thiazol-5-yl)pyrrolidine-2-carboxylic acid

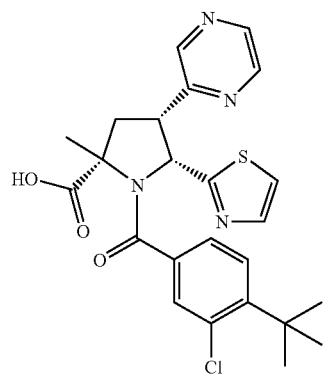

Racemic;
Relative stereochemistry shown

Stage A: Intermediate 85 was reacted with 4-tert-butyl-3-chlorobenzoyl chloride in a similar manner to that described in Intermediate 3, to afford rel-(2S,4S,5R)-1-(4-tert-butyl-3-chlorobenzoyl)-2-methyl-4-(pyrazin-4-yl)-5-(1,3-thiazol-5-yl)pyrrolidine-2-carboxylic acid, tert butyl ester.

MS calcd for $(C_{28}H_{33}ClN_4O_3S+H)^+$: 541/543. MS found (electrospray): $(M+H)^+=541/543$ Stage B: The tert-butyl ester from stage A was deprotected with TFA in a similar manner to that described in Example 1 to afford the title compound as a solid.

MS calcd for $(C_{24}H_{25}ClN_4O_3S+H)^+$: 485/487.
MS found (electrospray): $(M+H)^+485/487$.

Example 62

(2S,4R,5R)-1-(4-tert-Butyl-3-methoxybenzoyl-2-isobutyl-4-(pyrazin-2-yl)-5-(pyridin-2-yl)pyrrolidine-2-carboxylic acid, sodium salt

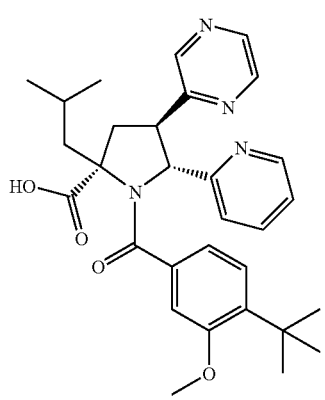

Racemic;
Relative stereochemistry shown

Stage A: rel-(2S,4S,5R)-1-(4-tert-Butyl-3-methoxybenzoyl)-2-isobutyl-4-pyrazin-2-yl-5-(pyridin-2-yl)pyrrolidine-2-carboxylic acid tert butyl ester, from Example 26, Stage A, was epimerised at the C4 position using methanolic sodium hydroxide in a similar manner to that described in Intermediate 77. The reaction was heated for 8 days at 55° C. After the extraction and evaporation of the organic phase, no further purification was required, thus affording (2S,4R,5R)-1-(4-tert-butyl-3-methoxybenzoyl)-2-isobutyl-4-(pyrazin-2-yl)-5-(pyridin-2-yl)pyrrolidine-2-carboxylic acid, tert butyl ester as a solid.

MS calcd for $(C_{34}H_{43}N_4O_4+H)^+$: 573. MS found (electrospray): $(M+H)^+=573$.

Stage B: The tert-butyl ester from stage A was deprotected with TFA in a similar manner to that described in Example 1. After removal of the TFA in vacuo, the residue was dissolved in THF (6 mL) and treated with sodium hydroxide solution (0.1N, 1.9 mL). The THF was removed in vacuo, the residue dissolved in water and freezedried to afford the title compound as a solid.

MS calcd for $(C_{30}H_{35}N_4O_4+H)^+$: 517.
MS found (electrospray): $(M+H)^+=517$.

Example 63 rel-(2S,4S,5R)-1-(4-tert-Butyl-3-methylbenzoyl)-2-isobutyl-4-(pyrazin-2-yl)-5-(1,3-thiazol-4-yl)pyrrolidine-2-carboxylic acid

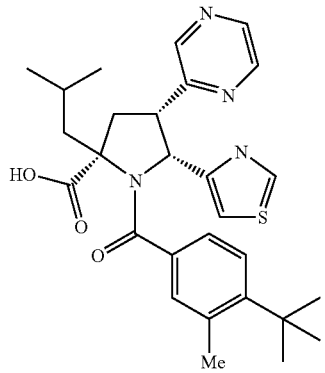

Racemic;
Relative stereochemistry shown

Stage A: Intermediate 53 was reacted with 4-tert-butyl-3-methylbenzoyl chloride in a similar manner to that described in Intermediate 3, to afford rel-(2S,4S,5R)-1-(4-tert-butyl-3-methylbenzoyl)-2-isobutyl-4-pyrazin-2-yl-5-(1,3-thiazol-4-yl)pyrrolidine-2-carboxylic acid, tert butyl ester.

MS calcd for $(C_{32}H_{42}N_4O_3S+H)^+$: 563. MS found (electrospray): $(M+H)^+=563$.

Stage B: The tert-butyl ester from stage A was deprotected with TFA in a similar manner to that described in Example 1. The compound was purified by SPE $(C_{18})$ eluting with water followed by acetonitrile to afford the title compound as a solid.

MS calcd for $(C_{28}H_{34}N_4O_3S+H)^+$: 507.
MS found (electrospray): $(M+H)^+=507$.

Example 64 rel-(2S,4S,5R)-1-(4-tert-Butylbenzoyl)-2-isobutyl-4-(pyrazin-2-yl)-5-(2-phenyl-1,3-thiazol-4-yl)pyrrolidine-2-carboxylic acid

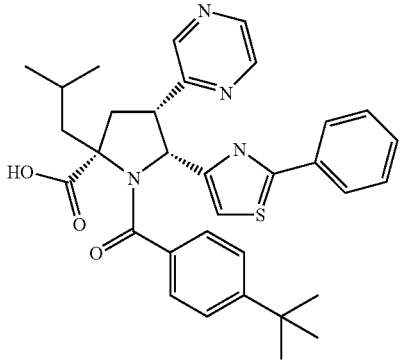

Racemic;
Relative stereochemistry shown

Stage A: Intermediate 86 was reacted with 4-tert-butylbenzoyl chloride in a similar manner to that described in Intermediate 3, to afford rel-(2S,4S,5R)-1-(4-tert-butylbenzoyl)-2-isobutyl-4-pyrazin-2-yl-5-(2-phenyl-1,3-thiazol-4-yl)pyrrolidine-2-carboxylic acid, tert butyl ester.

MS calcd for $(C_{37}H44N_4O_3S+H)^+$: 625. MS found (electrospray): $(M+H)^+=625$.

Stage B: The tert-butyl ester from stage A was deprotected with TFA in a similar manner to that described in Example 1 and purified by reverse phase HPLC to afford the title compound as a solid.

MS calcd for $(C_{33}H_{36}N_4O_3S+H)^+$: 569.
MS found (electrospray): $(M+H)^+=569$.

Example 65

Enantiomer A of rel-(2S,4S,5R)-1-(4-tert-Butyl-3-ethylbenzoyl)-2-isobutyl-4-(pyrazin-2-yl)-5-(1,3-thiazol-2-yl)pyrrolidine-2-carboxylic acid

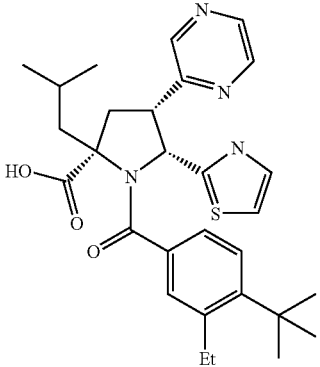

Chiral;
Relative stereochemistry shown

Stage A: Intermediate 92 was reacted with 4-tert-butyl-3-ethylbenzoyl chloride (prepared from 4-tert-butyl-3-ethylbenzoic acid, Intermediate 90) in a similar manner to that described in Intermediate 3, to afford enantiomer A of rel-(2S,4S,5R)-1-(4-tert-butyl-3-ethylbenzoyl)-2-isobutyl-4-pyrazin-2-yl-5-(1,3-thiazol-2-yl)pyrrolidine-2-carboxylic acid, tert-butyl ester.

MS calcd for $(C_{33}H_4N_4O_3S+H)^+$: 577. MS found (electrospray): $(M+H)^+=577$.

Stage B: The tert-butyl ester from stage A was deprotected with TFA in a similar manner to that described in Example 1 to afford the title compound as a solid.

MS calcd for $(C_{29}H_{36}N_4O_3S+H)^+$: 521.
MS found (electrospray): $(M+H)^+=521$.

Example 66

Enantiomer A of rel-(2S,4S,5R)-1-(4-tert-Butyl-3-ethoxybenzoyl)-2-isobutyl-4-(pyrazin-2-yl)-5-(1,3-thiazol-2-yl)pyrrolidine-2-carboxylic acid

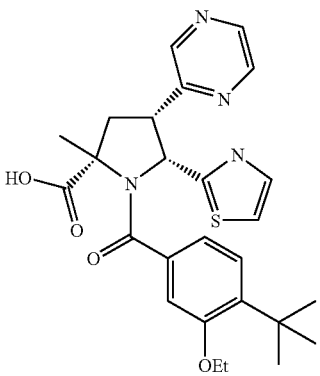

Chiral;
Relative stereochemistry shown

Stage A: Intermediate 92 was reacted with 4-tert-butyl-3-ethoxybenzoyl chloride (prepared from 4-tert-butyl-3-ethoxylbenzoic acid, Intermediate 91) in a similar manner to that described in Intermediate 3, to afford enantiomer A of rel-(2S,4S,5R)-1-(4-tert-butyl-3-ethoxybenzoyl)-2-isobutyl-4-pyrazin-2-yl-5-(1,3-thiazol-2-yl)pyrrolidine-2-carboxylic acid, tert-butyl ester.

MS calcd for $(C_{33}H_{44}N_4O_4S+H)^+$: 593. MS found (electrospray): $(M+H)^+=593$.

Stage B: The tert-butyl ester from stage A was deprotected with TFA in a similar manner to that described in Example 1 to afford the title compound as a solid.

MS calcd for $(C_{29}H_{36}N_4O_4S+H)^+$: 537.
MS found (electrospray): $(M+H)^+=537$.

Example 67 rel-(2S,4S,5R)-1-(4-tert-Butyl-3-methoxybenzoyl)-2-(phenylmethyl)-4-(pyrazin-2-yl)-5-(1,3-thiazol-2-yl)pyrrolidine-2-carboxylic acid

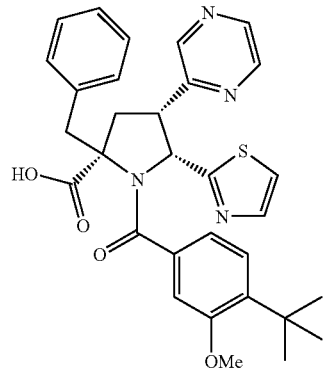

Racemic;
Relative stereochemistry shown

Stage A: Intermediate 94 was reacted with 4-tert-butyl-3-methoxybenzoyl chloride in a similar manner to that described in Intermediate 3, to afford rel-(2S,4S,5R)-1-(4-tert-butyl-3-methoxybenzoyl)-2-phenylmethyl)-4-pyrazin-2-yl-5-(1,3-thiazol-2-yl)pyrrolidine-2-carboxylic acid, tert-butyl ester.

MS calcd for $(C_{35}H_{40}N_4O_4S+H)^+$: 613. MS found (electrospray): $(M+H)^+=613$.

Stage B: The tert-butyl ester from stage A was deprotected with TFA in a similar manner to that described in Example 1, to afford the title compound as a solid.

MS calcd for $(C_{31}H_{32}N_4O_4S+H)^+$: 557.
MS found (electrospray): $(M+H)^+=557$.

The compounds according to the invention may be formulated for administration in any convenient way, and the invention therefore also includes within its scope pharmaceutical compositions for use in therapy, comprising a compound of formula (I) or a physiologically acceptable salt or solvate thereof in admixture with one or more physiologically acceptable diluents or carriers.

The compounds of the present invention can be administered by different routes including intravenous, intraperitoneal, subcutaneous, intramuscular, oral, topical, transdermal, or transmucosal administration. For systemic administration, oral administration is preferred. For oral administration, for example, the compounds can be formulated into conventional oral dosage forms such as capsules, tablets and liquid preparations such as syrups, elixirs and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hanles solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various compounds to be administered can be determined by standard procedures taking into account factors such as the compound ($IC_{50}$) potency, ($EC_{50}$) efficacy, and the biological half-life (of the compound), the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered. Oral administration is a preferred method of administration of the present compounds.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transtucosal or transdermal routes contains suitably from 0.01 mg to 100 mg/Kg, of a compound of Formula(I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose.

Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

No unacceptable topological effects are expected when compounds of the present invention are administered in accordance with the present invention.

Assay

The potential for compounds of the invention to inhibit NS5B wildtype HCV polymerase activity may be demonstrated, for example, using the following in vitro assay:

In Vitro Detection of inhibitors of HCV RNA-dependent RNA Polymerase Activty

Incorporation of [$^3$H]-UMP into RNA was followed by absorption of the RNA polymer onto a DEAE glass fibre filter. A synthetic template consisting of 16 mer oligoU hybridised to polyrA (10:1 w/w) was used as a homopolymer substrate.

Reaction Conditions were 22 µM [$^3$H]-UTP (0.75 Ci/mMol), 1 mM-Dithiothreitol, 3.2 mm-$MgCl_2$, 20 mM-Tris-HCl, pH7.0, 10 µg/mL polyA-oligoU, and 90 mM-NaCl. Note that 50 mM-NaCl is added with the enzyme.

HCV RNA Polymerase Recombinant full-length NS5B (Lohmann et al, J. Virol. 71 (11), 1997, 8416 'Biochemical properties of hepatitis C virus NS5B RNA-dependent RNA polymerase and identification of amino acid sequence motifs essential for enzymatic activity') expressed in baculovirus and purified to homogeneity) was diluted to about 50 µg protein/mL (dependent on specific activity) in 50 mM-Hepes, pH7.0, 0.5 M-NaCl, 20%-Glycerol, 0.05%-Triton X-100, 5 mM-Dithiothreitol, 0.1 mM-EDTA.

5×Concentrated Buffer mix was prepared using 1M-Tris-HCl (pH7.0, 1 mL), 1M-$MgCl_2$ (0.16 mL), 1M-Dithiothreitol (0.05 mL), 5M-NaCl (0.4 mL), and Water (8.4 mL), Total 10 mL.

Substrate Mix was prepared using 5×Concentrated Buffer mix (12 µL), [$^3$H]-UTP (1 µCi/µL; 21.7 µM, 1 µL), 22 µM-UTP (100 µM 13.2 µL), 10 µg/mL polyA-oligoU (100 µg/mL, 6 µL), and Water (12.8 µL), Total 45 µL.

The Assay was set up using Substrate Mix (45 μL), compound (10 μL), and Diluted Enzyme (added last to start reaction) (5 μL), Total 60 μL.

The reaction was performed in a U-bottomed, clear, 96-well plate. The reaction was mixed on a plate-shaker, after addition of the Enzyme, and incubated for 2 h at 22° C. After this time, the reaction was stopped by addition of 25 μL of 100 mM-EDTA.

A DEAE Filtermat (Part No. 1205-105 from Pharmacia) was pre-washed in water and alcohol and dried. 2×20 μL of the Stopped Assay Mix was spotted onto a square of the DEAE Filtermat. The DEAE Filtermat was washed for 2×15 min in SSC buffer (0.3M-NaCl, 30 mM-Na Citrate) followed by 2×2 min in water and 1×1 min in alcohol. The Filtennat was dried and sealed in a bag together with 10 mL of OptiScint HiSafe scintillation fluid. The radioactivity present on the filtermat was detected by scintillation counting on a Wallac 1205 Betaplate counter. After subtraction of background levels without enzyme, any reduction in the amount of radioactivity incorporated in the presence of a compound, compared to that in the absence, was taken as a measure of the level of inhibition. Ten concentrations of compounds were tested in two- or threefold dilutions. From the counts, percentage of inhibition at highest concentration tested or $IC_{50}$s for the compounds were calculated using Grafit3 or Grafit4 software packages.

The exemplified compounds all had an $IC_{50}$ of <50 μM in the above described assay. Accordingly, the compounds of the invention are of potential therapeutic benefit in the treatment and prophylaxis of HCV. Preferred compounds had an $IC_{50}$ of <0.3 μM.

Thus, there is provided as a further aspect of the present invention a compound of formula (I) or a physiologically acceptable salt or solvate thereof for use in human or veterary medical therapy, particularly in the treatment and/or prophylaxis of a viral infection, particularly HCV infection.

It will be appreciated that reference herein to treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

According to another aspect of the invention, there is provided the use of a compound of formula (I) or a physiologically acceptable salt or solvate thereof for the manufacture of a medicament for the treatment and/or prophylaxis of viral infection, particularly HCV infection.

In a further or alternative aspect there is provided a method for the treatment of a human or animal subject with viral infection, particularly HCV infection, which method comprises administering to said human or animal subject an effective amount of a compound of formula (I) or a physiologically acceptable salt or solvate thereof.

The pharmaceutical compositions according to the invention may also be used in combination with other therapeutic agents, for example immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-xidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

The invention thus provides, in a further aspect, a combination comprising a compound of formula (I) or a physiologically acceptable salt or solvate thereof together with another therapeutically active agent.

The combinations referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

All publications, including but not limited to patents and patent applications cited in this specification are herein incorporated by reference as if each individual publication were specifically and individually indicated to be incorporated by reference as though fully set forth.

The invention claimed is:

1. A compound of formula (I)

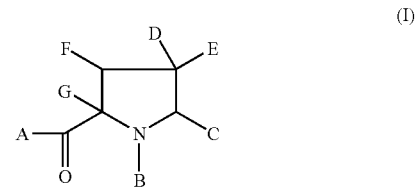

(I)

wherein:

A represents $OR^1$, $NR^1R^2$, or $R^1$ wherein $R^1$ and $R^2$ are independently selected from the group consisting of hydrogen, $C_{1-6}$alkyl, aryl, heteroaryl, arylalkyl, and heteroarylalkyl; or $R^1$ and $R^2$ together with the nitrogen atom to which they are attached form a 5 or 6 membered saturated cyclic group;

B represents $C(O)R^3$ wherein $R^3$ is selected from the group consisting of aryl and heteroaryl;

C represents $C_{1-6}$alkyl, aryl, heteroaryl or heterocyclyl;

D represents a saturated or unsaturated 6-membered heterocyclic ring comprising three or more carbon atoms, each of which may independently be optionally substituted by $R^4$ and $R^5$, and one to three heteroatoms independently selected from N, optionally substituted by hydrogen, $C_{1-6}$alkyl, $C(O)R^3$, $SO_2R^3$, aryl, heteroaryl, arylalkyl, or heteroarylalkyl; O; and S, optionally substituted by one or two oxygen atoms; wherein the 6 membered ring may be attached at any endocyclic carbon atom, and may be optionally fused to a saturated or unsaturated 5 or 6 membered carbocyclic or heterocyclic ring which may itself be optionally substituted on a non-fused carbon atom by $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, cyano, oxo, aryl, heteroaryl and heterocyclyl;

$R^4$ and $R^5$ are independently selected from hydrogen, $C_{1-6}$alkyl, halo, $OR^8$, $C(O)NR^6R^7$, $C(O)R^3$, $CO_2H$, $CO_2R^3$, $NR^6R^7$, $NHC(O)R^3$, $NHCO_2R^3$, $NHC(O)NR^1R^2$, $SO_2NR^1R^2$, $SO_2R^3$, nitro, oxo, aryl, heteroaryl and heterocyclyl;

$R^6$ and $R^7$ are independently selected from hydrogen, $C_{1-6}$alkyl, aryl and heteroaryl; and R⁸ represents hydrogen, $C_{1-6}$alkyl, arylalkyl, or heteroarylalkyl;

E represents hydrogen or $C_{1-6}$alkyl;

F represents hydrogen, $C_{1-6}$alkyl, aryl or heteroaryl; and

G represents hydrogen, $C_{1-6}$alkyl, heterocyclylalkyl, arylalkyl or heteroarylalkyl; and salts, hydrates and individual enantiomers thereof, provided that when A is OR¹ then R¹ is other than tert-butyl.

2. A compound of Formula (I) as claimed in claim 1, in which B represents C(O)R³, and R³ is phenyl substituted in the para-position by tert-butyl and optionally further substituted, by methyl, ethyl, methoxy, ethoxy, or halo.

3. A compound of Formula (I) as claimed in claim 1, in which B represents C(O)R³, and R³ represents phenyl substituted in the para-position by tert-butyl and optionally further substituted in the meta-position by methyl, ethyl, methoxy, ethoxy, or halo.

4. A compound of Formula (I) as claimed in claim 1 in which C is selected from the group consisting of $C_{1-6}$alkyl, aryl and heteroaryl.

5. A compound of Formula (I) as claimed in claim 1, in which D is selected from the group (i) consisting of pyridyl, pyranyl, pyrimidinyl, pyridazinyl, pyrazinyl, 2H-1,2-oxazinyl, 2H-1,3-oxazinyl, 2H-1,4-oxazinyl, 2H-1,2-thiazinyl, 2H-1,3-thiazinyl, 2H-1,4-thiazinyl, 1,2,3-triazinyl, 1,2,4-triazinyl, 1,3,5-triazinyl, 2H-1,2,4-oxadiazinyl, 2H-1,2,5-oxadiazinyl, 2H-1,3,4-oxadiazinyl, 2H-1,3,4-oxadiazinyl, 2H-1,3,5-oxadiazinyl, 2H-1,2,4-thiadiazinyl, 2H-1,2,6-thiadiazinyl, 2H-1,3,4-thiadiazinyl, 2H-1,3,5-thiadiazinyl, 1,4,2-dioxazinyl, 4H-1,3,5-dithiazinyl, 1,4,2-dithiazinyl, and partially or fully saturated derivatives thereof; each of which, where applicable, may be optionally substituted on a carbon atom by R⁴ and R⁵, on a nitrogen atom by hydrogen, $C_{1-6}$alkyl, C(O)R³, SO₂R³, aryl, heteroaryl, arylalkyl, or heteroarylalkyl, and on a sulphur atom by one or two oxygen atoms; and each of which may be optionally fused via two adjacent ring carbon atoms to a saturated or unsaturated 5 or 6 membered carbocyclic or heterocyclic ring which may itself be optionally substituted on a non-fused carbon atom by $C_{1-6}$alkyl, halo, OR⁸, C(O)NR⁶R⁷, C(O)R³, CO₂H, CO₂R³, NR⁶R⁷, NHC(O)R³, NHCO₂R³, NHC(O)NR¹R², SO₂NR¹R², SO₂R³, nitro, cyano, oxo, aryl, heteroaryl and heterocyclyl.

6. A compound of Formula (I) as claimed in claim 1, in which D is selected from pyridyl optionally substituted by trifluoromethyl or cyano; pyrimidinyl; pyrazinyl optionally substituted by methyl; pyridazinyl optionally substituted by methyl; or quinoxalinyl.

7. A compound of Formula (I) as claimed in claim 1, in which G is $C_{1-6}$alkyl, benzyl, pyridinylmethyl, N-methylaminocarbonylmethyl or aminocarbonylmethyl.

8. A compound as claimed in claim 1 selected from the group consisting of:

rel-(2S,4S,5R)-1-(4-tert-butylbenzoyl)-2-isobutyl-4-(pyrazin-2-yl)-5-(1,3-thiazol-2-yl)pyrrolidine-2-carboxylic acid;

rel-(2S,4S,5R)-1-(4-tert-butylbenzoyl)-2-isobutyl-4-(5-methyl-pyrazin-2-yl)-5-(1,3-thiazol-2-yl)pyrrolidine-2-carboxylic acid;

rel-(2S,4S,5R)-1-(4-tert-butylbenzoyl)-2-isobutyl-4-(pyridin-2-yl)-5-(1,3-thiazol-2-yl)pyrrolidine-2-carboxylic acid;

rel-(2S,4R,5R)-1-(4-tert-butylbenzoyl)-2-isobutyl-4-(pyridin-4-yl)-5-(1,3-thiazol-2-yl)pyrrolidine-2-carboxylic acid;

rel-(2S,4S,5R)-1-(4-tert-butylbenzoyl)-2-isobutyl-4-(pyrimidin-5-yl)-5-(1,3-thiazol-2-yl)pyrrolidine-2-carboxylic acid;

rel-(2S,4S,5R)-1-(4-tert-butylbenzoyl)-2-isobutyl-4-(6-methyl-pyrazin-2-yl)-5-(1,3-thiazol-2-yl)pyrrolidine-2-carboxylic acid;

rel-(2S,4S,5R)-1-(4-tert-butylbenzoyl)-2-isobutyl-4-(pyrazin-2-yl)-5-(pyridin-2-yl)pyrrolidine-2-carboxylic acid;

rel-(2S,4S,5R)-1-(3-bromo-4-tert-butylbenzoyl)-2-isobutyl-4-(pyrazin-2-yl)-5-(pyridin-2-yl)pyrrolidine-2-carboxylic acid;

rel-(2S,4S,5R)-1-(3-bromo-4-tert-butylbenzoyl)-2-isobutyl-4-(pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(5-methyl-pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(pyridazin-3-yl)-5-(1,3-thiazol-2-yl)pyrrolidine-2-carboxylic acid;

rel-(2S,4S,5R)-1-(4-tert-butylbenzoyl)-2-isobutyl-4-(pyrazin-2-yl)-5-(1,3-benzothiazol-2-yl)pyrrolidine-2-carboxylic acid;

rel-(2S,4S,5R)-1-(3-bromo-4-tert-butylbenzoyl)-2-isobutyl-4-(pyrazin-2-yl)-5-(1,3-benzothiazol-2-yl)pyrrolidine-2-carboxylic acid;

rel-(2S,4S,5R)-1-(4-tert-butyl-3-chlorobenzoyl)-2-isobutyl-4-(pyrazin-2-yl)-5-(1,3-thiazol-2-yl)pyrrolidine-2-carboxylic acid;

rel-(2S,4S,5R)-1-(4-tert-butyl-3-methoxybenzoyl)-2-isobutyl-4-(pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(pyrazin-2-yl)-5-(pyridin-2-yl)pyrrolidine-2-carboxamide;

rel-(2S,4S,5R)-1-(4-tert-butylbenzoyl)-2-isobutyl-4-(quinoxalin-2-yl)-5-(1,3-thiazol-2-yl)pyrrolidine-2-carboxylic acid;

rel-(2S,4S,5R)-1-(4-tert-butylbenzoyl)-2-isobutyl-4-(4-trifluoromethyl-pyridin-2-yl)-5-(1,3-thiazol-2-yl)pyrrolidine-2-carboxylic acid;

rel-(2S,4S,5R)-1-(4-tert-butyl-3-methylbenzoyl)-2-isobutyl-4-(pyrazin-2-yl)-5-(1,3-thiazol-2-yl)pyrrolidine-2-carboxylic acid;

rel-(2S,4S,5R)-1-(3-bromo-4-tert-butylbenzoyl)-2-isobutyl-4-(pyrazin-2-yl)-5-(1,3-thiazol-2-yl)pyrrolidine-2-carboxamide;

rel-(2S,4S,5R)-1-(4-tert-butyl-3-methoxybenzoyl)-2-isobutyl-4-(pyrazin-2-yl)-5-(pyridin-2-yl)pyrrolidine-2-carboxylic acid;

rel-(2S,4S,5R)-1-(4-tert-butylbenzoyl)-2-isobutyl-4-(pyrazin-2-yl)-5-(2-chloro-1,3-thiazol-5-yl)pyrrolidine-2-carboxylic acid;

rel-(2S,4S,5R)-1-(4-tert-butyl-3-chlorobenzoyl)-2-isobutyl-4-(pyrazin-2-yl)-5-(pyridin-2-yl)pyrrolidine-2-carboxylic acid;

rel-(2S,4S,5R)-1-(4-tert-butyl-3-methoxybenzoyl)-2-isobutyl-4-(pyrazin-2-yl)-5-(2-chloro-1,3-thiazol-5-yl)pyrrolidine-2-carboxylic acid;

rel-(2S,4S,5R)-1-(4-tert-butylbenzoyl)-2-isobutyl-4-(6-methyl-pyrazin-2-yl)-5-(1,3-thiazol-2-yl)pyrrolidine-2-carboxylic acid;

rel-(2S,4S,5R)-1-(4-tert-butyl-3-methoxybenzoyl)-2-isobutyl-4-(pyrazin-2-yl)-5-phenyl-pyrrolidine-2-carboxylic acid;

rel-(2S,4S,5R)-1-(4-tert-butylbenzoyl)-2-isobutyl-4-(pyrazin-2-yl)-5-phenyl-pyrrolidine-2-carboxylic acid;

rel-(2S,4S,5S)-1-(4-tert-butyl-3-methoxybenzoyl)-2-isobutyl-4-(pyrazin-2-yl)-5-methyl-pyrrolidine-2-carboxylic acid;
rel-(2S,4S,5R)-1-(4-tert-butyl-3-methoxybenzoyl)-2-isobutyl-4-(pyrazin-2-yl)-5-(pyridin-3-yl)-pyrrolidine-2-carboxylic acid;
rel-(2S,4S,5R)-1-(4-tert-butyl-3-methoxybenzoyl)-2-isobutyl-4-(pyrazin-2-yl)-5-(thien-2-yl)pyrrolidine-2-carboxylic acid;
rel-(2S,4S,5R)-1-(4-tert-butylbenzoyl)-2-isobutyl-4-(pyrazin-2-yl)-5-(1,3-thiazol-4-yl)pyrrolidine-2-carboxylic acid;
rel-(2S,4S,5R)-1-(4-tert-butyl-3-methoxybenzoyl)-2-isobutyl-4-(pyrazin-2-yl)-5-(2-dimethylamino-1,3-thiazol-4-yl)pyrrolidine-2-carboxylic acid;
rel-(2S,4S,5R)-1-(4-tert-butyl-3-methoxybenzoyl)-2-isobutyl-4-(pyrazin-2-yl)-5-(thiazol-4-yl)pyrrolidine-2-carboxylic acid;
rel-(2S,4S,5R)-1-(4-tert-butylbenzoyl)-2-isobutyl-4-(pyrazin-2-yl)-5-(pyridin-3-yl)-pyrrolidine-2-carboxylic acid,
rel-(2S,4S,5R)-1-(4-tert-butyl-3-methoxybenzoyl)-2-(pyridin-2-ylmethyl)-4-(pyrazin-2-yl)-5-(1,3-thiazol-2-yl)pyrrolidine-2-carboxylic acid;
rel-(2S,4S,5R)-1-(4-tert-butyl-3-methoxybenzoyl)-2-(N-methylaminocarbonylmethyl)-4-(pyrazin-2-yl)-5-(1,3-thiazol-2-yl)pyrrolidine-2-carboxylic acid;
rel-(2S,4S,5R)-1-(4-tert-butyl-3-methoxybenzoyl)-2-(aminocarbonylmethyl)-4-(pyrazin-2-yl)-5-(1,3-thiazol-2-yl)pyrrolidine-2-carboxylic acid;
rel-(2S,4S,5R)-1-(4-tert-butylbenzoyl)-2-isobutyl-4-(pyrazin-2-yl)-5-(3-phenyl phenyl)-pyrrolidine-2-carboxylic acid;
(2S,4S,5R)-1-(4-tert-butyl-3-methoxybenzoyl)-2-isobutyl-4-(pyrazin-2-yl)-5-(1,3-thiazol-2-yl)pyrrolidine-2-carboxamide;
(2S,4R,5R)-1-(4-tert-butylbenzoyl)-2-isobutyl-4-(5-trifluoromethylpyridin-2-yl)-5-(1,3-thiazol-2-yl)pyrrolidine-2-carboxamide;
rel-(2S,4S,5R)-1-(4-tert-butylbenzoyl)-2-isobutyl-4-(pyrazin-2-yl)-5-(1,3-thiazol-5-yl)pyrrolidine-2-carboxylic acid;
rel-(2S,4S,5R)-1-(4-tert-butyl-3-methoxybenzoyl)-2-isobutyl-4-(pyrazin-2-yl)-5-(4-dimethylaminophenyl)-pyrrolidine-2-carboxylic acid;
rel-(2S,4S,5R)-1-(4-tert-butylbenzoyl)-2-isobutyl-4-(pyrazin-2-yl)-5-(4-dimethylaminophenyl)-pyrrolidine-2-carboxylic acid;
rel-(2S,4S,5R)-1-(4-tert-butyl-3-methoxybenzoyl)-2-(1H-imidazole-4-yl-methyl)-4-(pyrazin-2-yl)-5-(1,3-thiazol-2-yl)-pyrrolidine-2-carboxylic acid;
rel-(2S,4S,5S)-1-(4-tert-butyl-3-methoxybenzoyl)-2-isobutyl-4-(pyrazin-2-yl)-5-isopropyl-pyrrolidine-2-carboxylic acid;
rel-(2S,4S,5R)-1-(4-tert-butyl-3-methoxybenzoyl)-2-(2-(methylthio)ethyl)-4-(pyrazin-2-yl)-5-(1,3-thiazol-5-yl)-pyrrolidine-2-carboxylic acid;
rel-(2S,4R,5R)-1-(4-tert-butylbenzoyl)-2-isobutyl-4-(pyrazin-2-yl)-5-(1,3-thiazol-2-yl)pyrrolidine-2-carboxylic acid;
rel-(2S,4S,5R)-1-(4-tert-butyl-3-methoxybenzoyl)-2-isobutyl-4-(pyrazin-2-yl)-5-(1,3-thiazol-5-yl)pyrrolidine-2-carboxylic acid;
rel-(2S,4S,5R)-1-(4-tert-butylbenzoyl)-2-isobutyl-4-(4-cyanopyridin-2-yl)-5-(1,3-thiazol-5-yl)pyrrolidine-2-carboxylic acid;
rel-(2S,4R,5R)-1-(4-tert-butylbenzoyl)-2-isobutyl-4-(pyrimidin-4-yl)-5-(1,3-thiazol-5-yl)pyrrolidine-2-carboxylic acid;
rel-(2S,4S,5R)-1-(4-tert-butylbenzoyl)-2-isobutyl-4-(pyrimidin-4-yl)-5-(1,3-thiazol-5-yl)pyrrolidine-2-carboxylic acid;
rel-(2S,4S,5R)-1-(4-tert-butyl-3-methoxybenzoyl)-2-(2-(methylsulphonyl)ethyl)-4-(pyrazin-2-yl)-5-(1,3-thiazol-2-yl)-pyrrolidine-2-carboxylic acid;
rel-(2S,4R,5R)-1-(4-tert-butyl-3-methoxybenzoyl)-2-isobutyl-4-(pyrazin-2-yl)-5-(1,3-thiazol-2-yl)pyrrolidine-2-carboxylic acid;
rel-(2S,4S,5R)-1-(4-tert-butyl-3-methylbenzoyl)-2-isobutyl-4-(pyrazin-2-yl)-5-(1,3-thiazol-2-yl)pyrrolidine-2-carboxylic acid;
rel-(2S,4S,5R)-1-(4-tert-butyl-3-methoxybenzoyl)-2-methyl-4-(pyrazin-2-yl)-5-(1,3-thiazol-5-yl)pyrrolidine-2-carboxylic acid;
rel-(2S,4S,5R)-1-(4-tert-butyl-3-chlorobenzoyl)-2-methyl-4-(pyrazin4-yl)-5-(1,3-thiazol-5-yl)pyrrolidine-2-carboxylic acid;
(2S,4R,5R)-1-(4-tert-butyl-3-methoxybenzoyl)-2-isobutyl-4-(pyrazin-2-yl)-5-(pyridin-2-yl)pyrrolidine-2-carboxylic acid;
rel-(2S,4S,5R)-1-(4-tert-butyl-3-methylbenzoyl)-2-isobutyl-4-(pyrazin-2-yl)-5-(1,3-thiazol-4-yl)pyrrolidine-2-carboxylic acid;
rel-(2S,4S,5R)-1-(4-tert-butylbenzoyl)-2-isobutyl-4-(pyrazin-2-yl)-5-(2-phenyl-1,3-thiazol-4-yl)pyrrolidine-2-carboxylic acid;
rel-(2S,4S,5R)-1-(4-tert-butyl-3-ethylbenzoyl)-2-isobutyl-4-(pyrazin-2-yl)-5-(1,3-thiazol-2-yl)pyrrolidine-2-carboxylic acid;
rel-(2S,4S,5R)-1-(4-tert-butyl-3-ethoxybenzoyl)-2-isobutyl-4-(pyrazin-2-yl)-5-(1,3-thiazol-2-yl)pyrrolidine-2-carboxylic acid; and
rel-(2S,4S,5R)-1-(4-tert-butyl-3-methoxybenzoyl)-2-(phenylmethyl)-4-(pyrazin-2-yl)-5-(1,3-thiazol-2-yl) pyrrolidine-2-carboxylic acid;
and salts, hydrates, and individual enantiomers thereof.

9. pharmaceutical formulation comprising a compound of Formula (I) as claimed in claim 1 in conjunction with a pharmaceutically acceptable diluent or carrier therefor.

10. A method of treating HCV infection which comprises administering to a subject in need thereof, an effective amount of a compound as claimed in claim 1.

11. A method as claimed in claim 10 in which the compound is administered in an oral dosage form.

12. A process for the preparation of compounds of Formula (I) as claimed in claim 1, comprising reaction of a compound of Formula (VI)

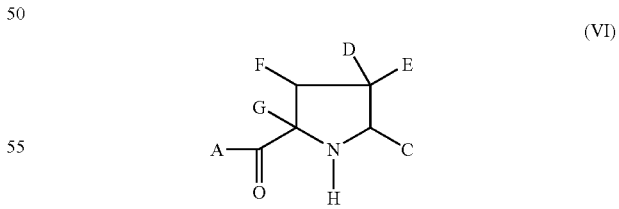

(VI)

in which A, C, D, E, F and G are as defined in claim 1 and where A is $OR^1$ and $R^1$ is hydrogen, optionally A is protected with a suitable hydroxy protecting group; with $R^3C(O)$-hal, wherein hal is a halo atom, and, where A is protected hydroxy, followed by a deprotecting step.

* * * * *